United States Patent
Love et al.

(10) Patent No.: US 9,638,690 B2
(45) Date of Patent: May 2, 2017

(54) COMPOUNDS AND COMPOSITIONS FOR USE AS ALKYLATING AGENT SENSORS AND METHODS OF USE THEREOF

(71) Applicant: The University of British Columbia, Vancouver (CA)

(72) Inventors: Jennifer Ann Love, Vancouver (CA); Philip Andrew Provencher, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 14/927,836

(22) Filed: Oct. 30, 2015

(65) Prior Publication Data

US 2016/0131641 A1    May 12, 2016

Related U.S. Application Data

(60) Provisional application No. 62/076,819, filed on Nov. 7, 2014.

(51) Int. Cl.
| | | |
|---|---|---|
| C07F 7/10 | (2006.01) |
| C07D 213/16 | (2006.01) |
| C09K 3/00 | (2006.01) |
| G01N 33/52 | (2006.01) |
| C07D 213/55 | (2006.01) |
| C07D 213/48 | (2006.01) |
| C07D 213/53 | (2006.01) |
| C07D 213/56 | (2006.01) |
| C07D 213/42 | (2006.01) |
| C07F 7/18 | (2006.01) |

(52) U.S. Cl.
CPC ........... *G01N 33/52* (2013.01); *C07D 213/42* (2013.01); *C07D 213/48* (2013.01); *C07D 213/53* (2013.01); *C07D 213/55* (2013.01); *C07D 213/56* (2013.01); *C07F 7/1836* (2013.01)

(58) Field of Classification Search
USPC ................ 546/333, 335, 14; 252/182.12
See application file for complete search history.

(56) References Cited

U.S. PATENT DOCUMENTS

| | | |
|---|---|---|
| 5,571,897 A | 11/1996 | Takalo et al. |
| 2002/0065296 A1 | 5/2002 | Dumas et al. |
| 2002/0115653 A1 | 8/2002 | Mabire et al. |
| 2004/0102636 A1 | 5/2004 | Miller et al. |
| 2005/0165018 A1 | 7/2005 | Mabire et al. |
| 2005/0277640 A1 | 12/2005 | Dixon et al. |
| 2007/0105858 A1 | 5/2007 | Mabire et al. |
| 2007/0117817 A1 | 5/2007 | Dixon et al. |
| 2007/0244120 A1 | 10/2007 | Dumas et al. |
| 2008/0058334 A1 | 3/2008 | Mabire et al. |
| 2009/0069297 A1 | 3/2009 | Cee et al. |
| 2010/0075967 A1 | 3/2010 | Dixon et al. |
| 2010/0280008 A1 | 11/2010 | Deak et al. |
| 2011/0098301 A1 | 4/2011 | Dixon et al. |
| 2012/0046290 A1 | 2/2012 | Dumas et al. |
| 2012/0122847 A1 | 5/2012 | Cee et al. |

FOREIGN PATENT DOCUMENTS

| | | |
|---|---|---|
| WO | WO 99/32106 A1 | 7/1999 |
| WO | WO 99/32111 A1 | 7/1999 |
| WO | WO 99/32436 A1 | 7/1999 |
| WO | WO 99/32463 A1 | 7/1999 |
| WO | WO 02/085857 A2 | 10/2002 |
| WO | WO 2012/087630 A1 | 6/2012 |
| WO | WO 2013/158422 A1 | 10/2013 |

OTHER PUBLICATIONS

Florio, S. et al.: Vicarious nucleophilic substitution of (chloroalkyl)heterocycles with nitroarenes. Eur. J. Org. Chem., pp. 2118-2124, 2004.*
Albouy, Dominique et al., "Regenerative rolde of the red phosphorus in the couple 'Hl$_{aq}$/P$_{red}$.'" Journal of Organometallic Chemistry, 1997, 529: 295-299.
Bartoli, Giuseppe et al., "The Reaction of Vinyl Grignard Reagents with 2-Substituted Nitroarenes: A New Approach to the Synthesis of 7-Substituted Indoles." Tetrahedron Letters, 1989, 30(16): 2129-2132.
Beak, Peter et al., "Relative Rates of Deprotonation and of Bromine-Lithium Exchange by Organolithium Reagents: Interpretation of Some deceptive Results." Tetrahedron Letters, 1985, 26(41): 4979-4980.
Beak, Peter et al., "Does Formal Intramolecular Transfer of an Acidic Deuterium to a Site of Halogen-Lithium Exchange Show that Lithium-Halogen Exchange is Faster than Loss of the Acidic Deuterium? Evidence in Favor of an Alternative Mechanism." J Am Chem Soc, 1988, 110: 3538-3542.
Beak, Peter et al., "Selectivities in Reactions of Organolithium Reagents with Aryl Bromides Which Bear Proton-Donating Groups." J. Org. Chem., 1993, 58: 7330-7335.

(Continued)

*Primary Examiner* — Charanjit Aulakh
(74) *Attorney, Agent, or Firm* — Saliwanchik, Lloyd & Eisenschenk

(57) ABSTRACT

This invention provides compound having a structure of Formula I:

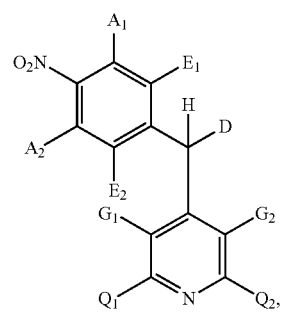

Uses of such compounds and compositions comprising the compounds as alkylating agent sensors.

27 Claims, 3 Drawing Sheets

(56) References Cited

OTHER PUBLICATIONS

Bedics, Matthew A. et al., "Synthesis and Photoelectrochemical Performance of Chalcogenopyrylium Monomethine Dyes Bearing Phosphonate/Phosphonic Acid Substituents." *J. Org. Chem.*, 2013, 78: 8885-8891.

Berman, R. S. et al., "Kinetics and Mechanism of Oxygen Atom Transfer from Nitro Compounds Mediated by Nickel(0) Complexes." *Inorg. Chem.*, 1980, 19: 248-254.

Bosco, Marcella et al., "Mechanistic Studies on the Reaction of Nitro- and Nitrosoarenes with Vinyl Grignard Reagents." *J. Chem. Soc. Perkin Trans.2*, 1991, 5: 657-663.

Buck, Peter et al., "Zur Thermolyse von *o*-Nitro-phenyllithium." *Chem Ber.*, 1970, 103: 1431-1439.

Burke, Martin D. et al., "A Planning Strategy for Diversity-Oriented Synthesis." *Angewandte Chemie Int. Ed.*, 2004, 43: 46-58.

Busse, Stefan et al., "Gold and thiol surface functionalized integrated optical Mach—Zehnder interferometer for sensing purposes." *Sensors and Actuators B*, 1999, 60: 148-154.

Cameron, James F. et al., "Photogeneration of Organic Bases from *o*-Nitrobenzyl-Derives Carbamates." *J. Am. Chem. Soc.*, 1991, 113: 4303-4313.

Casey, Brain M. et al., "On the Nature of the Oxidative Heterocoupling of Lithium Enolates." *J. Am. Chem. Soc.*, 2011, 133: 11492-11495.

Dierickx, Karen M.E. et al., "Improving the spectrophotometric determination of the alkylating activity of anticancer agents: A new insight into the mechanism of the NBP method." *Talanta*, 2009, 77: 1370-1375.

Diez-Cecilia, Elena et al., "One-step double reduction of aryl nitro and carbonyl groups using hydrazine." *Tetrahedron Letters*, 2011, 52: 6702-6704.

Duez, Stephanie et al., "Lewis Acid Promoted Benzylic Cross-Couplings of Pyridines with Aryl Bromides." *Angew. Chem. Int. Ed.*, 2011, 50: 7686-7690.

Epstein, Joseph et al, "Use of γ-(4-Nitrobenzyl)pyridine as Analytical Reagent for Ethylenimines and Alkylating Agents." *Anal. Chem.*, Sep. 1955, 27(9): 1435-1439.

Fan, Feng et al., "Construction of Polycyclic Spiro-indolines via an Intramolecular Oxidative Coupling/Cyclization Cascade Reaction Process." *Organic Letters*, 2012, 14(6): 1405-1407.

Fan, Xin-Heng et al., "Ni$^{II}$—(δ-Aryl) Complex Catalyzed Suzuki Reaction of Aryl Tosylates with Arylboronic Acids." *Eur. J. Org. Chem.*, 2010, 2457-2460.

Green, Will H. et al., "White Phosphors from a Silicate-Carboxylate Sol-Gel Precursor that Lack Metal Activator Ions." *Science*, Jun. 20, 1997, 276: 1826-1828.

Harrison, M.J. et al., "Reactions of Lead Tetra-acetate, Part IX. The Mechanism of Reaction with Ketone Arylhydrazones." *J. Chem. Soc. (C) Organic*, 1997, 735-739.

Hoffmann, Reinhard W. et al., "$\Delta^3$-Oxdiazoline-(1.3.4) Bei Der Oxydation von Benzoyl-Hydrazonen Mit Bleitetraacetat." *Tetrahedron Letters*, 1966, 4: 411-414.

Jacq, Jerome et al., "A Versatile and Regiospecific Synthesis of Functionalized 1,3-Diarylisobenzofurans." *Organic Letters*, 2008, 10(17): 3757-3760.

Jeffrey, Jenna L. et al., "Intramolecular C(sp$^3$)-N Coupling by Oxidation of Benzylic C,N-Dianions." *Angew. Chem. Int. Ed.*, 2013, 52: 2194-2197.

Jithunsa, Manita et al., "Copper(II)Chloride-Mediated Cyclization Reaction of *N*-Alkoxy-ortho-alkynylbenzamides." *Organic Letters*, 2011, 13(3): 518-521.

Kaiyawet, Nopporn et al., "Effect of Halogen Substitutions on dUMP to Stability of Thymidylate Synthase/dUMP/mTHF Ternary Complex Using Molecular Dynamics Simulation." *J. Chem. Inf. Model*, 2013, 53: 1315-1323.

Katritzky, Alan R. et al., "Mechanism of the Replacement of Phenolic Hydroxyl by Carbonyl on Lead Tetraacetate Treatment of *o*-Hydroxyaryl Ketone Acylhydrazones." *J. Org. Chem.*, 1991, 56: 5049-5051.

Katritzky, Alan R. et al., "Synthesis of o-Acylarylcarboxylic Esters: A New Replacement of Phenolic Hydroxyl by a Carbonyl Group." *Tetrahedron Letters*, 1990, 31(47): 6781-6784.

Koebrich, Gert et al., "Nachweis und Darstellung metallierter Nitroaromaten." *Chem. Ber.*, 1970, 103: 1412-1419.

Kong, Gyu Don et al., "Influence of halogem substitutions on rates of charge tunneling across SAM-based large-area junctions." *Phys. Chem. Chem. Phys.*, 2015, 17: 13804-13807.

Kotali, Antigoni et al., "Oxidation of N-Aroylhydrazones of o-Hydroxyaryl Ketones with Lead(IV) Acetate: A Facile Route to Aromatic o-Diketones." *Tetrahedron Letters*, 1987, 28(37): 4321-4322.

Kotali, Antigoni et al., "A novel and facile synthesis of 7,8-diacyclocoumarins." *Tetrahedron Letters*, 2007, 48: 7181-7183.

Kotali, Antigoni et al., "Transformation of a hydroxyl into an acyl group on α-pyrone ring: a novel route to 3,4-diacylcoumarins." *Tetrahedron*, 2012, 68: 761-766.

Kotali, Antigoni et al., "Oxidation of o-hydroxy arylketones N-acylhydrazones with sodium hypochlorite. ORGN 137." Abstracts of Papers of the American Chemical Society. vol. 230. 1155 16th St, NW, Washington, DC 20036 USA: Amer Chemical Soc, 2005.

Kotali, Antigoni etal., "Oxidation reactions of 7-hydroxy-8-acetylcoumarin oxime. ORGN 614." Abstracts of Papers of the American Chemical Society. vol. 230. 1155 16th St, NW, Washington, DC 20036 USA: Amer Chemical Soc, 2005.

Krasovskiy, Arkady et al., "Convenient Titration Method for Organometallic Zinc, Magnesium, and Lanthanide Reagents." *Synthesis*, 2006, 5: 890-891.

Kresge, C.T. et al., "Ordered mesoporous molecular sieves synthesized by a liquid-crystal template mechanism." *Nature*, Oct. 22, 1992, 359: 710-712.

Kumar, Sunil et al., "Polystyrene-Supported Iodobenzene Diacetate (PSIBD)—Mediated Synthesis of 1,2-Diacylbenzenes from 2-Hydroxyaryl Aldehyde/Ketone Acylhydrazones." *Synthetic Communications*, 2008, 38: 3683-3699.

Li, Duo et al., "Synthesis and characterizations of conjugated copolymers containing benzo[f]isoindole-1,3-dione and diketopyrrolopyrrole units." *Polymer*, 2013, 54: 5543-5552.

Mansour, Tarek S. et al., "Nucleophilic Addition *versus* Metalation of 4- and 2-Methylpyridine studied by Multinuclear Magnetic Resonance Spectroscopy." *J. Chem. Soc. Perkin Trans. II*, 1985, 12: 2045-2048.

Moriarty, Robert M. et al., "Synthesis of 1,2-Diacylbenzenes from *o*-Hydroxyaryl Ketone Acylhydrazones Using [(Diacetoxy)iodo]benzene." *Synthesis*, Mar. 1993, 318-321.

Niwa, Takashi et al., "Palladium-Catalyzed Direct Arylation of Aryl(azaaryl)methanes with Aryl Halides Providing Triarylmethanes." *Organic Letters*, 2007, 9(12): 2373-2375.

O'Mahony, T.A.F. et al., "Reactions of Lead Tetra-acetate with Substituted Benzaldehyde 5-Phenyl-1,2,4-triazol-3-ylhydrazones." *J. Chem. Soc. Perkin Trans. II*, 1972, 1319-1323.

Puterbaugh, Walter H. et al., "Metalation of N-Methylbenzamide with Excess *n*-Butyllithium. Condensations with Electrophilic Compounds to Form ortho Derivatives. Cyclizations." *The Journal of Organic Chemistry*, 1964, 29(4): 853-856.

Renaud, Philippe et al., "Reaction of Dilithiated Carboxylic Acids with Iodine: Evidence for the Formation of a Radical Anion Intermediate." *J. Org. Chem.*, 1988, 53: 3745-3752.

Sapountzis, Ioannis et al., "Synthesis of Functionalized Nitroarylmagnesium Halides via an Iodine-Magnesium Exchange." *J. Org. Chem.*, 2005, 70: 2445-2454.

Scott, F.L. et al., "The Triazole Ring as a Neighbouring Group in Lead Tetraacetate Reactions." *Tetrahedron Letters*, 1970, 21: 1841-1844.

Spears, C. Paul, "Nucleophilic Selectivity Ratios of Model and Clinical Alkylating Agents by 4-(4'-Nitrobenzyl)pyridine Competition." *Molecular Pharmacology*, 1981, 19: 496-504.

Travis, Benjamin R. et al., "Facile Oxidation of Aldehydes to Acids and Ester with Oxone." *Organic Letters*, 2003, 5(7): 1031-1034.

(56) References Cited

OTHER PUBLICATIONS

Tucker, Charles E. et al., "Preparation of Highly Functionalized Magnesium, Zinc, and Copper Aryl and Alkenyl Organometallics via the Corresponding Organolithiums." *J. Am. Chem. Soc.*, 1992, 114: 3983-3985.

Ulrch, Gilles et al., "Synthesis of Bisisoindolomethene Dyes Bearing Anisole or Ethylthiophene Residues for Red and Near-IR Fluorescence." *Synlett*, 2007, 10: 1517-1520.

Ulrch, Gilles et al., "Chemistry at Boron: Synthesis and Properties of Red to Near-IR Fluorescent Dyes Based on Boron-Substitutes Diisoindolomethene Frameworks." *J. Org. Chem.*, 2011, 76: 4489-4505.

Wender, Paul A. et al., "Function-Oriented Synthesis, Step Economy, and Drug Design." *Acc. Chem. Res.*, Jan. 2008, 41(1): 40-49.

Wibaut, J.P. et al., "Synthesis with rthe Aid of γ-Picolyllithium I: Preparation of 4-alkylpyridines." *Recueil des Travaux Chimiques des Pays-Bas*, 1953, 72(6): 513-521.

Wiriyachitra, Pichaet et al., "Organotellurium Chemistry. 3. (o-Nitrophenyl)tellurenyl Bromide: A Highly Stabilized Tellurenyl Halide." *J. Org. Chem.*, 1979, 44(22): 3957-3959.

Wirnsberger, Gernot etal., "pH Sensing with mesoporous thin films." *Chemical Communications*, 2001, 119-120.

Wu, George G. et al., "A Novel Iodide-Catalyzed Reduction of Nitroarenes and Aryl Ketones with $H_3PO_2$ or $H_3PO_3$: Its Application to the Synthesis of a Potential Anticancer Agent." *Organic Letters*, 2011, 13(19): 5220-5223.

Zhang, Qingmin et al., "A Condensable Amphiphile with a Cleavable Tail as a "Lizard" Template for the Sol-Gel Synthesis of Functionalized Mesoporous Silica." *J. Am. Chem. Soc.*, 2004, 126: 988-989.

\* cited by examiner

COMPOUNDS AND COMPOSITIONS FOR USE AS ALKYLATING AGENT SENSORS AND METHODS OF USE THEREOF

CROSS REFERENCE TO RELATED APPLICATION

This application claims priority from U.S. Provisional Application Ser. No. 62/076,819, filed 7 Nov. 2014.

TECHNICAL FIELD

This invention relates to compounds and compositions, their uses as sensors and methods for detecting mutagenic and/or carcinogenic agents. In particular the invention relates to compounds and compositions, and methods for their use as alkylating agent sensors.

BACKGROUND

Alkylating agents are broadly used as active pharmaceutical ingredients (APIs), agrochemicals, in industrial and laboratory settings, and also as chemical warfare agents. Alkylating agents can be highly mutagenic and/or carcinogenic because they form covalent bonds with endogenous compounds like DNA, proteins and other nucleophilic biomolecules. While alkylating agents have the potential to be toxic, the covalent modification of biomolecules can be a powerful treatment for a wide variety of maladies, from headaches to cancer.

Some chemotherapy drugs are very powerful alkylating agents. Nevertheless, the curative properties of chemotherapy drugs outweigh their carcinogenicity and mutagenicity for many cancer patients. However, exposure to non-patients is unacceptable. The highest risk groups are healthcare workers who may be chronically exposed to antineoplastic drugs throughout the course of their duties. Occupational exposure to chemotherapy drugs leads to skin rashes, liver toxicity, adverse reproductive outcomes, leukemia and cancer. In 2004, the National Institute for Occupational Safety and Health (NIOSH) reported that the number of exposed healthcare workers may exceed 5.5 million in the United States, and from this statistic it may be estimated that over half a million workers in Canada may be similarly compromised. Current cleaning protocols for antineoplastic drug spills may result in spreading the contamination over a larger area rather than cleaning of the spill.

4-(4-nitrobenzyl)pyridine or NBP (CAS No. 1083-48-3) is commonly used in testing for alkylating agents as a colorimetric indicator compound. NBP is used in toxicology screening of pharmaceutical compounds, detection of chemical warfare agents, environmental hygiene technology, and in other chemical analyses. The use in determining toxicology profiles and mutagenicity of medicinal compounds is due to NBP's reactive similarity to guanine.

NBP was first applied towards the detection of mustard gas agents by the Koenigs et al in 1925 (Koenigs, E., Kohler, K., and Blindow, K. Ber. Dtsch. Chem. Ges. 1925 58, 933-940). Later, Epstein increased the NBP method's accuracy and used it for quantitative determinations, and so often NBP is referred to as the "Epstein reagent" (Epstein, J.; Rosenthal, R. W.; Ess, R. J. Anal. Chem. 1955, 27, 1435-1439). The suggested mechanism follows an $SN_2$ displacement of a halide by the nucleophilic pyridine, as shown from conversion from I to II in acetone/water. Upon addition of base like triethylamine or NaOH, one of the acidic methylene protons is removed, effectively yielding the carbanion III (Dierickx, K.; et al. Talanta 2009, 77, 1370-1375).

SUMMARY

This invention is based in part on the fortuitous discovery that compounds and compositions described herein are useful as colorimetric indicators for many types of carcinogenic alkylating agents.

In accordance with a first aspect, there is provided a compound of Formula 1:

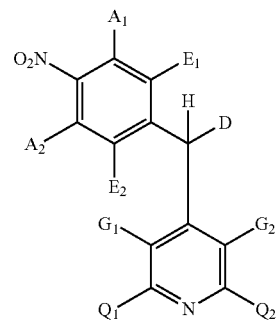

Formula 1, wherein $A_1$ may be selected from H, Me, Et, Pr, Bu, F, Br, I, OH, OJ, OC(O)J, $CF_3$, $CCl_3$, CN, $SO_3H$, C(O)OH, CHO, C(O)OJ, COJ, C(O)OK, C(O)$NJ_2$, C(O)N(J)(H), C(NJ)J, C(S)$NH_2$, C(S)$NJ_2$ and C(S)N(J)(H); $A_2$ may be selected from H, Me, Et, Pr, Bu, F, Br, I, OH, OJ, OC(O)J, $CF_3$, $CCl_3$, CN, $SO_3H$, C(O)OH, CHO, C(O)OJ, COJ, C(O)OK, C(O)$NJ_2$, C(O)N(J)(H), C(NJ)J, C(S)$NH_2$, C(S)$NJ_2$ and C(S)N(J)(H); $E_1$ may be selected from H, Me, Et, Pr, Bu, F, Br, I, OH, OL, OC(O)L, $CF_3$, $CCl_3$, CN, $SO_3H$, C(O)OH, CHO, $CH_2OH$, C(O)OL, COL, C(O)OK, C(O)$NL_2$, C(O)N(L)(H), C=NL, C(NL)L, C(S)$NH_2$, C(S)$NL_2$ and C(S)N(L)(H); $E_2$ may be selected from H, Me, Et, Pr, Bu, F, Br, I, OH, OL, OC(O)L, $CF_3$, $CCl_3$, CN, $SO_3H$, C(O)OH, CHO, $CH_2OH$, C(O)OL, COL, C(O)OK, C(O)$NL_2$, C(O)N(L)(H), C=NL, C(NL)L, C(S)$NH_2$, C(S)$NL_2$ and C(S)N(L)(H); D may be selected from H, Et, n-Pr, c-Pr, Bu, Cl, Br, I, $OT^b$, $OC(O)T^b$, $NO_2$, $CF_3$, $CCl_3$, CN, $SO_3H$, C(O)OH, CHO, $C(O)OT^a$, $COT^b$, C(O)OK, $C(O)NT^b{}_2$, $C(O)N(T^b)(H)$, $C(NT^b)T^b$, C(S)$NH_2$, $C(S)NT^b{}_2$ and $C(S)N(T^b)(H)$; $G_1$ may be selected from H, Et, Pr, Bu, F, Cl, Br, I, OH, $OM^a$, $OC(O)M^a$, $NO_2$, $CF_3$, $CCl_3$, CN, $SO_3H$, C(O)OH, CHO, $C(O)OM^a$, $COM^a$, C(O)OK, $C(O)NM^a{}_2$, $C(O)N(M^a)(H)$, $C(NM^a)M^a$, C(S)$NH_2$, $C(S)NM^a{}_2$ and $C(S)N(M^a)(H)$; $G_2$ may be selected from H, Et, Pr, Bu, F, Cl, Br, I, OH, $OM^a$, $OC(O)M^a$, $NO_2$, $CF_3$, $CCl_3$, CN, $SO_3H$, C(O)OH, CHO, $C(O)OM^a$, $COM^a$, C(O)OK, $C(O)NM^a{}_2$, $C(O)N(M^a)(H)$, $C(NM^a)M^a$, C(S)$NH_2$, $C(S)NM^a{}_2$ and $C(S)N(M^a)(H)$; $Q_1$ may be selected from H, Et, Pr, Bu, Br, I, OH, $OM^b$, $OC(O)M^b$, $NO_2$, $CCl_3$, $SO_3H$, C(O)OH, CHO, $C(O)OM^b$, $COM^b$, C(O)OK, $C(O)NM^c{}_2$, $C(O)N(M^d)(H)$, and $C(NM^b)M^b$; $Q_2$ may be selected from H, Et, Pr, Bu, Br, I, OH, $OM^b$, $OC(O)M^b$, $NO_2$, $CCl_3$, $SO_3H$, C(O)OH, CHO, $C(O)OM^b$, $COM^b$, C(O)OK, $C(O)NM^c{}_2$, $C(O)N(M^d)(H)$, and $C(NM^b)M^b$; provided that at least one of $A_1$, $A_2$, $E_1$, $E_2$, D, $G_1$, $G_2$, $Q_1$ and $Q_2$ is other than H; J may be independently selected from a 1-20 carbon alkyl, 1-20 carbon aryl or 1-20 carbon alkenyl group, optionally substituted with one or more of: =O, =S, OH, SH, $NH_2$, I, Br, Cl, F, CN, C(O)OH, CHO, $C(O)NH_2$, C(O)SH, $NO_2$, or $SO_3H$; L may be independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H; T$^a$ may be independently selected from a 1, or 3-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, COSH, NO$_2$, or SO$_3$H; T$^b$ may be independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H; M$^a$ may be independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H; M$^b$ may be independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H; and M$^c$ may be independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H; and M$^d$ may be independently selected from a 2-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H.

In accordance with a further aspect, there is provided a compound of Formula 1:

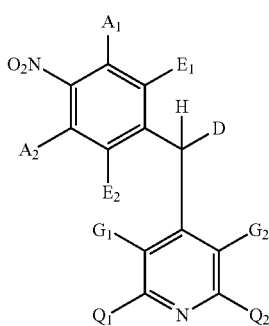

Formula 1, wherein A$_1$ may be selected from H, Me, Et, Pr, Bu, F, Cl, Br, I, OH, OR$^A$, OC(O)R$^A$, NO$_2$, CF$_3$, CCl$_3$, CN, SO$_3$H, CHO, CH$_2$OH, C(O)OR$^A$, COR$^A$, C(O)OK, C(O)NR$^A{}_2$, C(O)N(R$^A$)(H), C=NR$^A$, C(NR)R$^A$, C(S)NH$_2$, C(S)NR$^A{}_2$, C(S)N(R$^A$)(H),

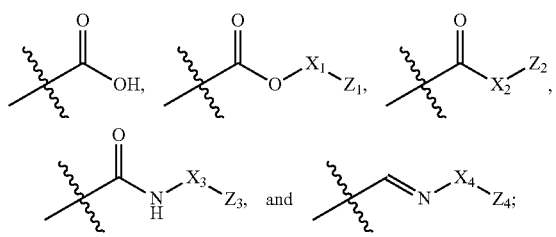

A$_2$ may be selected from H, Me, Et, Pr, Bu, F, Cl, Br, I, OH, OR$^A$, OC(O)R$^A$, NO$_2$, CF$_3$, CCl$_3$, CN, SO$_3$H, CHO, CH$_2$OH, C(O)OR$^A$, COR$^A$, C(O)OK, C(O)NR$^A{}_2$, C(O)N(R$^A$)(H), C=NR$^A$, C(NR)R$^A$, C(S)NH$_2$, C(S)NR$^A{}_2$, C(S)N(R$^A$)(H),

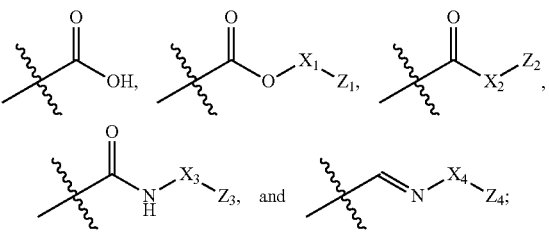

E$_1$, may be selected from H, Me, Et, Pr, Bu, F, Cl, Br, I, OH, OR$^E$, OC(O)R$^E$, NO$_2$, CF$_3$, CCl$_3$, CN, SO$_3$H, CHO, CH$_2$OH, C(O)OR$^E$, COR$^E$, C(O)OK, C(O)NR$^E{}_2$, C(O)N(R$^E$)(H), C=NR$^E$, C(NR$^E$)R$^E$, C(S)NH$_2$, C(S)NR$^E{}_2$, C(S)N(R$^E$)(H),

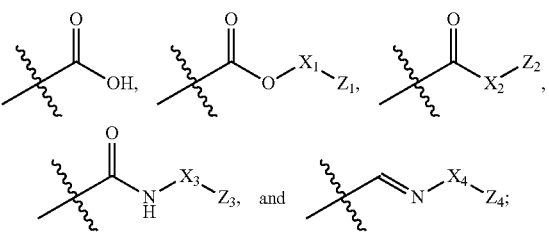

E$_2$ may be selected from H, Me, Et, Pr, Bu, F, Cl, Br, I, OH, OR$^E$, OC(O)R$^E$, NO$_2$, CF$_3$, CCl$_3$, CN, SO$_3$H, CHO, CH$_2$OH, C(O)OR$^E$, COR$^E$, C(O)OK, C(O)NR$^E{}_2$, C(O)N(R$^E$)(H), C=NR$^E$, C(NR$^E$)R$^E$, C(S)NH$_2$, C(S)NR$^E{}_2$, C(S)N(R$^E$)(H),

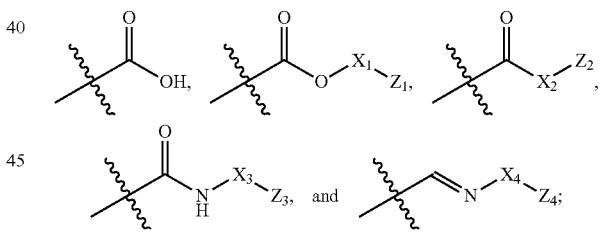

D may be selected from H, Me, Et, Pr, Bu, F, Cl, Br, I, OH, OR$^D$, OC(O)R$^D$, NO$_2$, CF$_3$, CCl$_3$, CN, SO$_3$H, CHO, CH$_2$OH, COOR$^D$, COR$^D$, C(O)OK, C(O)NR$^D{}_2$, C(O)N(R$^D$)(H), C=NR$^D$, C(NR$^D$)R$^D$, C(S)NH$_2$, C(S)NR$^D{}_2$, C(S)N(R$^D$)(H),

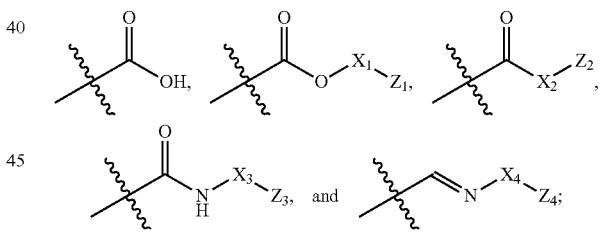

G$_1$ may be selected from H, Me, Et, Pr, Bu, F, Cl, Br, I, OH, OR$^G$, OC(O)R$^G$, NO$_2$, CF$_3$, CCl$_3$, CN, SO$_3$H, CHO, CH₂OH, C(O)OR$^G$, COR$^G$, C(O)OK, C(O)NR$^G$₂, C(O)N(R$^G$)(H), C=NR$^G$, C(NR$^G$)R$^G$, C(S)NH₂, C(S)NR$^G$₂, C(S)N(R$^G$)(H),

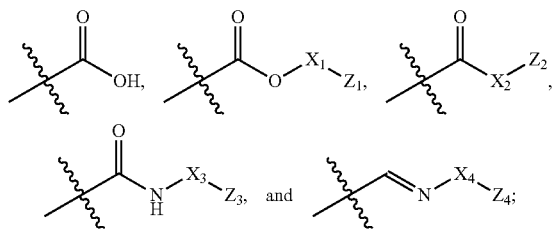

G₂ may be selected from H, Me, Et, Pr, Bu, F, Cl, Br, I, OH, OR$^G$, OC(O)R$^G$, NO₂, CF₃, CCl₃, CN, SO₃H, CHO, CH₂OH, C(O)OR$^G$, COR$^G$, C(O)OK, C(O)NR$^G$₂, C(O)N(R$^G$)(H), C=NR$^G$, C(NR$^G$)R$^G$, C(S)NH₂, C(S)NR$^G$₂, C(S)N(R$^G$)(H),

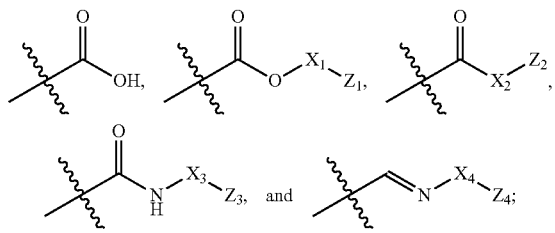

Q₁ may be selected from H, Me, Et, Pr, Bu, F, Cl, Br, I, OH, OR$^Q$, OC(O)R$^Q$, NO₂, CF₃, CCl₃, CN, SO₃H, CHO, CH₂OH, C(O)OR$^Q$, COR$^Q$, C(O)OK, C(O)NR$^Q$₂, C(O)N(R$^Q$)(H), C=NR$^Q$, C(NR$^Q$)R$^Q$, C(S)NH₂, C(S)NR$^Q$₂, C(S)N(R$^Q$)(H),

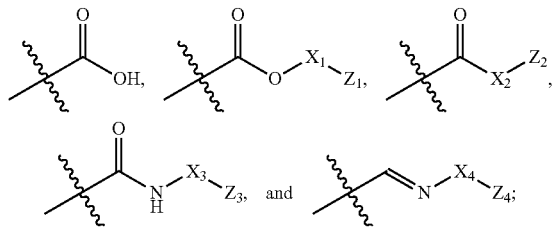

Q₂ may be selected from H, Me, Et, Pr, Bu, F, Cl, Br, I, OH, OR$^Q$, OC(O)R$^Q$, NO₂, CF₃, CCl₃, CN, SO₃H, CHO, CH₂OH, C(O)OR$^Q$, COR$^Q$, C(O)OK, C(O)NR$^Q$₂, C(O)N(R$^Q$)(H), C=NR$^Q$, C(NR$^Q$)R$^Q$, C(S)NH₂, C(S)NR$^Q$₂, C(S)N(R$^Q$)(H),

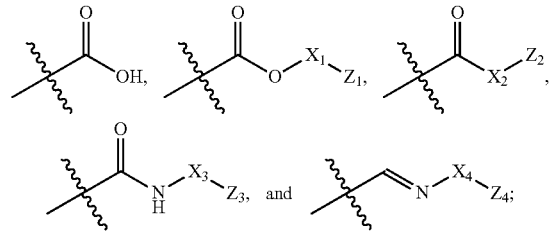

provided that at least one of A₁, A₂, E₁, E₂, D, G₁, G₂, Q₁, Q₂ is

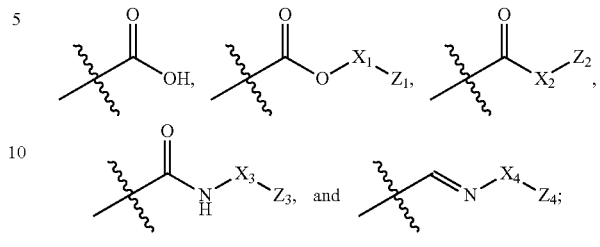

and wherein, X₁ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR₃; X₂ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR₃; X₃ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR₃; X₄ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR₃; Z₁ may be selected from SiR₃, Si(OR)₃, OH, NH, SH, aryl, C(O)OH, C(O)O⁻, NR₂, or NHR; Z₂ may be selected from SiR₃, Si(OR)₃, OH, NH, SH, aryl, C(O)OH, C(O)O⁻, NR₂, or NHR; Z₃ may be selected from SiR₃, Si(OR)₃, OH, NH, SH, aryl, C(O)OH, C(O)O⁻, NR₂, or NHR; Z₄ may be selected from SiR₃, Si(OR)₃, OH, NH, SH, aryl, C(O)OH, C(O)O⁻, NR₂, or NHR; R$^A$ may be a 1-20 carbon alkyl, 1-20 carbon aryl or 1-20 carbon alkenyl group, optionally substituted with one or more of: =O, =S, —OH, —SH, —NH₂, —I, Br, —Cl, —F, —CN, —C(O)OH, —CHO, —CONH₂, —COSH, —NO₂, or —SO₃H; R$^E$ may be a 1-20 carbon alkyl, 1-20 carbon aryl or 1-20 carbon alkenyl group, optionally substituted with one or more of: =O, =S, —OH, —SH, —NH₂, —I, Br, —Cl, —F, —CN, —C(O)OH, —CHO, —CONH₂, —COSH, —NO₂, or —SO₃H; R$^D$ may be a 1-20 carbon alkyl, 1-20 carbon aryl or 1-20 carbon alkenyl group, optionally substituted with one or more of: =O, =S, —OH, —SH, —NH₂, —I, Br, —Cl, —F, —CN, —C(O)OH, —CHO, —CONH₂, —COSH, —NO₂, or —SO₃H; R$^G$ may be a 1-20 carbon alkyl, 1-20 carbon aryl or 1-20 carbon alkenyl group, optionally substituted with one or more of: =O, =S, —OH, —SH, —NH₂, —I, Br, —Cl, —F, —CN, —C(O)OH, —CHO, —CONH₂, —COSH, —NO₂, or —SO₃H; R$^Q$ may be a 1-20 carbon alkyl, 1-20 carbon aryl or 1-20 carbon alkenyl group, optionally substituted with one or more of: =O, =S, —OH, —SH, —NH₂, —I, Br, —Cl, —F, —CN, —C(O)OH, —CHO, —CONH₂, —COSH, —NO₂, or —SO₃H; and R and R' are a 1-10 carbon alkyl or 1-10 carbon aryl, optionally substituted with one or more of: =O, =S, —OH, —SH, —NH₂, —I, Br, —Cl, —F, —CN, —C(O)OH, —CHO, —CONH₂, —COSH, —NO₂, or —SO₃H.

In accordance with a further aspect, there is provided a method for using a compound of Formula 1:

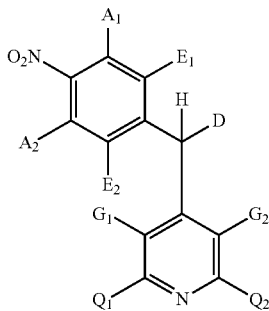

Formula 1, wherein $A_1$ may be selected from H, Me, Et, Pr, Bu, F, Cl, Br, I, OH, $OR^A$, $OC(O)R^A$, $NO_2$, $CF_3$, $CCl_3$, CN, $SO_3H$, CHO, $CH_2OH$, $C(O)OR^A$, $COR^A$, $C(O)OK$, $C(O)NR^A{}_2$, $C(O)N(R^A)(H)$, $C{=}NR^A$, $C(NR)R^A$, $C(S)NH_2$, $C(S)NR^A{}_2$, $C(S)N(R^A)(H)$,

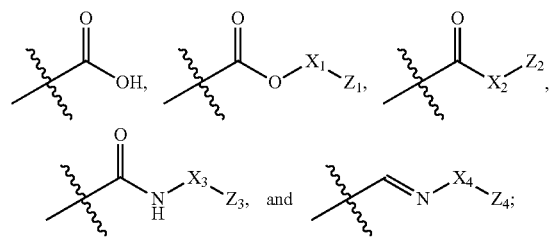

$A_2$ may be selected from H, Me, Et, Pr, Bu, F, Cl, Br, I, OH, $OR^A$, $OC(O)R^A$, $NO_2$, $CF_3$, $CCl_3$, CN, $SO_3H$, CHO, $CH_2OH$, $C(O)OR^A$, $COR^A$, $C(O)OK$, $C(O)NR^A{}_2$, $C(O)N(R^A)(H)$, $C{=}NR^A$, $C(NR)R^A$, $C(S)NH_2$, $C(S)NR^A{}_2$, $C(S)N(R^A)(H)$,

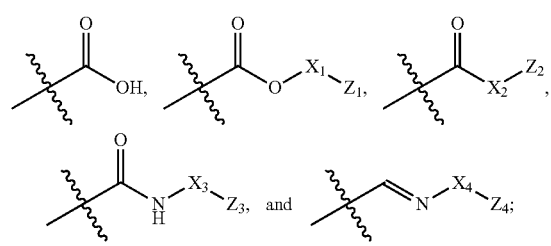

$E_1$ may be selected from H, Me, Et, Pr, Bu, F, Cl, Br, I, OH, $OR^E$, $OC(O)R^E$, $NO_2$, $CF_3$, $CCl_3$, CN, $SO_3H$, CHO, $CH_2OH$, $C(O)OR^E$, $COR^E$, $C(O)OK$, $C(O)NR^E{}_2$, $C(O)N(R^E)(H)$, $C{=}NR^E$, $C(NR^E)R^E$, $C(S)NH_2$, $C(S)NR^E{}_2$, $C(S)N(R^E)(H)$,

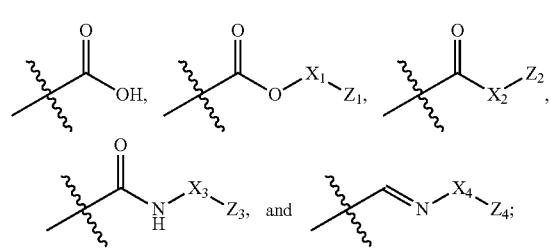

$E_2$ may be selected from H, Me, Et, Pr, Bu, F, Cl, Br, I, OH, $OR^E$, $OC(O)R^E$, $NO_2$, $CF_3$, $CCl_3$, CN, $SO_3H$, CHO, $CH_2OH$, $C(O)OR^E$, $COR^E$, $C(O)OK$, $C(O)NR^E{}_2$, $C(O)N(R^E)(H)$, $C{=}NR^E$, $C(NR^E)R^E$, $C(S)NH_2$, $C(S)NR^E{}_2$, $C(S)N(R^E)(H)$,

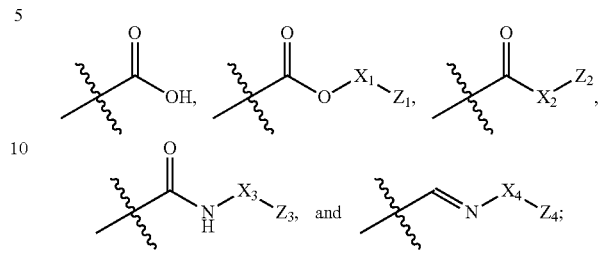

D may be selected from H, Me, Et, Pr, Bu, F, Cl, Br, I, OH, $OR^D$, $OC(O)R^D$, $NO_2$, $CF_3$, $CCl_3$, CN, $SO_3H$, CHO, $CH_2OH$, $COOR^D$, $COR^D$, $C(O)OK$, $C(O)NR^D{}_2$, $C(O)N(R^D)(H)$, $C{=}NR^D$, $C(NR^D)R^D$, $C(S)NH_2$, $C(S)NR^D{}_2$, $C(S)N(R^D)(H)$,

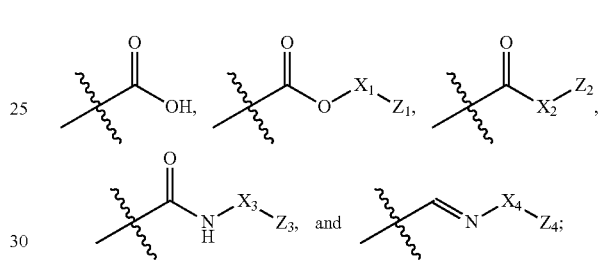

$G_1$ may be selected from H, Me, Et, Pr, Bu, F, Cl, Br, I, OH, $OR^G$, $OC(O)R^G$, $NO_2$, $CF_3$, $CCl_3$, CN, $SO_3H$, CHO, $CH_2OH$, $C(O)OR^G$, $COR^G$, $C(O)OK$, $C(O)NR^G{}_2$, $C(O)N(R^G)(H)$, $C{=}NR^G$, $C(NR^G)R^G$, $C(S)NH_2$, $C(S)NR^G{}_2$, $C(S)N(R^G)(H)$,

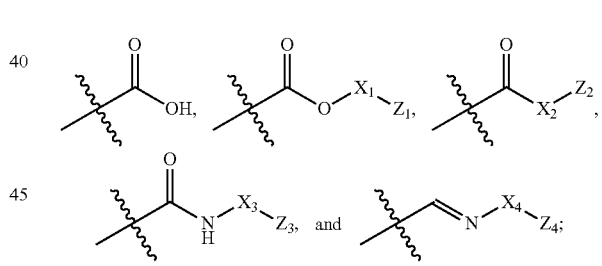

$G_2$ may be selected from H, Me, Et, Pr, Bu, F, Cl, Br, I, OH, $OR^G$, $OC(O)R^G$, $NO_2$, $CF_3$, $CCl_3$, CN, $SO_3H$, CHO, $CH_2OH$, $C(O)OR^G$, $COR^G$, $C(O)OK$, $C(O)NR^G{}_2$, $C(O)N(R^G)(H)$, $C{=}NR^G$, $C(NR^G)R^G$, $C(S)NH_2$, $C(S)NR^G{}_2$, $C(S)N(R^G)(H)$,

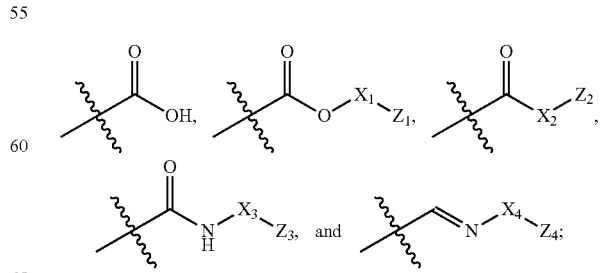

$Q_1$ may be selected from H, Me, Et, Pr, Bu, F, Cl, Br, I, OH, $OR^Q$, $OC(O)R^Q$, $NO_2$, $CF_3$, $CCl_3$, CN, $SO_3H$, CHO, CH$_2$OH, C(O)OR$^Q$, COR$^Q$, C(O)OK, C(O)NR$^Q_2$, C(O)N(R$^Q$)(H), C=NR$^Q$, C(NR$^Q$)R$^Q$, C(S)NH$_2$, C(S)NR$^Q_2$, C(S)N(R$^Q$)(H

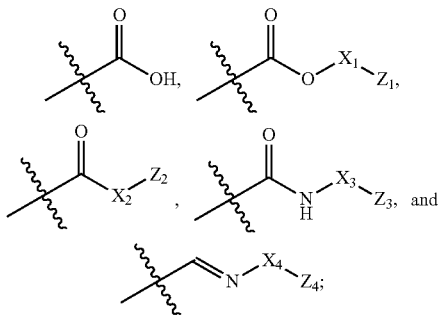

Q$_2$ may be selected from H, Me, Et, Pr, Bu, F, Cl, Br, I, OH, OR$^Q$, OC(O)R$^Q$, NO$_2$, CF$_3$, CCl$_3$, CN, SO$_3$H, CHO, CH$_2$OH, C(O)OR$^Q$, COR$^Q$, C(O)OK, C(O)NR$^Q_2$, C(O)N(R$^Q$)(H), C=NR$^Q$, C(NR$^Q$)R$^Q$, C(S)NH$_2$, C(S)NR$^Q_2$, C(S)N(R$^Q$)(H),

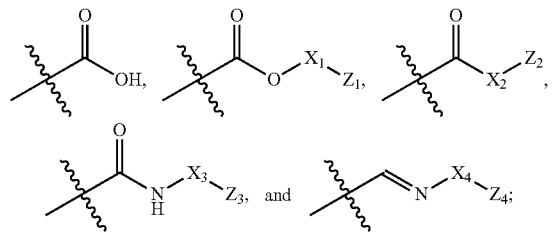

provided that at least one of $A_1$, $A_2$, $E_1$, $E_2$, D, $G_1$, $G_2$, $Q_1$, $Q_2$ is

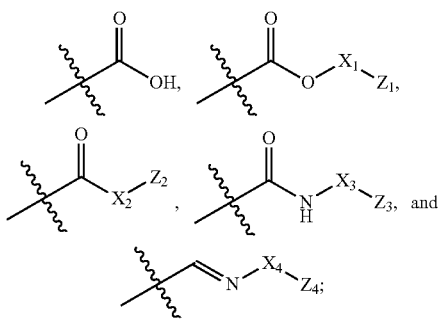

and wherein, $X_1$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR$_3$; $X_2$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR$_3$; $X_3$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR$_3$; $X_4$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or NR$_3$; $Z_1$ may be selected from SiR$_3$, Si(OR)$_3$, OH, NH, SH, aryl, C(O)OH, C(O)O$^-$, NR$_2$, or NHR; $Z_2$ may be selected from SiR$_3$, Si(OR)$_3$, OH, NH, SH, aryl, C(O)OH, C(O)O$^-$, NR$_2$, or NHR; $Z_3$ may be selected from SiR$_3$, Si(OR)$_3$, OH, NH, SH, aryl, C(O)OH, C(O)O$^-$, NR$_2$, or NHR; $Z_4$ may be selected from SiR$_3$, Si(OR)$_3$, OH, NH, SH, aryl, C(O)OH, C(O)O$^-$, NR$_2$, or NHR; R$^A$ may be a 1-20 carbon alkyl, 1-20 carbon aryl or 1-20 carbon alkenyl group, optionally substituted with one or more of: =O, =S, —OH, —SH, —NH$_2$, —I, Br, —Cl, —F, —CN, —C(O)OH, —CHO, —CONH$_2$, —COSH, —NO$_2$, or —SO$_3$H; R$^E$ may be a 1-20 carbon alkyl, 1-20 carbon aryl or 1-20 carbon alkenyl group, optionally substituted with one or more of: =O, =S, —OH, —SH, —NH$_2$, —I, Br, —Cl, —F, —CN, —C(O)OH, —CHO, —CONH$_2$, —COSH, —NO$_2$, or —SO$_3$H; R$^D$ may be a 1-20 carbon alkyl, 1-20 carbon aryl or 1-20 carbon alkenyl group, optionally substituted with one or more of: =O, =S, —OH, —SH, —NH$_2$, —I, Br, —Cl, —F, —CN, —C(O)OH, —CHO, —CONH$_2$, —COSH, —NO$_2$, or —SO$_3$H; R$^G$ may be a 1-20 carbon alkyl, 1-20 carbon aryl or 1-20 carbon alkenyl group, optionally substituted with one or more of: =O, =S, —OH, —SH, —NH$_2$, —I, Br, —Cl, —F, —CN, —C(O)OH, —CHO, —CONH$_2$, —COSH, —NO$_2$, or —SO$_3$H; R$^Q$ may be a 1-20 carbon alkyl, 1-20 carbon aryl or 1-20 carbon alkenyl group, optionally substituted with one or more of: =O, =S, —OH, —SH, —NH$_2$, —I, Br, —Cl, —F, —CN, —C(O)OH, —CHO, —CONH$_2$, —COSH, —NO$_2$, or —SO$_3$H; and R and R' are a 1-10 carbon alkyl or 1-10 carbon aryl, optionally substituted with one or more of: =O, =S, —OH, —SH, —NH$_2$, —I, Br, —Cl, —F, —CN, —C(O)OH, —CHO, —CONH$_2$, —COSH, —NO$_2$, or —SO$_3$H; as a colorimetric indicator for alkylating agents.

In accordance with a further aspect, there is provided a composition, the composition comprising (a) compound described herein and (b) a linker substrate, wherein the compound is bound to the linker substrate by

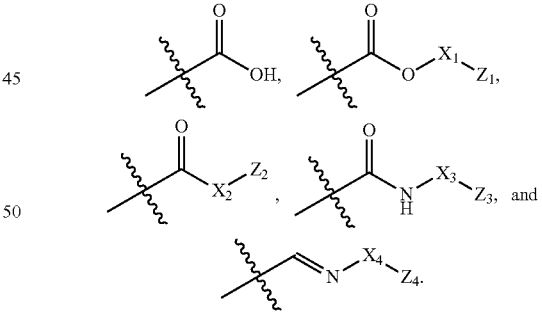

In accordance with a further aspect, there is provided a commercial package comprising the composition described herein, with instructions for use in detecting any alkylating agent.

In accordance with a further aspect, there is provided a method of synthesizing a 4-(4-nitrobenzyl)pyridine derivative, the method comprising synthetic methods described herein.

The compound of Formula I, wherein: $A_1$ is H; $A_2$ is H; $E_1$ may be selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL; $E_2$ may be selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL; D may be selected from H, Cl, Br, OC(O)T$^b$, NO$_2$, CF$_3$, CCl$_3$, CN, SO$_3$H, C(O)OH, CHO, C(O)OT$^a$, COT$^b$ and C(O)OK; G$_1$ may be selected from H, F, Cl, Br, I, NO$_2$, CF$_3$, CCl$_3$ and CN; G$_2$ may be selected from H, F, Cl, Br, I, NO$_2$, CF$_3$, CCl$_3$ and CN; Q$_1$ is H; and Q$_2$ is H; L may be independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H; T$^a$ may be independently selected from a 1, or 3-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H; and T$^b$ may be independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

The compound of Formula I, wherein: A$_1$ is H; A$_2$ is H; E$_1$ may be selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL; E$_2$ may be selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL; D is selected from H, Cl, Br, NO$_2$, CF$_3$, CCl$_3$, CN, SO$_3$H, C(O)OH and CHO; G$_1$ is H; G$_2$ is H; Q$_1$ is H; and Q$_2$ is H; and L is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

The compound of Formula I, wherein: A$_1$ is H; A$_2$ is H; E$_1$ may be selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL; E$_2$ may be selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL; D is H; G$_1$ is H; G$_2$ is H; Q$_1$ is H; and Q$_2$ is H; and L may be independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

The compound of Formula I, wherein: A$_1$ is H; A$_2$ is H; E$_1$ may be selected from H, CHO, CH$_2$OH, C(O)OL, C(O)OK, C(O)N(L)(H) and C=NL; E$_2$ may be selected from H, CHO, CH$_2$OH, C(O)OL, C(O)OK, C(O)N(L)(H) and C=NL; D is H; G$_1$ is H; G$_2$ is H; Q$_1$ is H; and Q$_2$ is H; and L may be independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

A, E, D, G and Q may also be C(O)ONa or C(O)OLi.

The compound may be selected from:

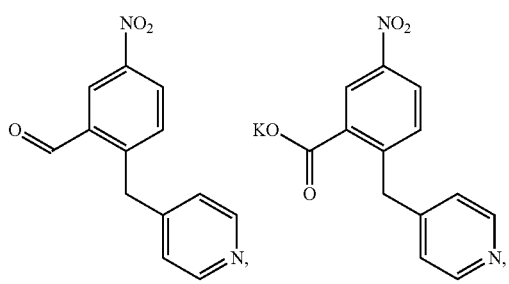

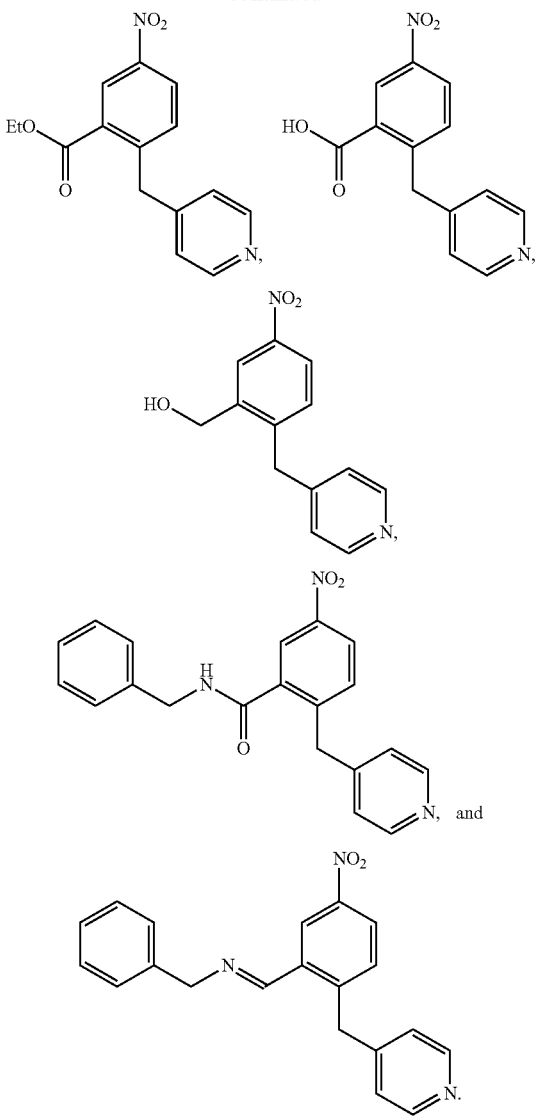

The compound of Formula I, wherein: A$_1$ is H; A$_2$ is H; E$_1$ may be selected from H, CH$_2$OH, CHO, C(O)OR$^E$, C(O)OK, C(O)N(R$^E$)(H), C=NR$^E$,

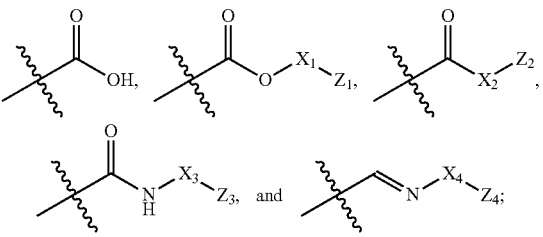

E$_2$ may be selected from H, CH$_2$OH, CHO, C(O)OR$^E$, C(O)OK, C(O)N(R$^E$)(H), C=NR$^E$,

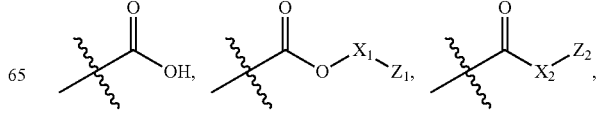

-continued

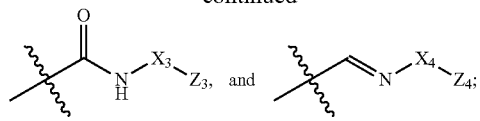

D is H; $G_1$ is H; $G_2$ is H; $Q_1$ is H; $Q_2$ is H; provided that at least one of $E_1$ or $E_2$ may be

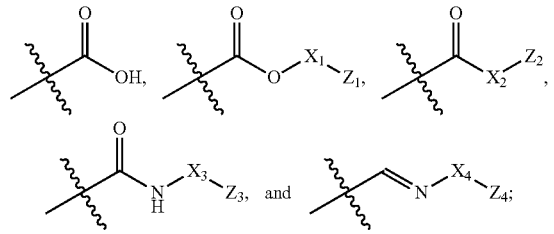

and wherein, $X_1$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or $NR_3$; $X_2$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or $NR_3$; $X_3$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or $NR_3$; $X_4$ may be a 1-20 carbon, saturated or unsaturated hydrocarbyl chain, or an ether group having the structure R—O—R', wherein the hydrocarbyl chain or the ether group may be optionally substituted by OH, F, Cl, Br, I, or $NR_3$; $Z_1$ may be selected from $SiR_3$, $Si(OR)_3$, OH, NH, SH, aryl, C(O)OH, C(O)O⁻, $NR_2$, or NHR; $Z_2$ may be selected from $SiR_3$, $Si(OR)_3$, OH, NH, SH, aryl, C(O)OH, C(O)O⁻, $NR_2$, or NHR; $Z_3$ may be selected from $SiR_3$, $Si(OR)_3$, OH, NH, SH, aryl, C(O)OH, C(O)O⁻, $NR_2$, or NHR; $Z_4$ may be selected from $SiR_3$, $Si(OR)_3$, OH, NH, SH, aryl, C(O)OH, C(O)O⁻, $NR_2$, or NHR; $R^E$ may be a 1-20 carbon alkyl, 1-20 carbon aryl or 1-20 carbon alkenyl group, optionally substituted with one or more of: =O, —OH, —SH, —$NH_2$, —CN, —C(O)OH, —CHO, —$CONH_2$ or —$SO_3H$; and R and R' are a 1-10 carbon alkyl or 1-10 carbon aryl, optionally substituted with one or more of: =O, —OH, —SH, —$NH_2$, —CN, —C(O)OH, —CHO, —$CONH_2$ or —$SO_3H$.

The compound may be selected from one or more of the following:

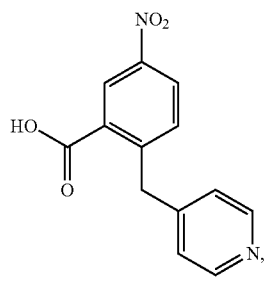

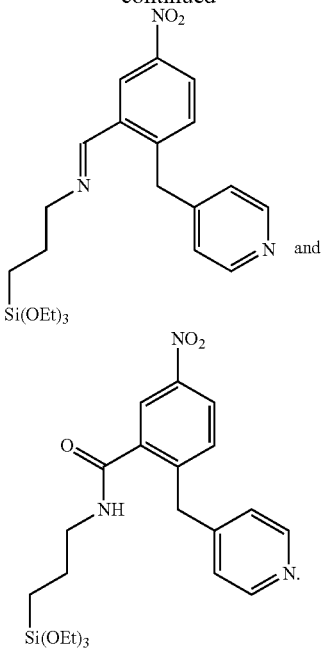

$Q_1$, or $Q_2$ may be selected from one or more of H, Me, Et, Pr, Bu, F, Cl, Br, I, OH, $OR^Q$, $OC(O)R^Q$, $NO_2$, $CF_3$, $CCl_3$, CN, $SO_3H$, CHO, $CH_2OH$, $C(O)OR^Q$, $COR^Q$, C(O)OK, $C(O)NR^Q_2$, $C(O)N(R^Q)(H)$, C=$NR^Q$, $C(NR^Q)R^Q$, C(S)$NH_2$, $C(S)NR^Q_2$, $C(S)N(R^Q)(H)$,

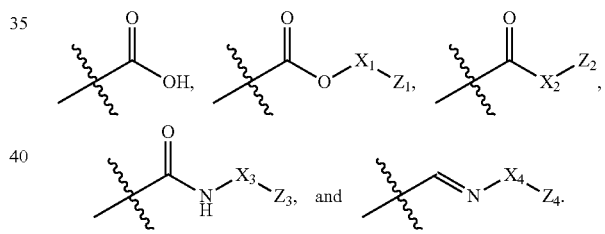

Generally, not interfering with or enhancing the nucleophilicity of the pyridine and maintaining or increasing the stability of the delocalized electrons in the conjugated system is a benefit to the alkylation activity. The Swain-Scott nucleophilicity constants for NBP and guanine are both 3-5, which probably accounts for the similar reactivity of NBP and guanine (Vogel, E. Mutation Research/Fundamental and Molecular Mechanisms of Mutagenesis 1994, 305, 13-32; and Spears, C. P. Molecular Pharmacology 1981, 19, 496-504). Since the nucleophilicity of the pyridine nitrogen in NBP and some of its derivatives so closely matches the nucleophilicity of the N7 position of guanine, it would be desirable to maintain the nucleophilicity of the pyridine. However, where substitutions are made to alter the NBP it may be desirable to increase the nucleophilicity of the pyridine nitrogen, whereby $Q_1$ or $Q_2$ or both may for example be Me, Et, Pr, Bu. Circumstances where you might want to change the nucleophilicity of the pyridine may depend on what the slow step is. If the slow step is alkylation, then adding electron donating groups like, Me, Et, Pr or Bu at $Q_1$ or $Q_2$ or both may be useful. However, if the deprotonation is the slow step, which is probably the case, then there would be no need to alter the nucleophilicity.

DETAILED DESCRIPTION

Definitions

Figure 1:
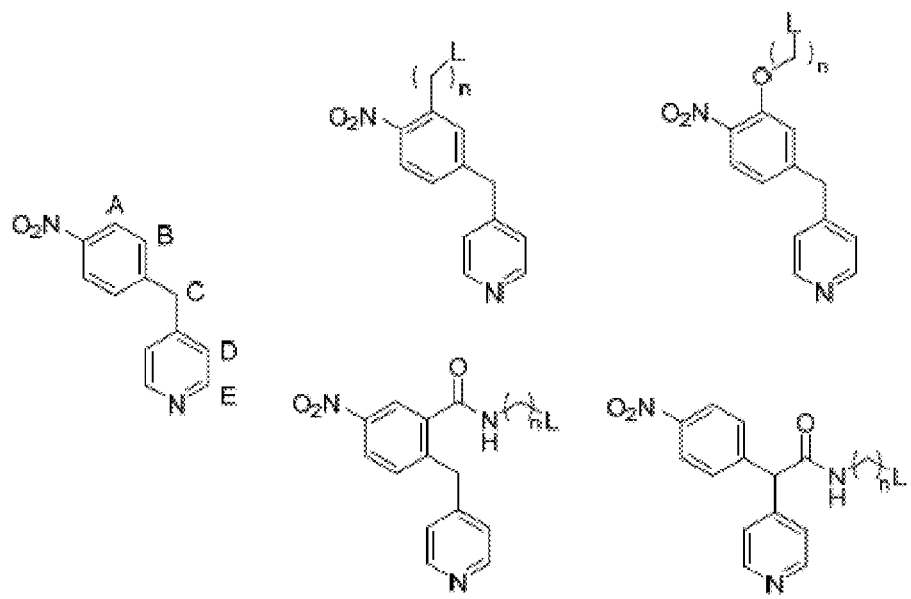
FIG. 1 shows some potential designs for an alkylating agent sensing molecule.
Figure 2:
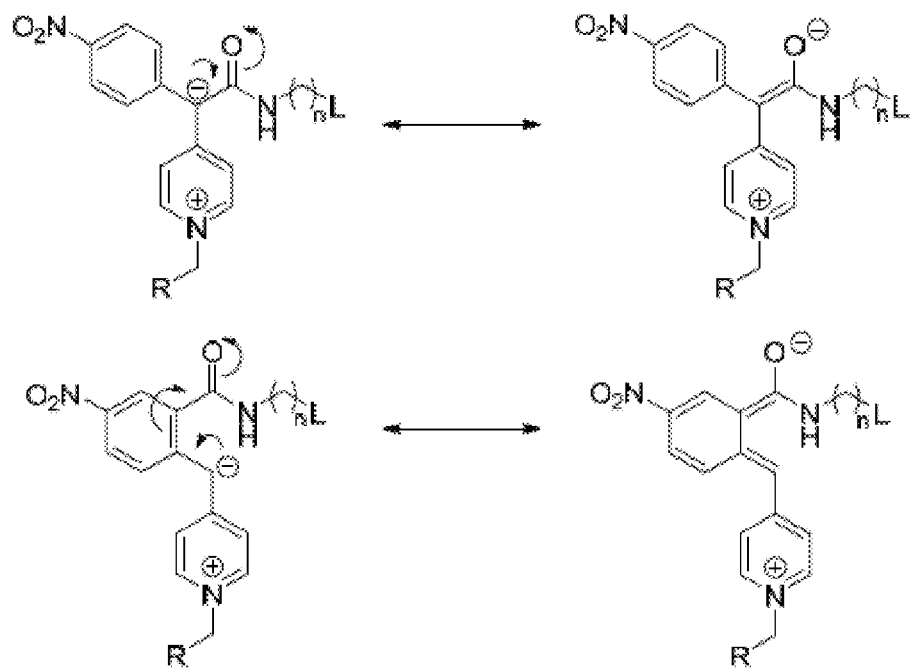
FIG. 2 shows stabilization of methine carbanions by an amide functionality.

As used herein an "ether group" is an oxygen atom connected to two alkyl or aryl groups and having the formula R—O—R'.

As used herein an "alkyl group" is a functional group or side-chain consists solely of single-bonded carbon and hydrogen atoms. However, the alkyls may be optionally substituted, such that one or more of the H atoms are replaced with a "substituent" as described herein.

As used herein an "aryl group" is any functional group or substituent derived from an aromatic ring. The group may be a phenyl, naphthyl, thienyl, indolyl, etc.

As used herein an "alkenyl group" is a hydrocarbon group having at least one carbon-carbon double bond.

As used herein a "hydrocarbyl" or "hydrocarbyl chain" is any univalent radical, derived from a hydrocarbon such as an "alkyl group", an "aryl group", "alkenyl group" etc.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, ability to undergo a colour change or ability to bind a substrate.

In some embodiments, compounds of Formula I or Formula II above may be used for systemic treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. In some embodiments compounds of Formula I or Formula II may be used in the preparation of a medicament or a composition for systemic treatment of an indication described herein. In some embodiments, methods of systemically treating any of the indications described herein are also provided.

Compounds as described herein may be in the free form or in the form of a salt thereof. A salt as used herein includes, for example, salts that have the desired activity of the parent compound (salts which retain the activity and/or properties of the parent compound and which are not colorimetrically undesirable). Compounds as described herein having one or more functional groups capable of forming a salt may be, for example, formed as a salt. Compounds containing one or more basic functional groups may be capable of forming a salt with, for example, an acceptable organic or inorganic acid. Possible salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming acceptable salts with an acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Acceptable salts may be derived from, for example, and without limitation, a hydroxide, carbonate, or bicarbonate of an acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glutamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

Figure 3:
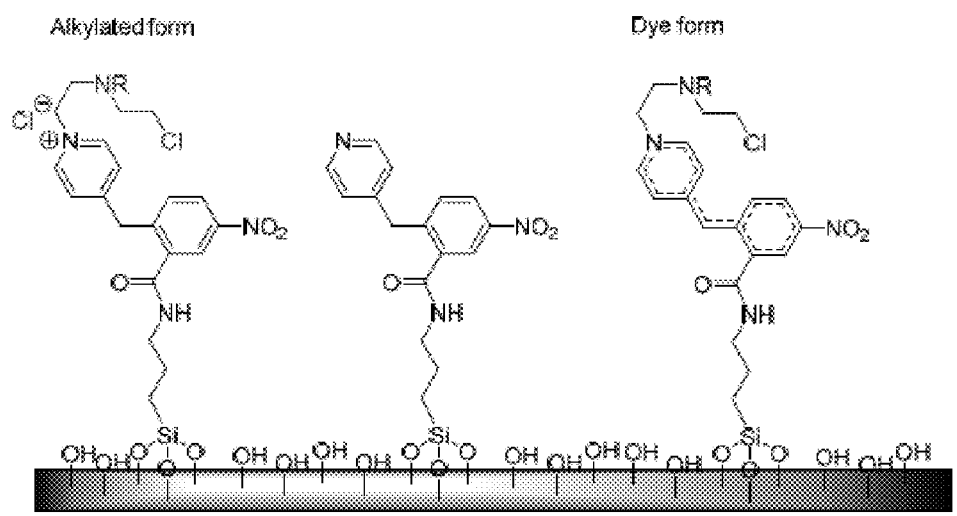
FIG. 3 shows proposed NBP/sol-gel based sensor for alkylating agents.

In some embodiments the compounds may form compositions, whereby the compound is bound to a linker substrate. Such a composition may comprise a part of a sensor. The linker substrate may be any material that permits the compound to be bound, most likely by the linker. The linker substrate may be a polymeric silica, (for example, sol-gel as shown in FIG. 3), may be an alternative polymeric substance that permits binding of the compound. The linker substrate may for part of a cloth, towel or wipe, which can change colour in response to the presence of an alkylating agent. Such a real time solid state sensor would be useful in cleaning spilled alkylating agents and to provide immediate feedback as to the success of the cleaning protocol. Alternatively, the linker substrate may be metal surface, PEGylate or an organic based polymer.

Alkylating Agent Sensors

Scheme 1: DNA-Single Walled Carbon Nanotube Sensor for Alkylating Agents

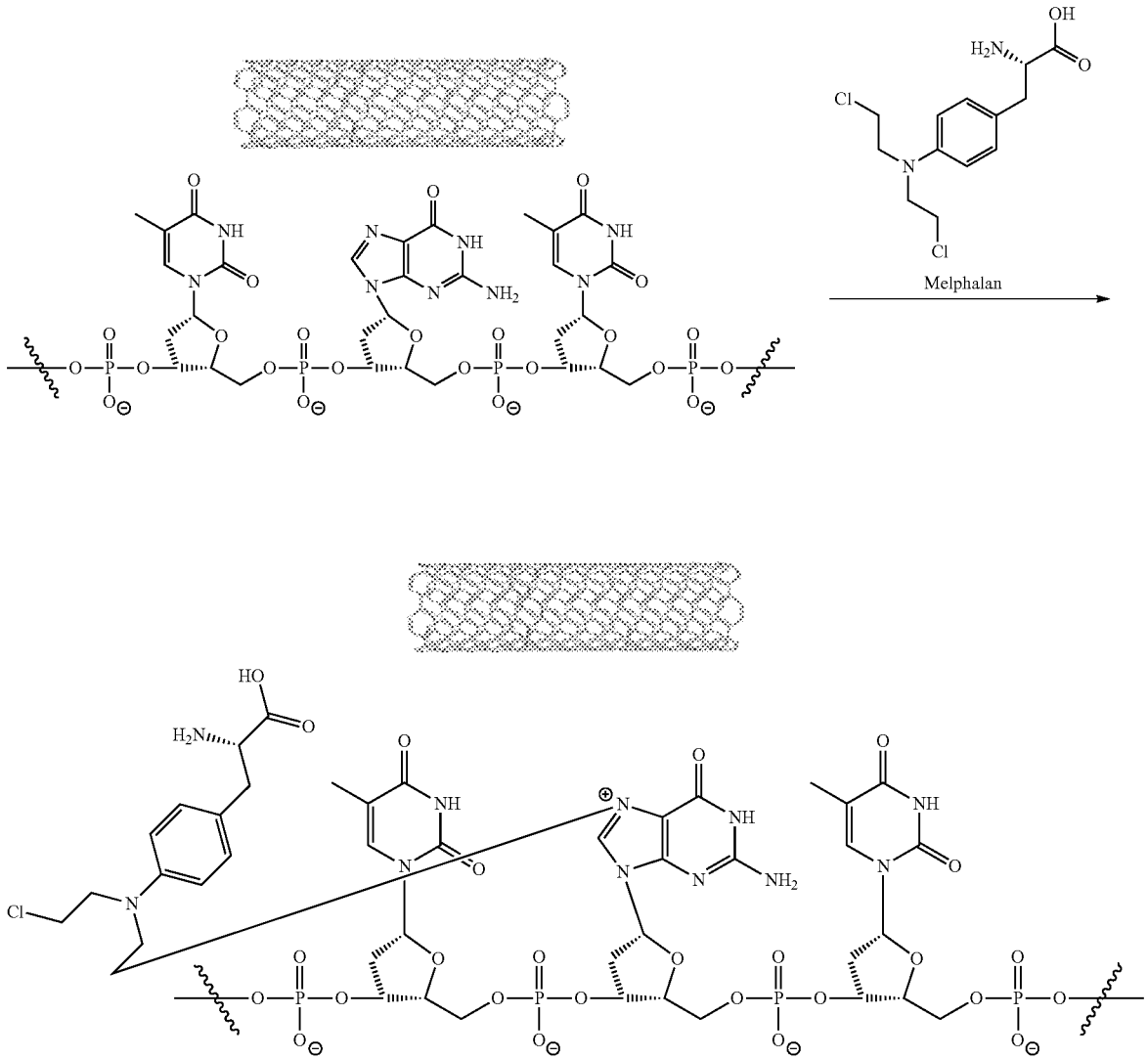

Michael Strano's group at MIT has used carbon nanotubes soaked in DNA solutions in the detection of alkylating agents (Heller, D. A. et al. Nat Nano 2009, 4, 114-120.). The researchers were able to observe the alkylation events by melphalan as changes in the near IR (NIR) spectrum of the carbon nanotube. While not truly feasible in a solid state sensor, this work from the Strano group demonstrates the viability of guanine as a sensor.

The Strano group reported that the guanine based sensor operates by detecting shifts in the photoluminescent spectra of (6,5) and (7,5) single walled carbon nanotubes, and they claimed that "single molecule detection" is possible by these biosensors.

At Rice University, the Weissman group has reported the theory behind "single molecule detection" with SWCNT, and have shown that stepwise fluorescence quenching is due to single molecular events (Cognet, L. et al. Science 2007, 316, 1465-1468), in order to view these events the sensor was exposed to 0.5 mM concentrations of the alkylating agent melphalan. Although this sensor works very well at millimolar concentrations, its use at sub-micromolar concentrations may not be feasible. Furthermore, in most circumstances, detection of "turn-on" signals rather than "turn-off" signals are preferred.

In 2006 the Eichen group reported a sensitive turn-on sensor for the detection of alkylating agents based on photoinduced electron transfer (Tal, S. et al. Chemistry—A European Journal 2006, 12, 4858-4864). The sensor is composed of a naphthalene imide (NI) core with a pendant nucleophilic amine. In the free, non-alkylated form the lone pair of the pendant nucleophilic amine quenches the natural fluorescence of the NI core, as depicted in Scheme 2. Upon alkylation, the amine lone pair lowers in energy and no longer interacts with the NI fluorophore, and then photoluminescence takes place, indicating the presence of the guest.

The Eichen group was able to obtain XRD crystal structures for the alkylated and dealkylated forms, and the conformation of the structures follows the cartoon picture, where the alkylated form exists in an "unfolded" state, and the non-alkylated form in a "folded" state. The sensor molecule may be impregnated into a filter that allows for the gas phase detection of alkylating agents, and the detection limit is in the micromolar range, so it is fairly sensitive. The major drawback for this sensor is that the sensor molecule responds in the same way towards acidic protons and metal ions as it does towards electrophiles.

The Eichen group solved the protonation issue by mixing base in with the alkylating agent analyte. They claim that metal ions can be distinguished by lowering the sample concentration and observing whether the sensing is in equilibrium, since sensing of alkylating agents occurs by covalent bond formation and metal ion sensing occurs in dynamic equilibrium, though they do not explain the practical method for distinguishing metal ions and alkylating agents in real sensing applications.

A number of groups have utilized Photoinduced-Electron-Transfer (PET) quenching towards an alkylating agent sensor. In 2005, the Rebek group presented a sensor for organophosphorus-based nerve agents like Sarin. The idea behind the PET sensing is very much like the Eichen group's sensor, but this sensor detects much more reactive and oxophilic phosphorus agents. As shown in Scheme 3 chlorophosphate reacts rapidly with the alcohol, which is in close proximity to the free amine, which displaces the diethylphosphate. A large array of fluorophores and linker lengths were tested to discover that a one methylene linker length between the amine and pyrene gave the greatest intensification of fluorescence on sensing (Dale, T. J. and Rebek, J. J. Am. Chem. Soc. 2006, 128, 4500-4501). They do not mention whether acids, metal ions or polar solvents impede the sensing, though the mechanism of sensing does not seem refractory to their interference.

Scheme 2: Mechanism for Photoinduced-Electron-Transfer (PET) Based Sensing of Alkylating Agents

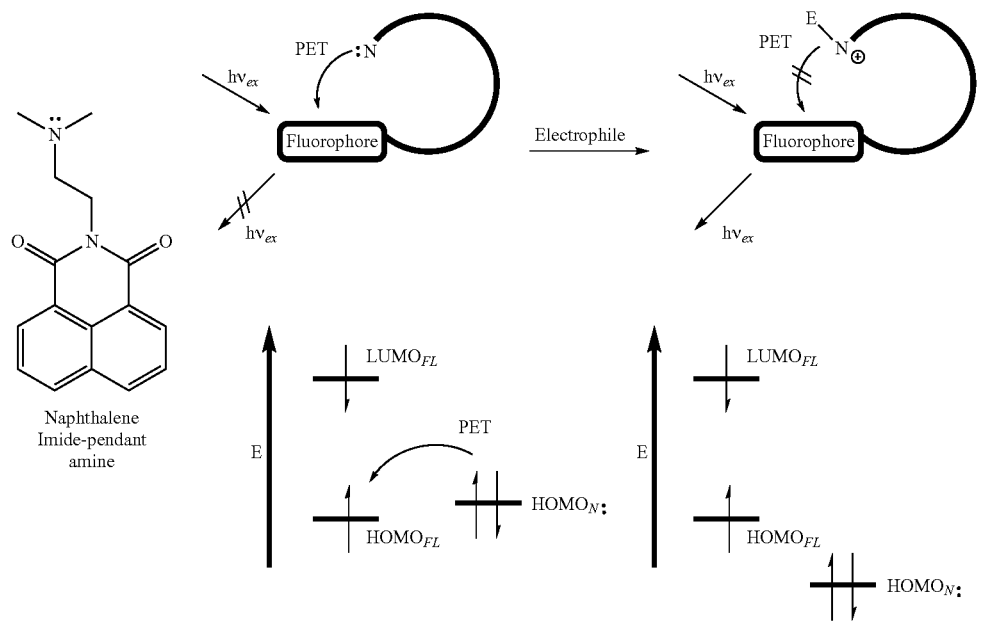

Scheme 3: PET Based Sensing of Organophosphorus Nerve Agents

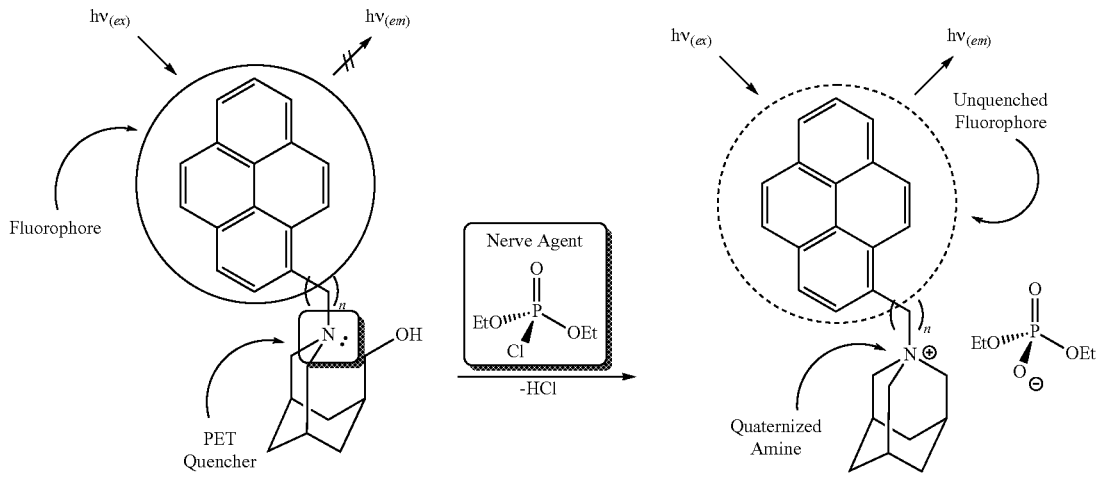

The Swager group from MIT also published a sensor for organophosphorus nerve agents. The sensor is comprised of a pyridine unit bound directly to a fluorophore with a nearby alcohol or silyl ether group. As seen in the Rebek sensor, activation of the oxygen functionality by organophosphorus nerve agent and quaternization of the pyridine nitrogen leads to a strong fluorescence. Interestingly, HCl produces a minimal fluorescence response in solution, but the sensing is appreciably interfered with when the compound is impregnated into cellulose acetate.

Scheme 4: Swager Group PET Sensing of Organophosphorus Nerve Agents

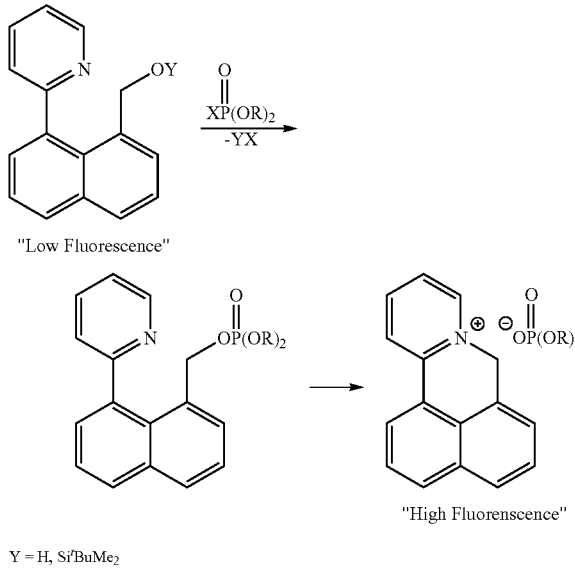

Y = H, Si$^t$BuMe$_2$

In 2008 the Smith group at Notre Dame reported a turn-on PET based sensor for micromolar levels of chloroalkanes, which utilizes both the alkylation of an amine and the complexation of the chloride ion as recognition for chloroalkanes (Lee, J.-J. et al. Org. Lett. 2008, 10, 1735-1738).

Scheme 5: Recognition of Alkyl Chlorides by a Macrocycle

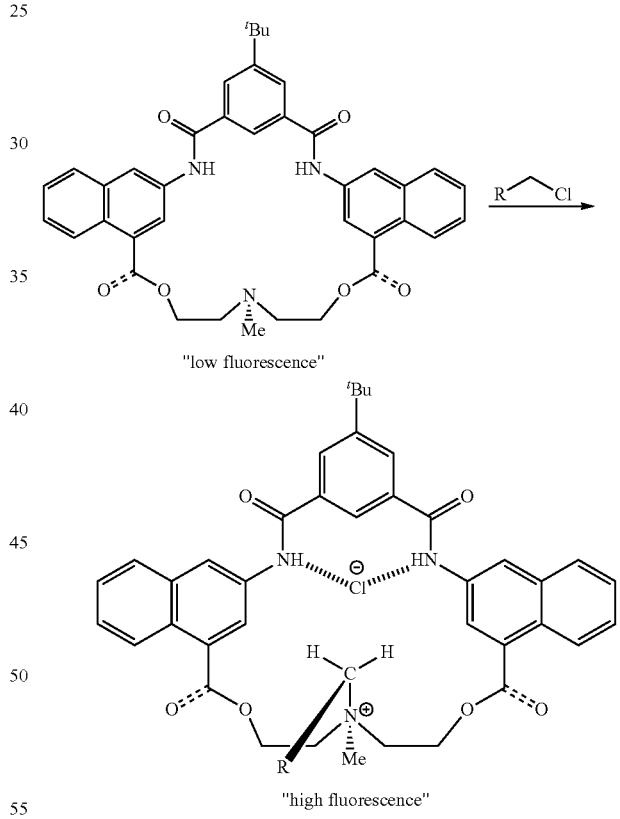

The macrocycle is a very powerful sensor for chloroalkanes, with the detection limit of chloromethyl methyl ether reported as low as 10 μM and the sensing very rapid, with a half-life of two minutes (Lee, J.-J.; et al. Am. Chem. Soc. 2005, 127, 4184-4185). The sensing mechanism operates by the alkylation of the free amine, which when non-alkylated quenches the fluorescence of the naphthalene. The sensor does not work with gas phase analytes. However, a device has been proposed, which allows for gas phase analytes to be drawn into a solution of the sensing molecule. Furthermore, the sensor does not respond as strongly towards alkyl iodides and bromides, even though they may be a more dangerous alkylating agent and a desirable analyte to detect (Stanger, K. J. et al. J. Org. Chem. 2007, 72, 9663-9668). Finally, a small presence of any polar solvent like water, methanol, DMSO or an acid like HCl shuts down the reactivity of the sensor, which is a significant drawback. Some effort was made to use the sensor in micellar solution in order to detect alkylating agents when polar solvent is around (Lee, J.-J. and Smith, B. D. Chemical Communications 2009, 1962-1963).

To determine the best way to incorporate NBP into a material, we examined the mechanism of dye formation. The suggested mechanism follows an $S_N2$ displacement of a halide by the nucleophilic pyridine, as shown from conversion from I to II in acetone/water. Upon addition of base like triethylamine or NaOH, one of the acidic methylene protons is removed, effectively yielding the carbanion III (Dierickx, K. et al. Talanta 2009, 77, 1370-1375).

Scheme 6: Mechanism of Dye Formation NBP and Alkylating Agents

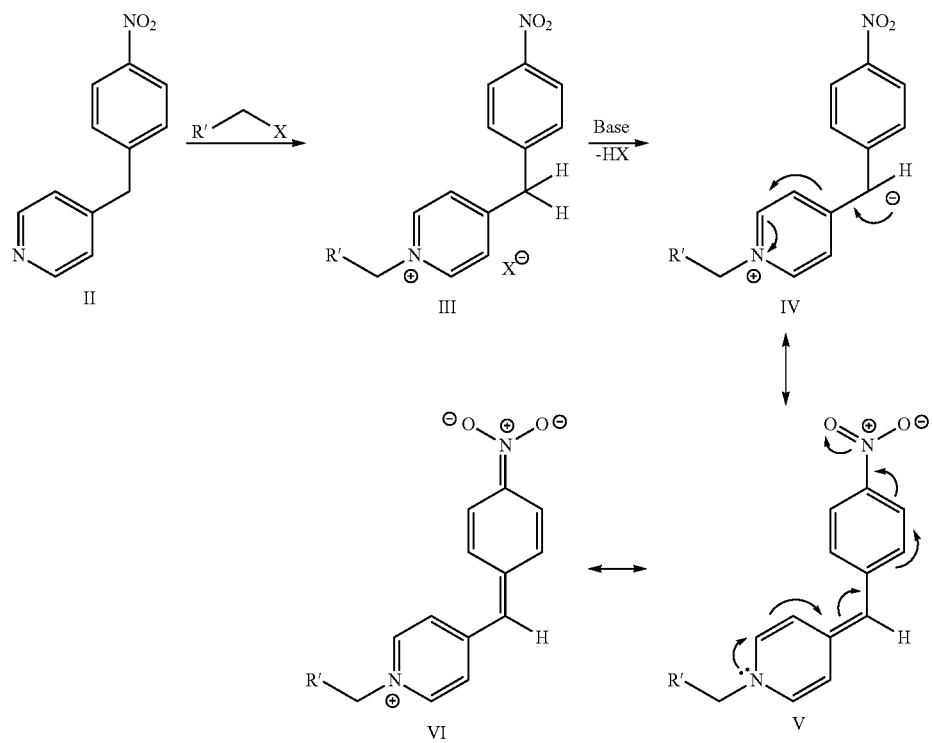

4-(4-nitrobenzyl)pyridine (NBP)

In the literature of alkylating agents, a number of references are made to the "NBP test" as a method for assessing the activity of alkylating agents and for the trace analysis of alkylating agents in environmental and biological sample. "NBP" is the shorthand for 4-(4-nitrobenzyl)pyridine, which is a colorimetric indicator for alkylating agents. NBP was first applied towards the detection of mustard gas agents by the Koenigs et al. in 1925 (Koenigs, E. et al. Ber. Dtsch. Chem. Ges. 1925 58, 933-940). Epstein increased the NBP method's accuracy and used it for quantitative determinations, and so often NBP is referred to as the "Epstein reagent" (Epstein, J. et al. Anal. Chem. 1955, 27, 1435-1439).

NBP may be grafted to a surface, where alkylations of NBP could be detected in some change of the bulk material.

NBP has been used to impregnate a material by simply soaking a porous cellulose tape in a solution of NBP and base. This composition has been found to be a good sensor for gaseous phosgene down to 6 ppb. However, the tape was found to be only sensitive to very reactive species like phosgene, but not benzyl chloride. Additionally, the monitoring tape was found to lose 10% activity after exposure to air for three months. The present research was intended to devise an improved molecule based on the NBP motif with greater range of reactivity, sensitivity, stability (both of the indicating dye and the initial compound), and similarity to biological systems.

As can be seen from the mechanism (Scheme 6), NBP is not sensitive towards acidic protons, because a subsequent basification is required, which would also deprotonate any protonated NBP. Furthermore, the conditions are very broad, not requiring very specific buffered conditions like guanine/DNA, and the sensing can take place in a wide variety of solvents. NBP provides the required function of guanine/DNA while minimizing complexity of the system, as analogous to function oriented synthesis (Wender, P. A. et al. Acc. Chem. Res. 2007, 41, 40-49).

With this understanding of the dye mechanism, NBP derivatives were designed that could link to a bulk material. Generally, it was hoped that the linker would be bound through the carbon network of the NBP scaffold, such that the linker would (1) not interfere with or enhance the nucleophilicity of the pyridine and would (2) maintain or increase the stability of the delocalized electrons in the conjugated system. Generally, it was thought that the nucleophilicity of the pyridine nitrogen should not be changed because the pyridine already so closely matches the nucleophilicity of the N7 position of guanine. Accordingly, substitution of the pyridine at the D or E positions as in Error! Reference source not found. (corresponding to positions $G_1/G_2$ and $Q_1/Q_2$ of Formula I) are a lower priority than substitutions at the B and C positions (referring to FIG. 1 and corresponding to positions $E_1/E_2$ and D in Formula I). The Swain-Scott nucleophilicity constants for NBP and guanine are both 3.5, which should account for the similar reactivity of NBP and guanine (Spears, C. P. Molecular Pharmacology 1981, 19, 496-504). Furthermore, due to the extensive research performed on the reactivity of NBP and protocols set for analysis of alkylating agents, it was hoped that the reactivity of the new compounds would be similar to NBP in order to match the already utilized relationships between NBP and alkylating agents.

In preparing a sensor molecule consistent with NBP applications and reactivity, it was thought that the positions for the linker would be A, B, or C (referring to FIG. 1 and corresponding to positions $A_1/A_2$, $E_1/E_2$ and D in Formula I) and whereby positions D and E (referring to FIG. 1 and corresponding to positions $G_1/G_2$ and $Q_1/Q_2$ in Formula I). In order to best lower the ground state energy of the anionoid dye structure, the linker was comprised of an electron-withdrawing functionality so it can further delocalize the free electrons. In the A position, an electron withdrawing group could only stabilize the carbanion through induction, while in the B and C positions an electron withdrawing group could also stabilize through resonance. When the linker is an amide (or ketone, ester, phosphonate, or other unsaturated electron withdrawing group) the dye form would benefit from greater resonance stability, it was thought that these could be promising targets. Additionally, a carbonyl functionality for installation of a linker molecule should allow for the facile testing of many types of linkers. The resonance structures of the anionoid chromophore structure are shown in Error! Reference source not found.

The strategy of stabilizing a chromophoric motif similar to the NBP mechanism (a so-called diarylmonomethine) with an electron withdrawing functionality was employed by the Detty group at the University at Buffalo (Bedics, M. A. et al. J. Org. Chem. 2013, 78, 8885-8891). The Detty group synthesized a number of chalcogenopyrylium monomethine dyes with pendant aryl phosphonates for the dual purpose of stabilizing the dye and enabling the binding of the molecule to nanocrystalline $TiO_2$ towards the synthesis of a dye sensitized solar cell.

While the phosphonic acid derivative was successful in its application to a dye sensitized solar cell, we thought that an amide would be a more facile synthetic target, and would enable the switching of linker molecule lengths and functionalities. Targeting an amide should also allow for the transformation into an ester or imine, so parallel or divergent oriented synthesis would be possible (Burke, M. D. and Schreiber, S. L. Angewandte Chemie International Edition 2004, 43, 46-58). While alkyl or alkoxy groups in the A position should also work, we thought they may not significantly stabilize the anianoid chromophore. Thus initial linker placements were in the B position as an amide, since an amide bond should be robust and have good versatility in synthesis of different linkers.

The linker could be any length organic fragment ending in a reactive functionality. Common reactive functionalities include trisalkoxysilanes, thiols, carboxylic acids, diazonium salts and others. Invariably, the choice of the reactive functionality should be determined by the material chosen for incorporation. Thiols are often chosen for the generation of functionalized gold thin films due to the strong gold-sulfur bond and useful electrical and physical properties of gold (Busse, S. et al. Sensors and Actuators B: Chemical 1999, 60, 148-154). Oxygen based functionalities like hydroxy, siloxy, and carboxy are often incorporated into silicas because of the high oxophilicity of silicon (Zhang, Q. et al. J. Am. Chem. Soc. 2004, 126, 988-989; and Green, W. H. et al. Science 1997, 276, 1826-1828). If the sensor was going to be based on the NBP sensor motif, the response should be colorimetric in nature, and so we thought an optically transparent material would be the best choice. Amorphous polymeric silica networks known as sol-gels have the potential to be transparent if they are amorphous, and indium tin oxide (ITO) has the dual advantage of being transparent and electrically conducting. An electrically conducting material would have good sensing properties, since small changes in the electrical properties of the material could be easily detected.

Scheme 7: Sol-Gel Formation

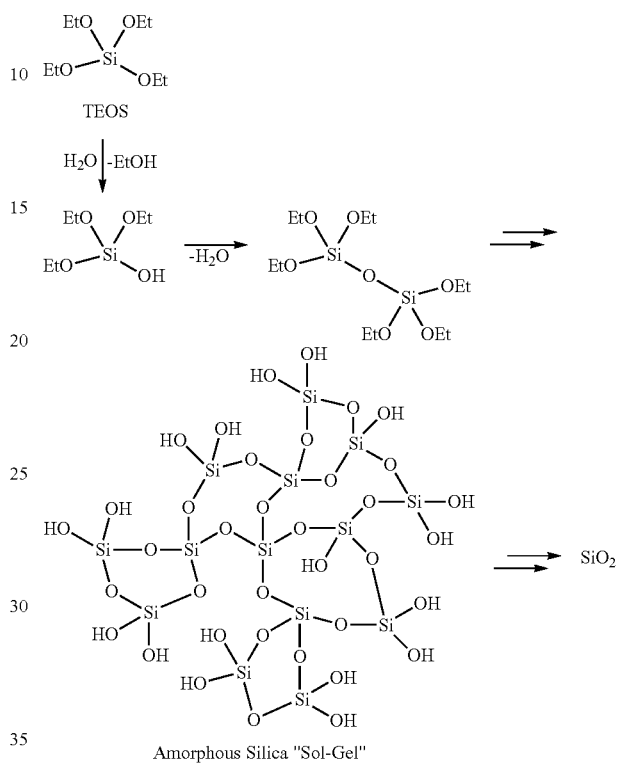

Amorphous Silica "Sol-Gel"

Sol-gels are amorphous silica films usually generated from acid or base hydrolysis of tetraalkylorthosilicates, with the most common starting material being tetraethylorthosilicate (TEOS) as shown in Scheme 7. Sol-gels have a few advantages as a sensor based material: (1) they are easily synthesized, (2) they can be mesoporous, which leads to rapid uptake of analytes, (3) they can have high surface area, offering many spots for a reaction to take place, and (4) they can facilitate proton transfers in the solid state (Kresge, C. T. et al. Nature 1992, 359, 710-712; and Wirnsberger, G. et al. Chemical Communications 2001, 119-120).

Scheme 8: Impregnation of Triethoxysilanes and Carboxylic Acids into a Sol-Gel

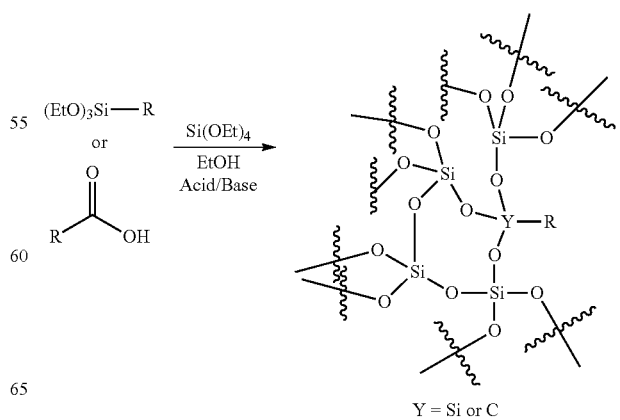

Y = Si or C

The incorporation of organic fragments into the polymeric silica network is facile: the organic fragment may be a carboxylic acid or organotrisalkoxysilane and is simply stirred with the orthosilicate over the course of hydrolysis as shown in Scheme 8.

Various alternative embodiments and examples of the invention are described herein. These embodiments and examples are illustrative and should not be construed as limiting the scope of the invention.

Materials and Methods

Cyclophosphamide (CP)

CP is used for the treatment of lymphoma, leukemias, multiple myeloma, mycosis fungoides, neuroblastoma, retinoblastoma, cancers of the breast and ovary, and some autoimmune diseases. CP was chosen as a model compound because it is one of the most potent and widely used chemotherapy drugs. CP is an alkylating agent in the "nitrogen mustard" category. The use of nitrogen mustards as chemotherapy drugs was first discovered in the 1940s by Louis S. Goodman and Alfred Gilman while studying chemical warfare reagents like sulfur mustard gas (Goodman, L. S. Journal of the American Medical Association 1946, 132, 126-132; and Gilman, A. The American Journal of Surgery 1963, 105, 574-578).

CP inhibits the replication of DNA, which targets cancer cells because they replicate so rapidly and with less error correcting. Targeting rapidly replicating cells is a classic method in many different chemotherapy drugs.

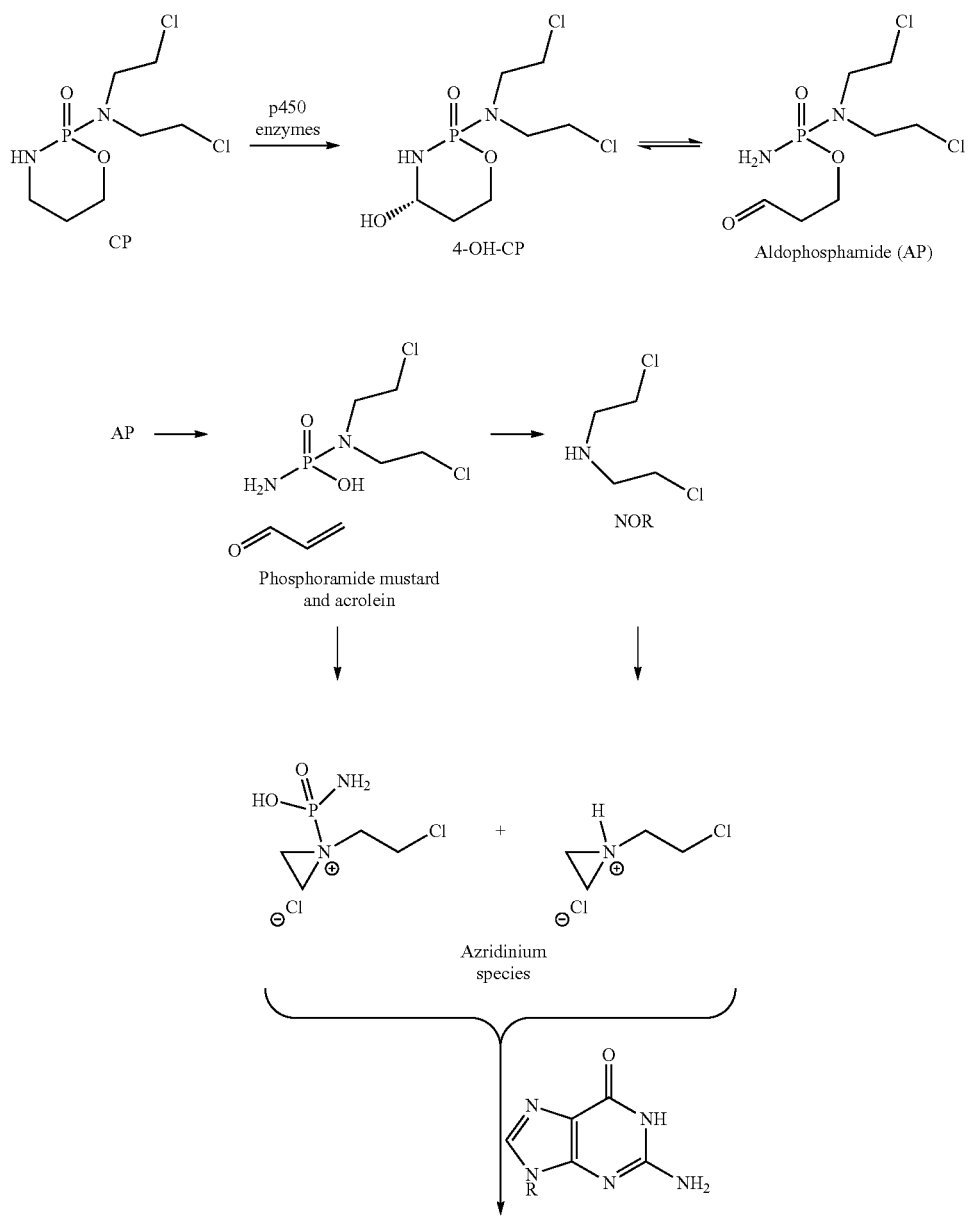

Scheme 9: Cyclophosphamide Mechanism of Action

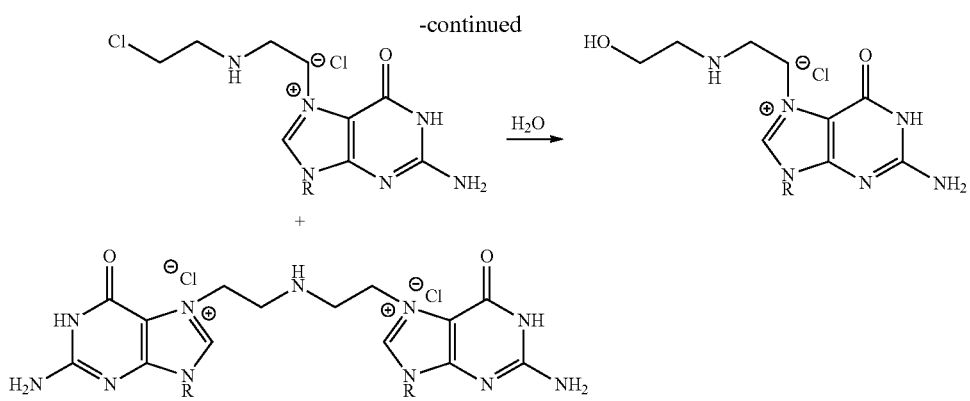

The active species of CP is phosphoramide mustard (PAM), which is generated through metabolism by p450 enzyme CYP2B6 (Johnson, L. A. et al. Pediatric Blood & Cancer 2012, 58, 708-714). Phosphoramide mustard may then be converted to NOR by hydrolysis, but both PAM and NOR may form highly reactive aziridinium intermediates which then alkylate guanine in DNA at the N7 position. After one alkylation event, the second chloroethyl group on the nitrogen mustard may activate to the aziridinium specie and alkylate other nearby DNA bases or hydrolyze to the hydroxyethyl specie. If the DNA base ordering follows GXC, then diagonal to an alkylated guanine is another reactive guanine nucleotide, since the complementary strand follows CXG. Previously the crosslink was predicted to occur at GC/CG where guanines would be directly diagonal and 7-8 Å apart, but later research has shown that cross-linking occurs across GXC/CXG sequences due to distortions in the DNA structure upon the first alkylation event (Osborne, M. R. et al. Chem. Res. Toxicol. 1995, 8, 316-320; Brookes, P. and Lawley, P. D. Biochem. J. 1961, 80, 496-503; Ojwang, J. O. et al. Cancer Research 1989, 49, 6529-6537; Hopkins, P. B. et al. Tetrahedron 1991, 47, 2475-2489). These crosslinks prevent DNA polymerase from copying DNA and may cause double strand breaks, and so can induce the onset of apoptosis (Becker, R. et al. British Journal of Cancer 2002, 86, 130-135). Bis-alkylating species are also much more cytotoxic because of their cross-linking ability. Additionally, the presence of acrolein, a metabolite of CP, in concert with DNA crosslinks has been shown to cause single strand scission, another factor in the genotoxicity of cyclophosphamide (Crook, T. R. et al. Cancer Research 1986, 46, 5029-5034).

Accordingly guanine was chosen as a target for the detection of cyclophosphamide due to its direct involvement with the genotoxicity of CP. Additionally, a guanine based material should be sensitive to a broad array of alkylating agents, since the N7 position is the most common center of alkylation in DNA.

In addition to CP, many chemotherapy drugs are alkylating agents that target guanine in DNA. There are a large array of nitrogen mustards like melphalan, chlorambucil, ifosfamide and bendamustine. These agents generally give similar alkylation yields at N7-G, but the major difference in their genotoxicity lies in the different levels of O6-G and O4-T alkylations. O-alkylations in DNA have been studied extensively since these events seem to give the greatest base mispairing.

Synthesis and Characterization of Compounds
Synthesis Introduction

Since one of the compositions of interest was an NBP/sol-gel based sensor for alkylating agents, synthetic plans were devised for the synthesis of NBP-Si, leading to a sensor material shown in Scheme 11.

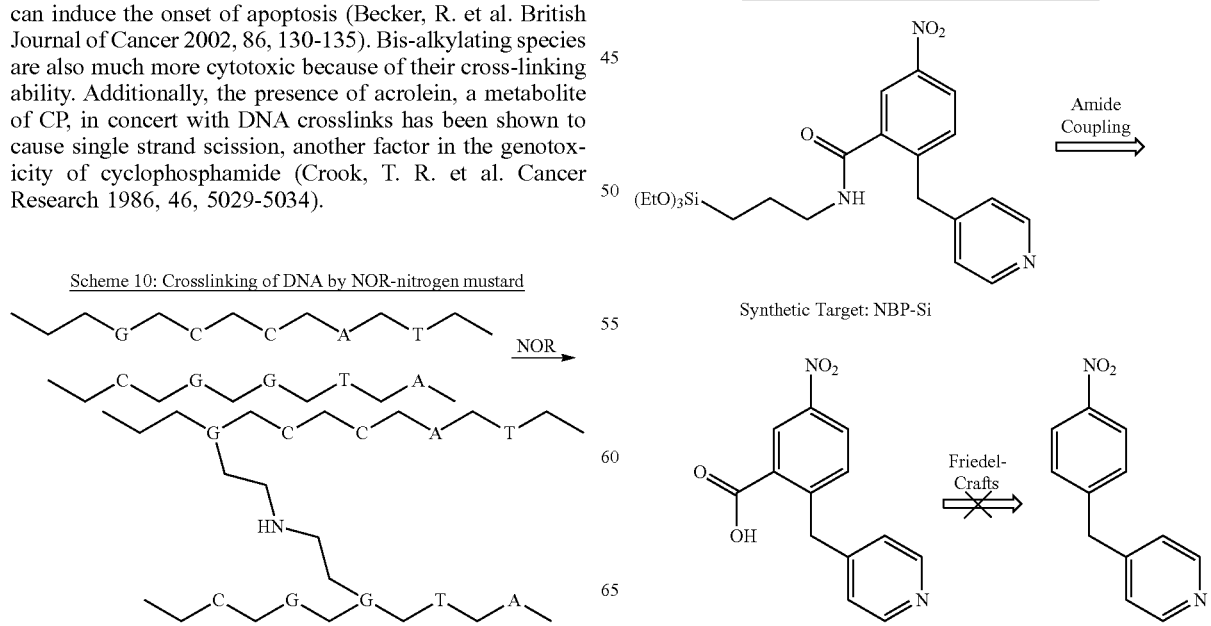

Though 4-(4-nitrobenzyl)pyridine is available commercially, the molecule is difficult to functionalize on its aromatic rings. Access to the arene-carboxylic acid by Lewis-acid catalyzed Friedel-Crafts acylation or Vilsmeier-Haack formylation is not possible because the nitrobenzene ring is too electron poor and the molecule is sensitive to strong Lewis bases and high temperatures. If the acylation was attempted without the nitro group in place, the ring would likely be sufficiently electron rich, but the acylation would occur in the para position due to sterics (Dornow; Machens; Bruncken Chem. Ber. 1951 84, 147; and Pyridine and its Derivatives Part Two Klingsberg, E., Ed.; Interscience: New York, 1961). As a side note, the pyridine ring is significantly slower in electrophilic aromatic substitution reactions due to its electron poor nature.

Reduction of the nitro group in 4-(4-nitrobenzyl)pyridine should yield a ring electron rich enough to undergo Vilsmeier-Haack formylation, but likely the electron rich amine functionality would point the formylation ortho as shown in Scheme 12 below.

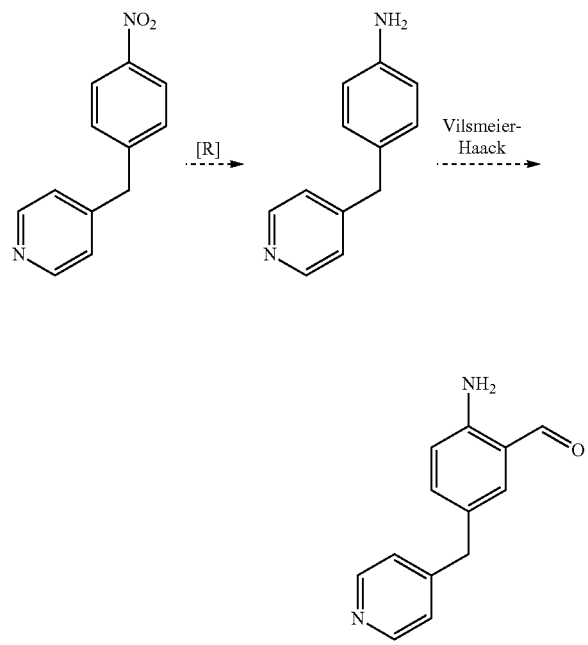

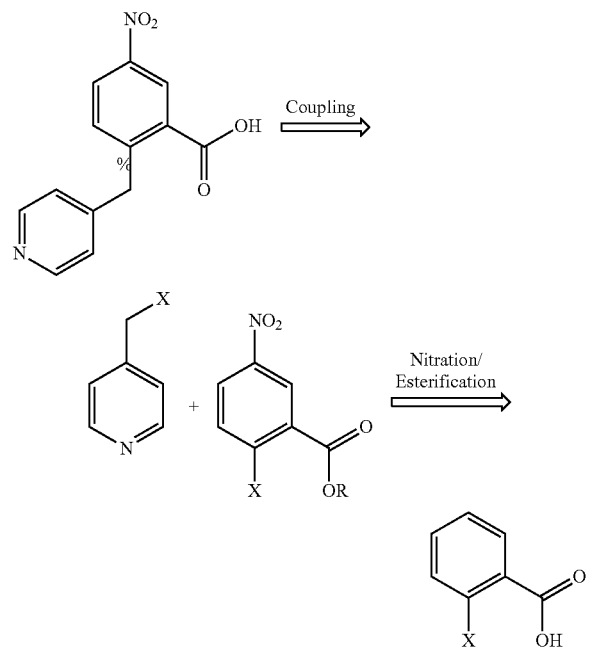

Therefore we looked at synthesizing the benzylpyridine motif from readily available 4-picoline derivatives and ortho-carbonyl substituted benzene-halides. By retrosynthetic analysis, we imagined some type of C—C coupling to generate the ortho-carbonyl substituted 4-picolyl-benzene. The nitro group could be installed pre- or post-coupling, depending on the sensitivity of coupling towards the nitro group as shown in Scheme 13 below. Although the below strategy was not successful initially, it is predicted that this is a viable method of synthesizing compounds of described herein, with some changes to the conditions.

Picoline as Electrophile

The synthetic strategy, as outlined in Scheme 14, is based on the key step of carbon-carbon bond formation in Scheme 14 through a nitroaryl cuprate as reported by Knochel in 2005 (Sapountzis, I. et al. Org. Chem. 2005, 70, 2445-2454). Metalated nitroaryl species are difficult to synthesize because of their sensitivity to reduction by electron transfer, as exemplified in the Bartoli indole synthesis (Bartoli, G. et al. Tetrahedron Letters 1989, 30, 2129-2132; and Bosco, M. et al. Journal of the Chemical Society, Perkin Transactions 2 1991, 5, 657-663). Thus their preparation has only been reported a handful of times (Tucker, C. E. et al. J. Am. Chem. Soc. 1992, 114, 3983-3985; Cameron, J. F. and Frechet, J. M. J. J. Am. Chem. Soc. 1991, 113, 4303-4313; Wiriyachitra, P. et al. J. Org. Chem. 1979, 44, 3957-3959; Köbrich, G. and Buck, P. Chem. Ber. 1970, 103, 1412; and Buck, P. et al. Chem. Ber. 1970, 103, 1431). Most of the reports for the synthesis of metalated nitroaryl species utilize lithium as the metal at very low temperatures (−100° C.), and further functionalized metalated nitroaryl species had not been reported before the Knochel publication in 2004. Nitro groups are often refractory to transition metal facilitated cross-couplings because strong coordination of the nitro group can poison a catalyst (Berman, R. S. and Kochi, J. K. Inorg. Chem. 1980, 19, 248-254; and Fan, X.-H. and Yang, L.-M. European Journal of Organic Chemistry, 2010, 2457-2460). The metalated aryl specie depicted here is further complicated by the presence of an ester, which poses potential for addition of the metal transfer reagent (PhMgCl in this case) to eject ethoxide and generate the diarylketone. Likely the method was successful because the rate of bromide/magnesium exchange was so rapid, with completion observed within 30 seconds at −40° C. by GC/MS.

Scheme 14: Synthetic Plans Towards NBP-aci

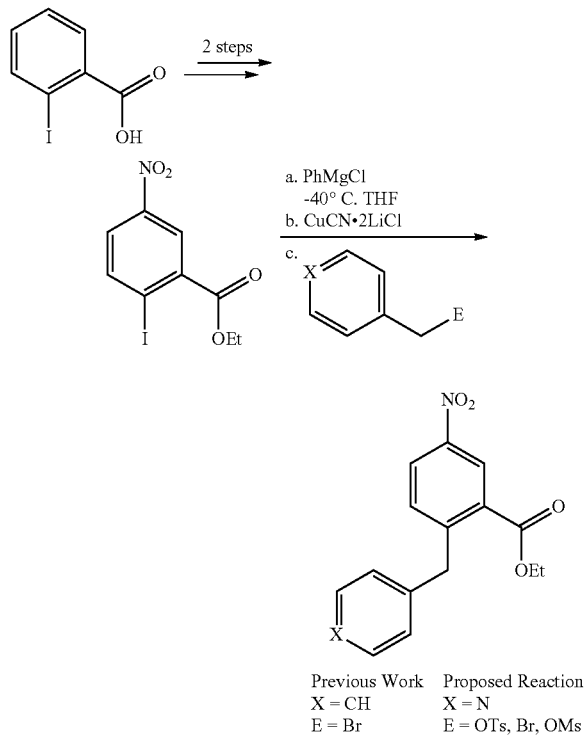

Previous Work
X = CH
E = Br

Proposed Reaction
X = N
E = OTs, Br, OMs

Preparation of 5-iodo-2-nitrobenzoic acid by the procedure outlined by Miyata in 2010 (Jithunsa, M. et al. Org. Lett. 2010, 13, 518-521) was found to not to furnish the nitrated compound in our hands as reported. Miyata reported that nitration of 2-iodobenzoic acid was carried out by the addition of nitric acid to a solution of starting material at 0° C., and then warmed to RT while stirring for twelve hours. The procedure used by the Knochel group for the nitration of ethyl-2-iodobenzoate, wherein the reaction was heated to 75° C. for twelve hours, was found to yield 2-iodo-5-nitrobenzoic acid with a 95% yield when applied to 2-iodobenzoic acid.

Scheme 15: Nitration of 2-iodobenzoic acid

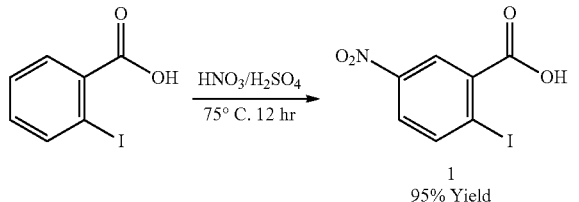

1
95% Yield

Esterification of acid 1 was performed by formation of the acid chloride by reflux in thionyl chloride, removal of thionyl chloride in vacuo, and subsequent reflux in ethanol. The product 2 precipitated out upon stirring at room temperature and was isolated at 72% yield.

Scheme 16: Esterification of 2-iodo-5-nitrobenzoic acid

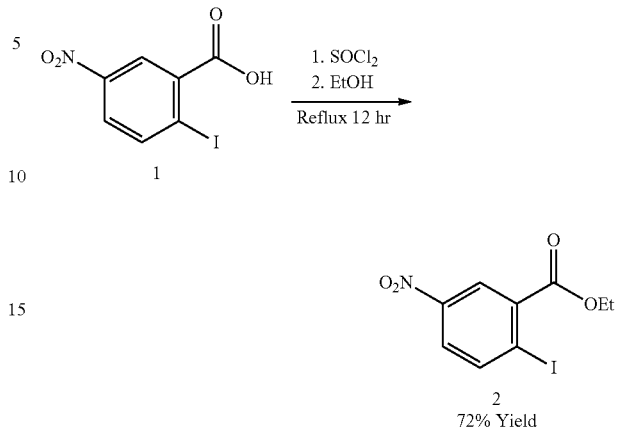

2
72% Yield

Preparation of the pyridine electrophilic coupling partner was problematic. Treatment of the commercially available 4-pyridinemethanol with p-toluenesulfonyl chloride resulted in an expected dark red solution. Aqueous workup and extraction with dichloromethane (DCM) led to, as expected, a red solution in dichloromethane. Upon removal of the DCM a dark red tar was isolated—this seemed reasonable since similar compounds are reported to be red oils, however the tar was found to not be soluble in DCM: clearly rotary evaporation led to polymerization. Polymerization again occurred when care was taken to avoid applying any heat to the compound, suggesting that the polymerization was due to concentration. Furthermore, attempt to generate the less reactive methanesulfonate led to the same polymerized tar.

Scheme 17: Tosylation and Mesylation of 4-pyridinemethanol

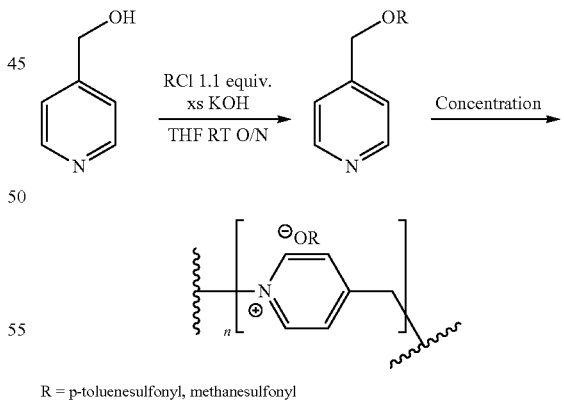

R = p-toluenesulfonyl, methanesulfonyl

This polymerization problem was exacerbated in preparation of the even less reactive bromo derivative by treatment of the alcohol with phosphorus tribromide in dioxane because the reaction required heating to 40° C. The brominated product was not observed, but only the insoluble red tar.

Scheme 18: Bromination of 4-pyridinemethanol

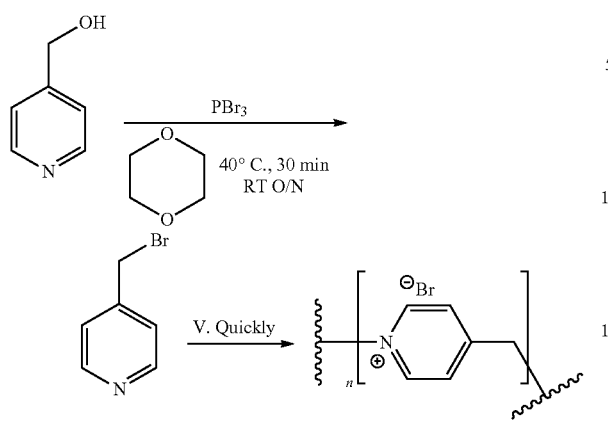

Since it seemed possible to transiently generate the tosylated pyridine as in Scheme 17, it was thought that the tosylate could be utilized without isolation. A by-product of the tosylation is $H_2O$, so the reaction was stirred with 4 Å molecular sieves in order to remove the evolved $H_2O$. Additionally, KOH was used in a stoichiometry of unity rather than excess. Subsequently the dark red reaction mixture was transferred by filter-cannula into the coupling reaction.

Scheme 19: Copper Mediated Coupling of a Grignard Reagent and an Aryl Halide

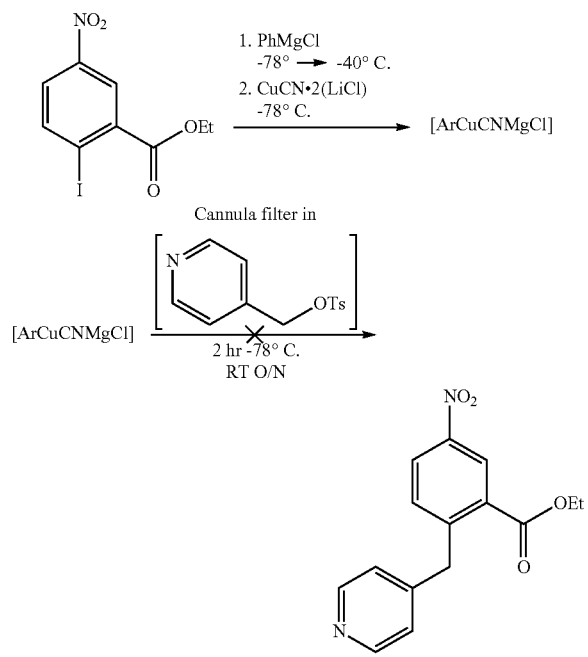

No product was observed by $^1$H NMR spectroscopy or mass spectrometry. Likely the major problem was the picoline-tosylate reagent, so attempts were made to add the generated aryl-Grignard reagent into 4-formylpyridine, but the lactone was isolated in only trace amounts and found resistant to ring opening and reduction. Trace amounts of the dehalogenated starting material was also observed. Bulkier protection with an isopropyl ester yielded the same results (note: isopropyl ester was synthesized from 5-iodo-3-nitrobenzoic acid in the same manner as the ethyl ester (70% yield)).

Scheme 20: Lactone Formation with 4-formyl-pyridine

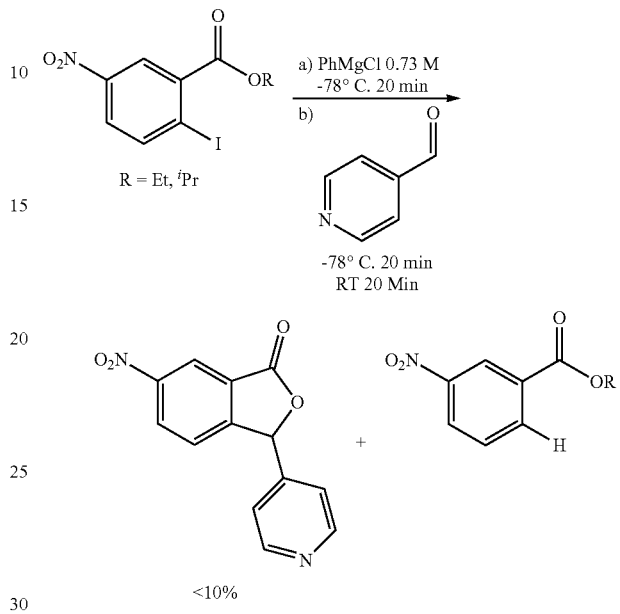

Synthesis of "dianions" of 5-iodo-3-nitrobenzoic acid, N-alkyl 5-iodo-3-nitrobenzamide, and N-methyl-benzamide was also attempted in order to limit the formation of the lactone, under the assumption that deprotonated carboxylic acids and amides could not undergo addition by an alkoxide.

Synthesis of a Grignard dianion from 5-iodo-3-nitrobenzoic acid is complicated by the rapidity with which the iodide/magnesium exchange occurs and inter-complex quenching of the arylmagnesium specie (Beak, P. and Chen, C.-W. Tetrahedron Letters 1985, 26, 4979-4980; Beak, P. et al. J. Am. Chem. Soc. 1988, 110, 3538-3542; and Beak, P. et al. J. Org. Chem. 1993, 58, 7330-7335). Often metalated acid bearing arenes will quench on themselves, leading to unproductive reactivity. Thus it is not possible to generate the Grignard-carboxylate by the addition of two or more equivalents of PhMgCl. Analogously, this phenomenon is also observed with primary and secondary halo-benzamides.

Scheme 21: Self-Quenching in Dianion Formation of Grignard Reagents of Acid Bearing Arenes

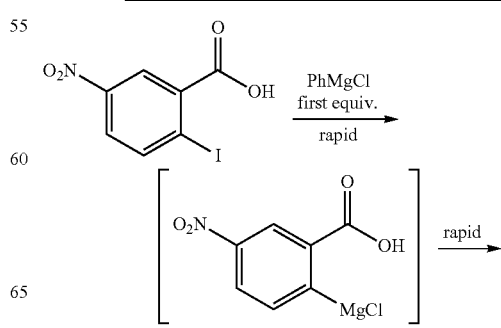

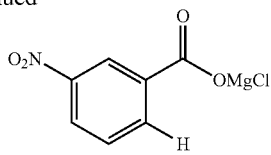

Preparation of the dianion-Grignard reagent through the carboxylic acid was not attempted due to solubility problems, so the secondary amide was prepared through the acid chloride in 40% yield. As shown in Scheme 22, after treatment of the amide with sodium hydride to first generate the sodium amidate, PhMgCl was added to generate the aryl-grignard specie. Likely the Grignard was not formed, since no product (amide/alcohol or lactone) was observed.

Scheme 22: Dianion Formation by Sodium Hydride and Halogen-Magnesium Exchange

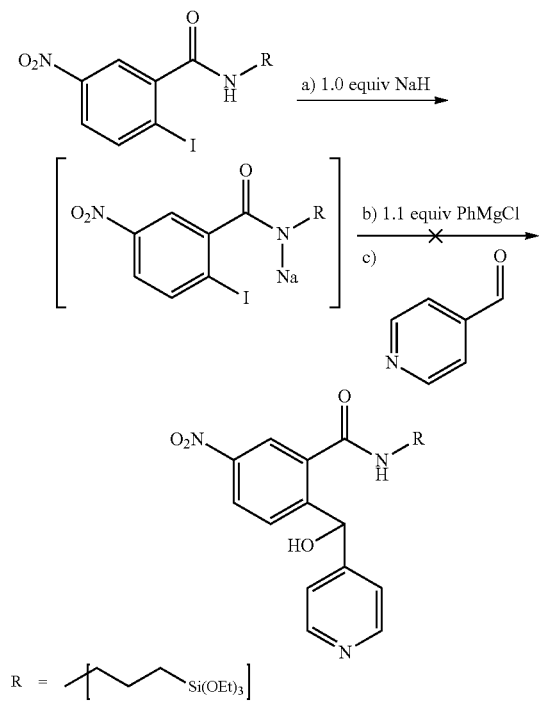

As shown in Scheme 23, N-methyl-benzamide is known to form the dilithiated derivative after treatment with two equivalents of $^n$BuLi in THF at reflux by directed ortho-metalation, and the metalated amide should analogously prevent the formation of the undesirable lactone (Puterbaugh, W. H. and Hauser, C. R. J. Org. Chem. 1964, 29, 853-856). Synthesis of the dilithiated benzamide was facile: slow addition of the $^n$BuLi yielded a colorless crystalline solid which precipitated out of THF completely after the first equivalent of $^n$BuLi, indicative of the lithiated amide. As the second equivalent of $^n$BuLi was added, this salt reacted rapidly and dissolved as a yellow-brown solution, indicating formation of the dilithiate. Frustratingly, however, the dilithiated specie generated an intractable mess on trapping with 4-formylpyridine at −78° C. Likely the dilithiate was too highly reactive, potentially ionizing the aldehyde or adding into the pyridine ring.

Scheme 23: Dilithiation of N-methylbenzamide

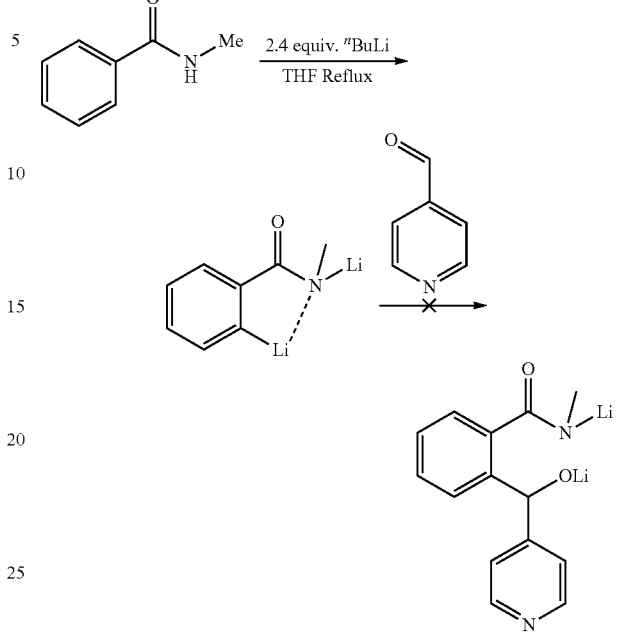

4-Picoline as Nucleophile

Due to the myriad difficulties in the approach based on an electrophilic picoline, the roles of the benzene and picoline derivatives were switched from nucleophile and electrophile to electrophile and nucleophile, respectively. This approach was inspired by a later Knochel report (Duez, S. et al. Angewandte Chemie International Edition 2011, 50, 7686-7690) utilizing their previously developed hindered base TMPZnCl.2(LiCl) (TMP=2,2,6,6-tetramethylpiperidyl) to directly generate a zincated picoline and perform Negishi type couplings.

While there are a number of strategies for the arylation of 2-picolines, the Knochel report details the first arylation of 4-picoline. Arylation of these picolines is complicated by a number of factors (Niwa, T. et al. Org. Lett. 2007, 9, 2373-2375): (1) 2-picolines, though directing, form strong chelates with palladium that are reluctant to reductively eliminate, (2) in metalated 4-picolines the quinone type structure dominates the equilibrium, and (3) though the pKa of the methyl group is relatively low (~32), metalation requires specific choice in base because often ring-addition can occur with strong bases (Mansour, T. S. et al. Journal of the Chemical Society, Perkin Transactions 2 1985, 12, 2045-2048). Knochel et al employed the Lewis acid scandium triflate to occupy the nitrogen in the picoline, which could limit the swamping of the catalyst and encourage reductive elimination.

Scheme 24: Problems with Benzylic Couplings of 4-Picoline

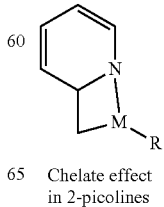

Chelate effect in 2-picolines

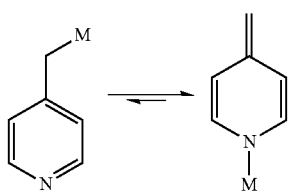

The quinone form dominates the equilibrium

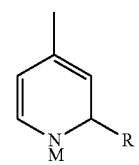

Often ring addition supercedes deprotonation

Knochel was able to demonstrate the benzylic coupling of picolines with a variety of aryl-bromides with good yields (69-99%). The aryl-bromides used had electron donating and withdrawing groups, and it was found that the added Lewis acid had the greatest benefit on the coupling with electron-poor aryl-bromides, which was relevant to our synthesis. We imagined that this method could be applied towards the synthesis of our target compound.

Scheme 25: Previous and Proposed Coupling Reactions of Zincated 4-Picoline

Previous Work

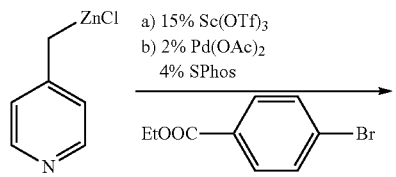

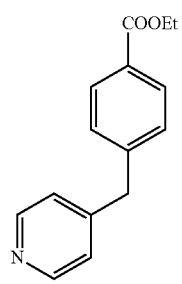

Proposed Work

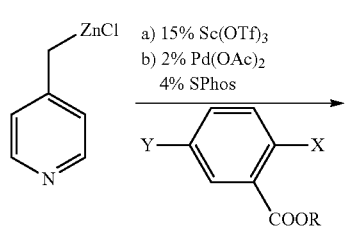

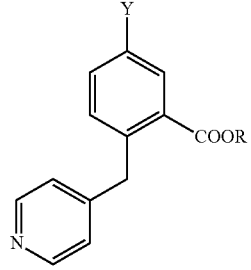

Y = NO$_2$, H
R = Et, $^i$Pr
X = I, Br

Knochel's work only explored one ortho-substituted aryl-bromide, which was electron donating, and no electron poor ortho-substituted aryl bromides, nor aryl-bromides with two electron withdrawing groups. Additionally, only aryl-bromides were studied and no comment was made concerning aryl-iodides. However, we thought the difference in our substrates and the substrates used successfully by the Knochel group were minor.

The TMP base was prepared by the treatment of TMPH with "BuLi in THF and hexanes, as per the published procedure. The nBuLi solution was titrated with iodine in a saturated solution of LiCl in THF, as per a modified procedure also published by the Knochel group (Knochel, P. and Krasovskiy, A. Synthesis 2006, 5, 0890-0891). The concentration of the "BuLi was found to be almost half the reported value, and this was common across old and new bottles alike: this has become a major problem from Sigma-Aldrich, and likewise titrations of "BuLi and MeLi within our research group corroborate this issue. Nonetheless, the "BuLi was used towards the synthesis of the zincating agent TMPZn. The Knochel group reported that TMP-Zn was titrated by benzoic acid with 4-(phenylazo)diphenylamine as an indicator. The reported method for the titration of the TMP-Zn specie was found to be a poor method to determine the concentration of the metalated picoline because the purple-to-yellow endpoint was difficult to observe precisely.

Scheme 26: Zincation of 4-picoline

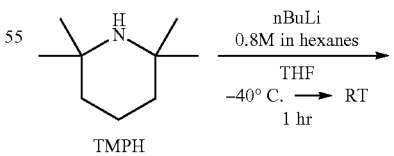

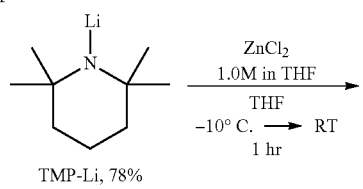

TMP-Li, 78%

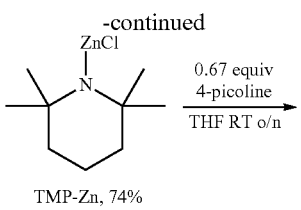

TMP-Zn, 74%

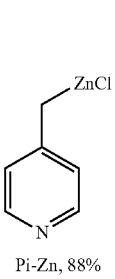

Pi-Zn, 88%

Due to the inability to measure the yield of zincated TMP, a GC-MS procedure was developed to determine the concentration of metalated TMP and 4-picoline over the course of the transformations. As each metalated compound was formed, two small aliquots were taken and quenched separately over deuterium oxide and iodine. GC-MS was used to monitor the metalated species by the H/D isotopic ratios. Initially we thought that quenching Pi-Zn on $I_2$(s) would yield the iodo derivative but it was never observed. However, on occasion "BuI could be observed from reaction of "BuLi with $I_2$, which was useful because it further indicated how successful the initial deprotonation of TMPH was. Though the yield of TMP-Zn was reasonable, we were never able to get a solution as high as concentration as reported by Knochel (reported: 1.3 M, found: 0.4 M). With the lower concentration TMP-Zn, the zincation of 4-picoline took overnight rather than one hour, as reported by Knochel. Interestingly, if extra "BuLi was present, in addition to the observation of "BuI, the oxidative coupling of "BuLi and Pi-Zn was observed to yield 4-pentylpyridine, possibly induced by iodine. This result could yield a significant result in cross-couplings if optimized, since most iodine facilitated oxidative couplings are either between enolates or intermolecular C—Nbond formation (Jeffrey, J. L. et al. Angewandte Chemie International Edition 2013, 52, 2194-2197; Casey, B. M. and Flowers, R. A. J. Am. Chem. Soc. 2011, 133, 11492-11495; Fan, F. et al. Org. Lett. 2012, 14, 1405-1407; and Renaud, P. and Fox, M. A. J. Org. Chem. 1988, 53, 3745-3752). No iodine facilitated oxidative coupling of two organometallic reagents could be found in literature.

Using the GC-MS to monitor each reaction allowed the optimization of the synthesis of Pi-Zn. Pi-Zn was then applied towards coupling reactions, as shown in TABLE 1, but they did not yield any product. Furthermore, we could not get this reaction to work with any of our other proposed substrates, so likely we could not get this reaction to work due to issues with the ortho-ester or contaminants. These reactions also did not work with Pd(dba)$_2$/TFP catalyst as reported by Knochel for the cross-coupling of functionalized nitroarylmagnesium halides.

TABLE 1

Benzylic Coupling of Zincated 4-Picoline

| Entry | Y | X | R | Result |
|---|---|---|---|---|
| 1 | NO$_2$ | I | Et | NR |
| 2 | NO2 | I | $^i$Pr | NR |
| 3 | H | I | Et | NR |
| 4 | H | Br | Et | NR |

(NR = No Reaction)

It was considered a possibility that might be a problem with the TMP-Zn, especially since the correct concentration of the TMP-Zn could not be achieved. Previous reports have shown that, while "BuLi, $^s$BuLi and other very strong bases will add into the pyridine ring, MeLi results in a 95% preference for metalation of the methyl group. If MeLi works as well as TMP-Zn in the deprotonation of 4-picoline, it should improve the metalation/coupling procedure because tedious preparation of TMP-Zn would not be necessary. Utilizing GC-MS to monitor the metalation and transmetalation of picoline by analysis of quenched products, the metalation of 4-picoline was achieved by treatment of MeLi at 0° C. Salt metathesis of lithiated 4-picoline with ZnCl$_2$ in THF afforded Zincated 4-picoline, which was tested under coupling conditions against our aryl-halide coupling partners as in TABLE 1, however the products were never observed by MS or $^1$H NMR spectroscopy.

The final coupling experiment tried was with a substrate from the Knochel 2011 publication, 4-bromo-N,N-dimethylaniline. This reaction was successful to some extent, which indicated that the conditions employed were not altogether refractory to the arylation of 4-picolines, and that likely our previous attempts at cross-coupling were foiled by the presence of the ortho-ester functionality.

Scheme 27: Repeating a Knochel Substrate

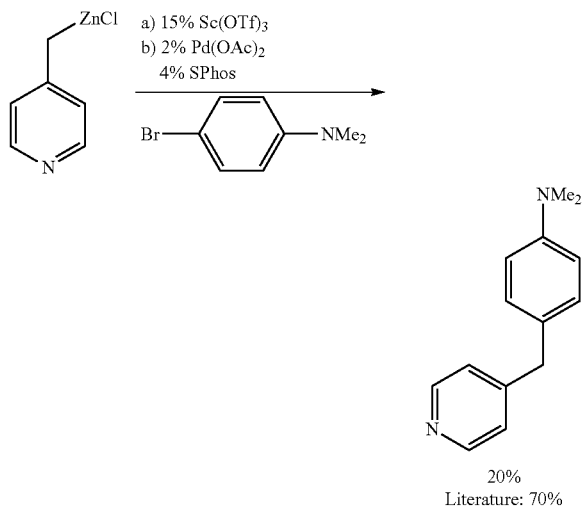

20%
Literature: 70%

While a coupling method was never developed successfully, this work did succeed in exploring the metalation of 4-picoline. The results of this study are shown in Scheme 28. Previously mentioned work utilized only NMR techniques to determine the metalation/ring addition chemistry of strong bases acting upon 4-picoline, while this work utilizes arguably more quantitative GC-MS methods. Concerning the chemistry of strong bases and picolines, there is significant disagreement between results by various researchers (J. P. Wibaut and J. W. Hey, Red. Trav. Chim. Pays-Bas, 1953, 72, 513), about the ratios of products achieved, whether they be metalated or ring-addition products. This work is in general agreement with the work by Kaiser et al, but we found more ring-addition products with methyl lithium at room temperature than they describe.

Scheme 28: Metalation and Quenching Reactions of 4-picoline

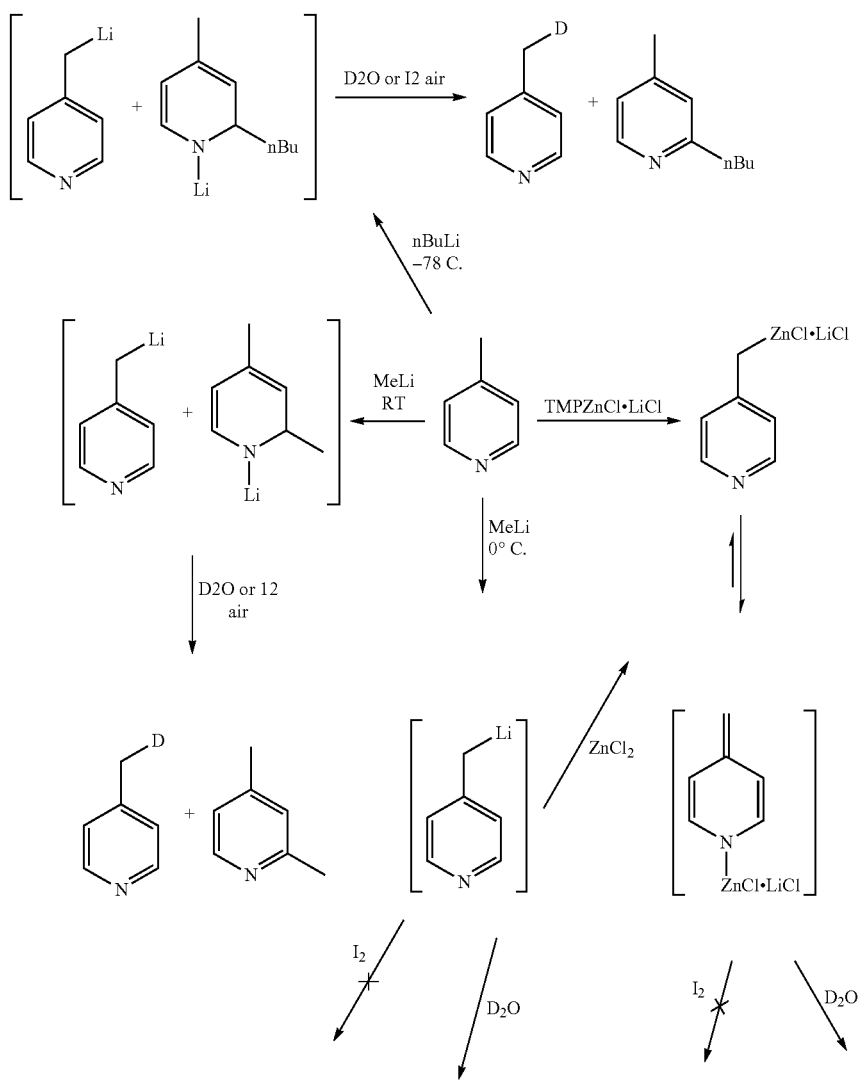

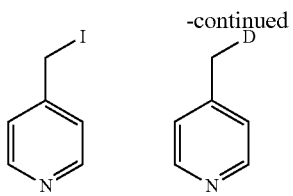

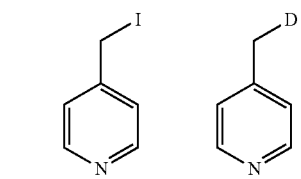

Though the Knochel report on benzylic coupling of 4-picolines was thorough in method development, the method suffers significantly when applied to target oriented synthesis. Synthesis of the metalated TMP base is tedious and unpredictable, and commercially available "BuLi from Sigma-Aldrich is unsatisfactory. As well, the coupling method does not work when there is an ester ortho to the bromide, which significantly hampers this methodology. Furthermore, certain aspects about this method seem to be rather inexplicable: use of 15% scandium triflate is rather puzzling, since this is very high for a catalyst loading and the reported failure of lithium diisopropylamide to produce any product does not make much sense. Clearly many aspects of this coupling reaction are poorly understood, and the extrapolation of the results to further access desirable picoline derivatives is unpredictable.

Pericyclic Strategy

Since an anionic strategy was not succeeding for the synthesis of our target molecule, we decided to look towards more unusual strategies towards the core 4-(2'-carbonyl-benzyl)pyridine motif. In 2008, a group from Guru Jambheshwar University of Science and Technology reported that polystyrene supported hypervalent iodine can induce an oxidative rearrangement to the diacylbenzene derivative, as shown in Scheme 29 (Kumar, S. and Kumar, D. Synthetic Communications 2008, 38, 3683-3699).

Scheme 29: PhI(OAc)₂ Mediated Oxidative Rearrangement

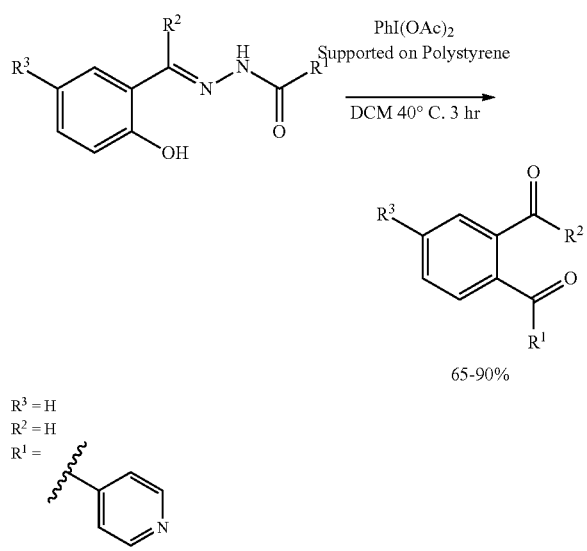

While the rearrangement of this type has been known for some time, Kumar's report represents the first time applying the procedure to a pyridine derivative. From the diacylbenzene derivative X, a few adjustments of oxidation states and a nitration should lead us to our desired product.

Scheme 30: Transformations Required to Product

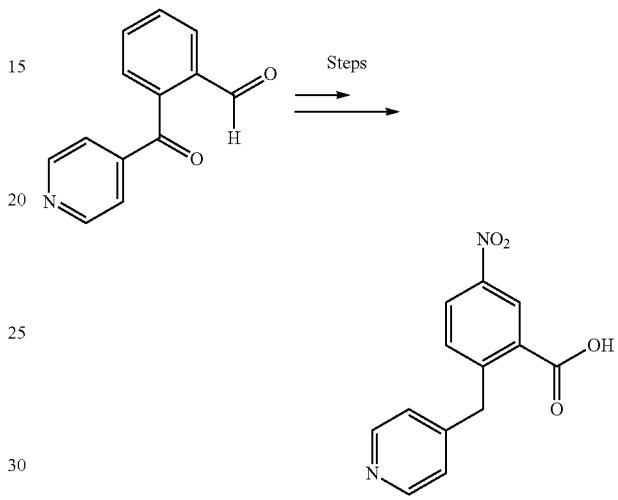

This rearrangement of hydrazides can be performed with a few oxidizing agents: lead tetraacetate (LTA) (Kotali, A. and Tsoungas, P. G. Tetrahedron Letters 1987, 28, 4321-4322), phenyliodoso diacetate (Moriarty, R. M. and Berglund, B. A.; Rao, Synthesis 1993, 1993, 318-321), and sodium hypochlorite (Kotali, A. and Lafazanis, G. S. Abstracts, 230th ACS National Meeting, Aug. 28-Sep. 1, 2005; American Chemical Society: Washington D.C., 2005; ORGN 77). The oxidative rearrangement was first discovered with LTA, and this reagent has since been used for the synthesis of boron containing near-IR fluorescent dyes (Ulrich, G. et al. J. Org. Chem. 2011, 76, 4489-4505; and Ulrich, G. et al. Synlett 2007, 1517-1520), diarylisobenzofurans (Jacq, J. et al. Org. Lett. 2008, 10, 3757-3760), 7,8- and 3,4-diacylcoumarins (Kotali, A. et al. Tetrahedron Letters 2007, 48, 7181-7183; and Kotali, A. et al. Tetrahedron 2012, 68, 761-766), 6-substituted dibenzazepin-11-ones (Kotali, A. et al. Heterocycle 2001, 55, 1057-1062), thiophene bearing monomers for polymeric photovoltaics (Li, D. et al. Polymer 2013, 54, 5543-5552), 2-acylbenzoyl bromides (Katritzky, A. and Kotali, A. Tetrahedron Letters 1990, 31, 6781-6784), and others.

The mechanism is somewhat unusual, and has not been completely elucidated, but the Kotali group has done several experiments in support of the following mechanism with LTA: upon protonolytic coordination of the lead reagent with the NH hydrazide, one of the acetate ligands migrates into the hydrazone double bond, inducing a cyclization and further acetate migration to the 1,3,4-oxadiazoline. At this stage in the mechanism, the 1,3,4-oxadiazoline may be isolated (Hoffmann, R. W. and Luthardt, H. J. Tetrahedron Letters 1966, 7, 411-414). However, if the benzene ring is ortho-hydroxy-substituted, then displacement of the acetate group by the hydroxy functionality generates a tricyclic 1,3-dioxane. Rapid extrusion of dinitrogen and decomposition of the resulting strained ring system yields the product.

Scheme 31: Mechanism of Lead Tetraacetate Induced Oxidative Rearrangement

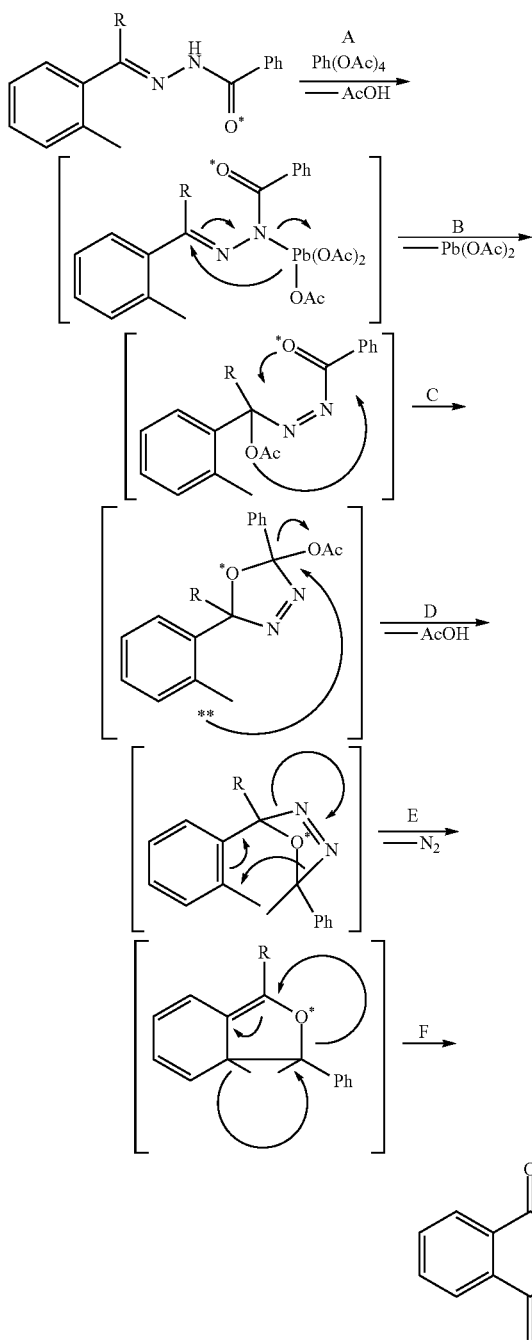

Kinetic studies show that the rate determining step is the protonolysis of the NH in the first step (Harrison, M. J. et al. Journal of the Chemical Society C: Organic 1967, 735-739; Scott, F. L. and O'Mahony, T. A. F. Tetrahedron Letters 1970, 11, 1841-1844; and O'Mahony, T. et al. Journal of the Chemical Society, Perkin Transactions 2 1972, 1319-1323). ESR and CIDNP studies suggest that a radical is not present in the reaction, and that likely it proceeds by a polar mechanism, unlike other LTA reactions. $^{18}$O labelling proves the origin of the oxygens in the product (Katritzky, A. R. et al. Org. Chem. 1991, 56, 5049-5051). Finally, acid catalysis was discounted because the reaction was not slowed in the presence of triethylamine.

Synthesis of the NBP-α-carbonyl Core

The N-pyridoylhydrazone 3 was synthesized by stirring salicylaldehyde and isoniazid in refluxing isopropanol at 65% yield, in agreement with literature procedure. After optimization, this reaction went to near completion (97%) when ethanol was utilized as solvent. The product was less soluble in ethanol than isopropanol, so likely the precipitation of the product drove the reaction to higher yields. This reaction was scaled up to yielding 80 grams of product without affecting the yield or procedure.

Scheme 32: Formation of Hydrazide 3

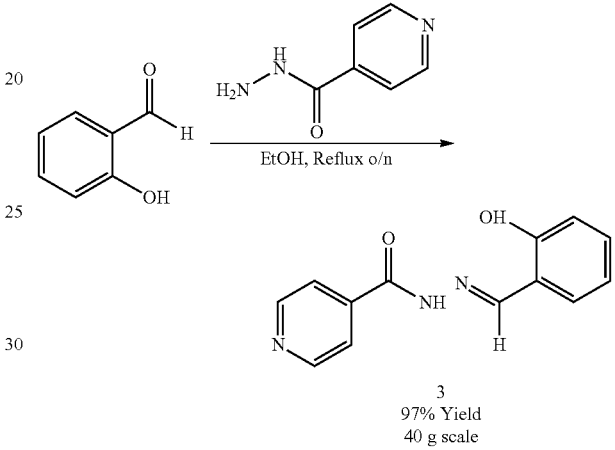

3
97% Yield
40 g scale

The N-pyridinoylhydrazone 3 was then subjected to oxidative rearrangement conditions, wherein freshly recrystallized LTA was added slowly to a solution of 3 in dry THF. Later, the recrystallization of LTA was found not to be necessary or favorable, since recrystallization removed the acetic acid additive which stabilized the reagent while weighing under ambient atmospheric conditions.

Scheme 33: Oxidative Rearrangement Induced by Lead Tetraacetate

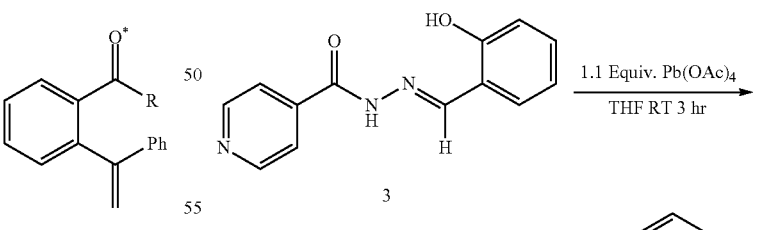

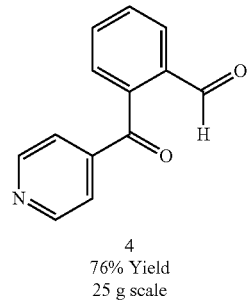

4
76% Yield
25 g scale

Initially, we had hoped to avoid extensive column chromatography of compound 4, so a simple silica plug was utilized to reduce the quantity of impurities. This purification was suitable for the next reaction, wherein the aldehyde was oxidized directly to the ester by oxone, a potassium peroxymonosulfate triple salt (Travis, B. R. et al. Org. Lett. 2003, 5, 1031-1034). Initially, we used isopropyl alcohol, but the product was not observed, only some other oxidation product. The methyl ester was produced from oxidation in methanol in moderate yields (60%), so we moved forward with the deoxygenation.

Scheme 34: Direct Access to the Ester from an Aldehyde

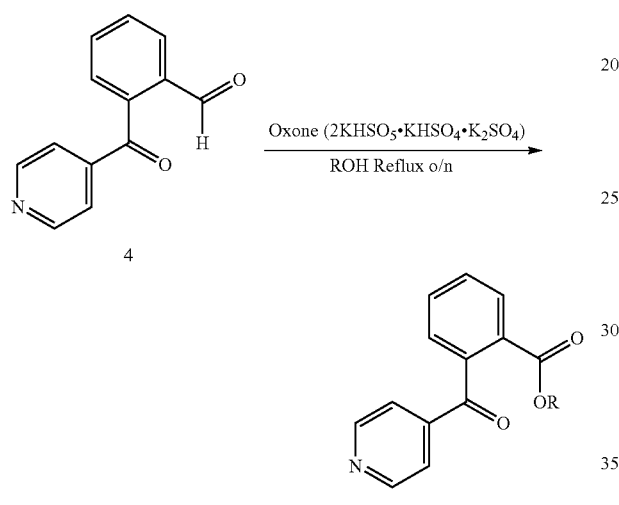

R = $^i$Pr, NR
R = Me, 60%

Deoxygenation

Deoxygenation was attempted as reported by the Merck Research Labs, utilizing $H_3PO_2$ as the hydrogen source in an iodide catalyzed reduction (Wu, G. G. et al. Org. Lett. 2011, 13, 5220-5223; and Albouy, D. et al. Journal of Organometallic Chemistry 1997, 529, 295-299). As before, the lactone was a very stable intermediate, but continuing application of heat yielded the diarylmethane specie. This product proved difficult to isolate because in aqueous solution it occupies a zwitterionic state, likely only isolable by crystallization, which was not achieved because the scale was so small.

Scheme 35: Deoxygenation by Hypophosphoric Acid

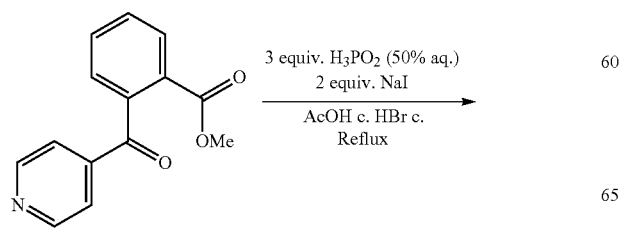

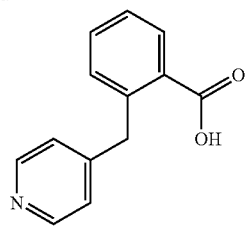

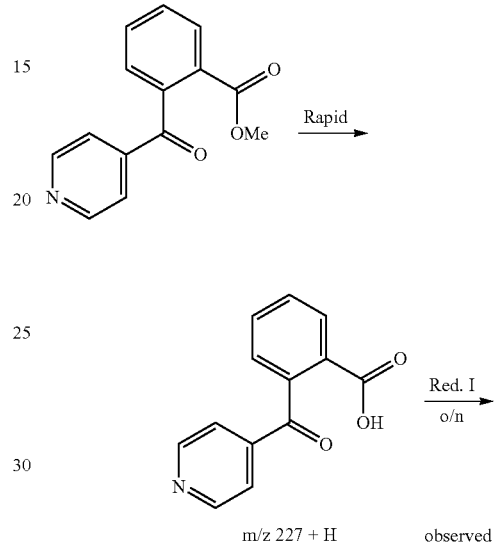

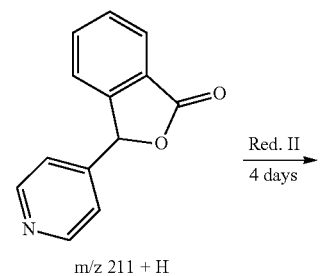

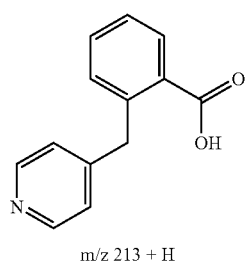

While working on the deoxygenation by hypophosphorous acid, another route towards the α-carbonyl-benzylpyridine core was explored using a Wolff-Kishner reduction. Instead of directly oxidizing the aldehyde, an acetal protecting group was installed on the aldehyde by acid catalysis under Dean-Stark conditions. This reaction required extensive purification of the starting material by column chromatography: otherwise the compound decomposed under reflux conditions.

Scheme 36: Acetal Protecting Group Installation

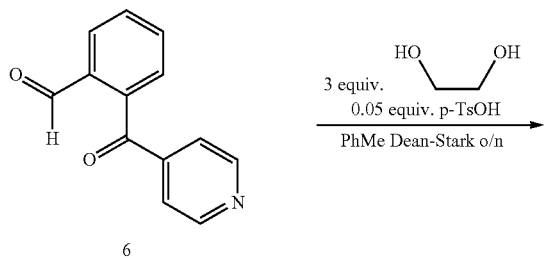

This represents the first synthesis of the 1-(1,2-dioxolane)-2-carbonyl-benzene motif from 1,2-(dicarbonyl)-benzene starting material. Previous reports generally utilize Grignard addition into an aldehyde and subsequent oxidation of the alcohol. While we are not totally certain why three equivalents of ethylene glycol were required for the protection, 1.2 equivalents of ethylene glycol furnished only 50% conversion to the product. Possibly the ethylene glycol-toluene azeotrope came into effect, where ethylene glycol boiled off with the toluene, and then was removed from the system because it separated into the water layer in the Dean-Stark collector. Interestingly, no reaction at the ketone was observed, though it was not entirely surprising considering the large steric hindrance. After conditions were optimized, this reaction required no column chromatography to purify the products. This reaction was scaled to 15 grams starting material without effect on the procedure or yield.

Wolff-Kishner deoxygenation of the acetal protected diaryl ketone was facile (Diez-Cecilia, E. et al. Tetrahedron Letters 2011, 52, 6702-6704). Treatment of the ketone with distilled hydrazine (35% in H$_2$O) and subsequent KOH under strict exclusion of air at 135° C. in a sealed vessel yielded the diarylmethane in excellent yields. Fortuitously, the harsh reaction conditions seemed to decompose any impurities or side products, as the product came out in higher purity than the starting material after a simple aqueous work-up, as observed by $^1$H NMR spectroscopy. Furthermore, no hydrazinylpyridines or hydroxypyridine products were observed as result of ring-addition. The acetal protecting group was then quantitatively removed under acidic aqueous conditions by warming for three hours and then stirring at room temperature overnight. The deoxygenation and deprotection were scaled to 18 and 16 gram scales, respectively without change in yield or procedure.

Scheme 38: Optimized Deoxygenation and Deprotection

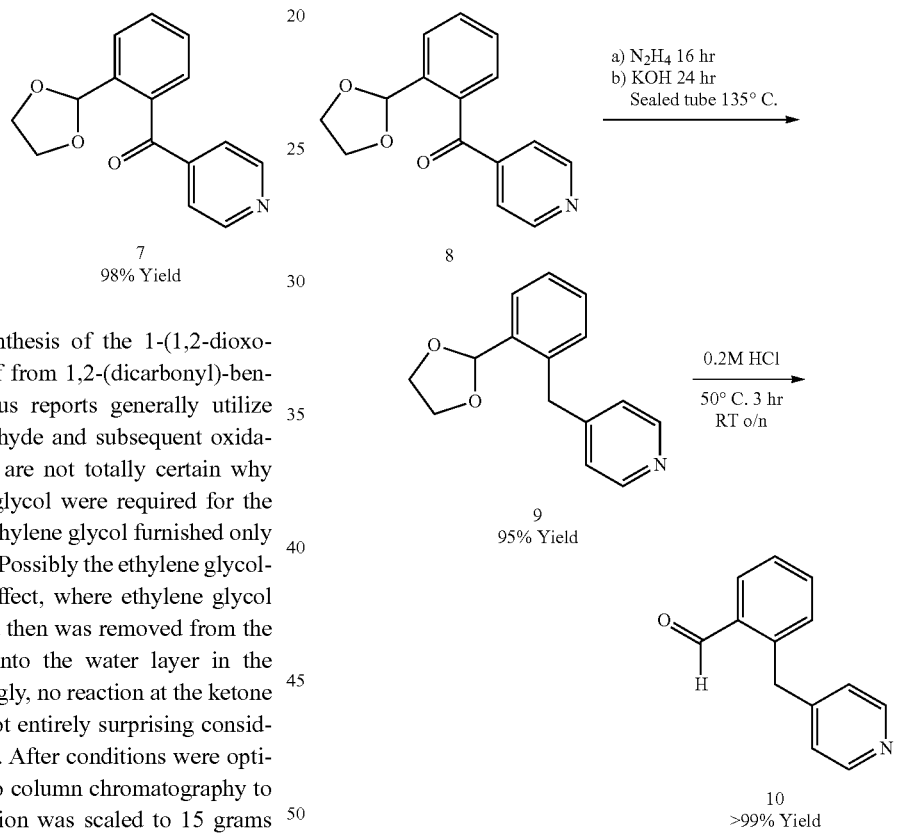

Scheme 37: Access to 1-(1,2-dioxolane)-2-carbonyl-benzene Motif

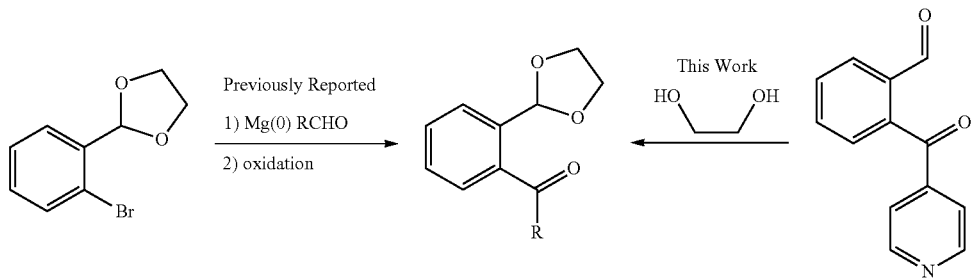

Nitration

Gratifyingly, stirring 11 in sulfuric and nitric acid yielded the appropriately substituted nitro derivative in good yields, with no nitration of the pyridine or over-nitration products detected. The position of the nitro group was determined by the splitting patterns in $^1$H NMR spectroscopy, and subsequently X-ray crystallography.

Scheme 39: Nitration of 11

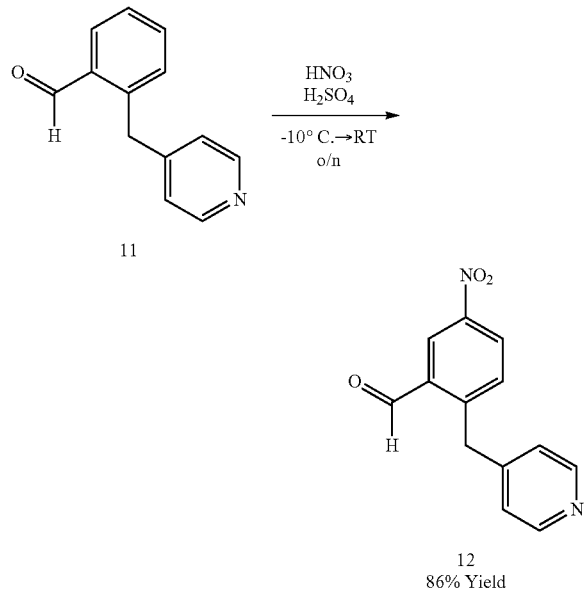

Thus the desired carbonyl substituted NBP core was obtained in 59% yield over six steps with only one step requiring column chromatography, and was scaled to furnish over 10 grams of 12. While requiring more steps, this synthetic series compares favorably to the reported synthesis of di- and tri-nitrobenzylpyridines by Herges et al, wherein $S_NAr$ of fluoronitrobenzenes with TMS-4-picolines gave significantly lower yields (Frej, A. et al. Phys. Org. Chem. 2010, 23, 1093-1098).

At this point in the synthesis, the molecule became quite sensitive. Initially KOH pellets were used to adjust the pH of the concentrated acid reaction mixture, but this resulted in a broad mixture of unidentified products. Using a saturated solution of sodium bicarbonate added drop-wise to a stirring reaction mixture while cooling the flask periodically resulted in a clean product after extraction. Likely addition of the nitro group increased the lability of the methylene protons, and deprotonation led to undesirable by-products. Additionally, the nitro compound was first extracted with either chloroform or dichloromethane, which led to a bluish colored product. NBP-yde may be alkylated by halogenated solvents, and under the basic extraction conditions the dye may form. While the discoloration of the product did not show up by NMR spectroscopy, the coloration of the compound compromised the color purity of NBP-yde. Precipitation of NBP-yde from ethyl acetate by the addition of petroleum ether yielded the orange, visually pure product.

Crystal Growth

Scheme 40: Proposed Mechanism of Slow HCl Generation by TBDPSCl and Imidazole

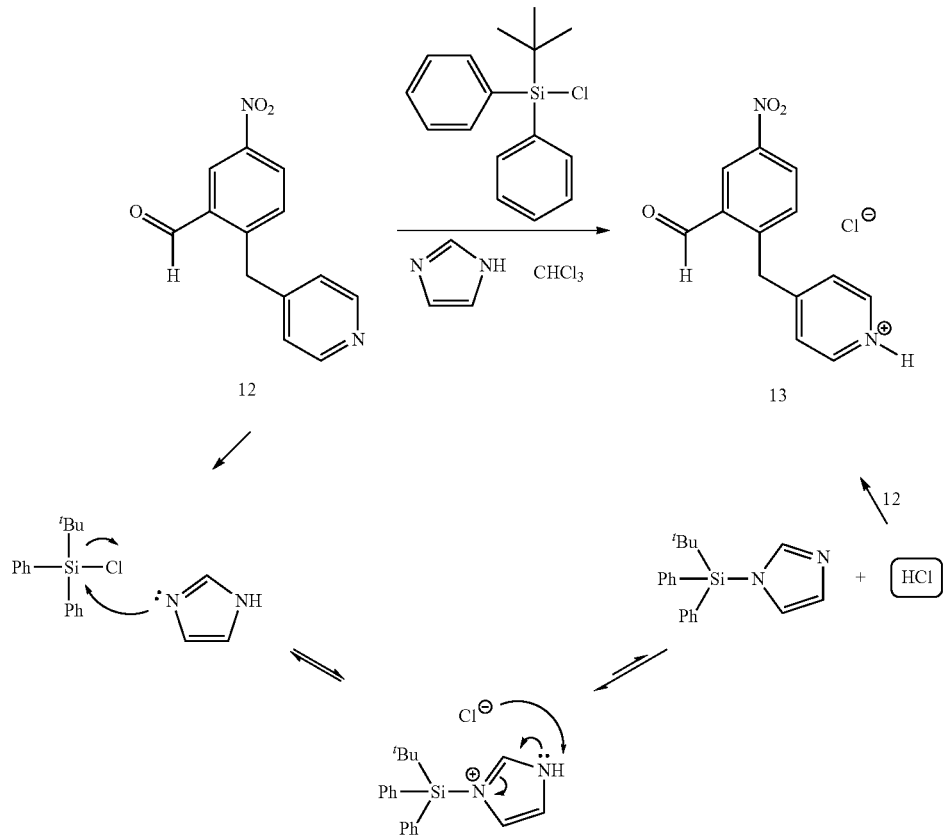

Figure 4:
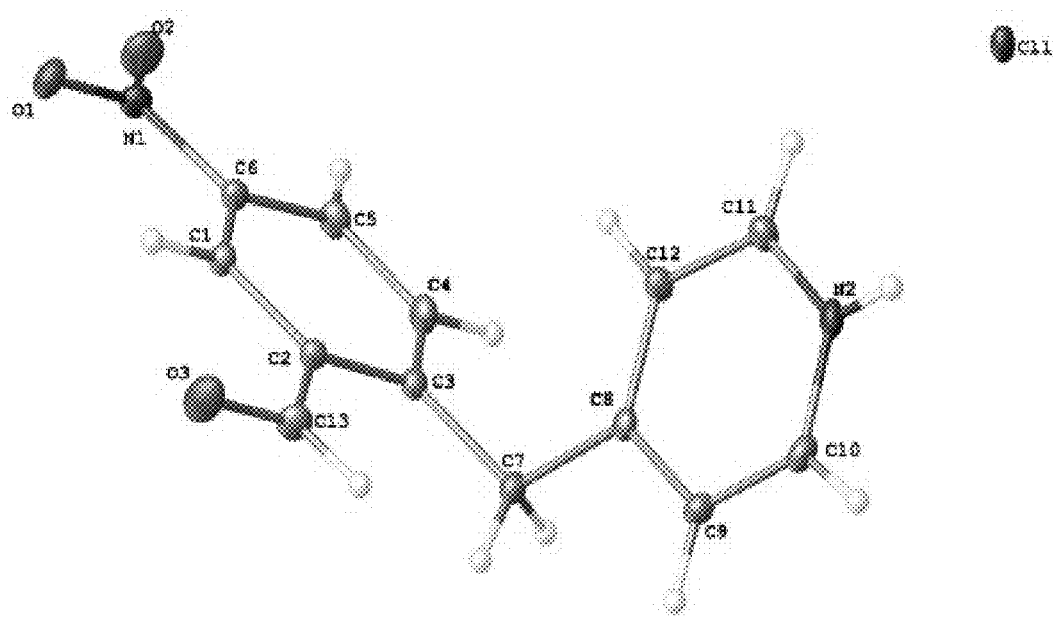
FIG. 4 shows ORTEP Diagram of compound 13.

In order to perform X-ray crystallography, a single crystal of NBP-yde.HCl was grown from the slow generation of HCl in chloroform (as shown in FIG. 4). The action of imidazole on tert-butyldiphenylsilyl chloride (TBDPSCl) at room temperature very slowly generates HCl, which can be trapped by the pyridine functionality. While the formation of a related imidazole trialkylsilane has been reported (Galan, A. A. et al. Tetrahedron Letters 1986, 27, 4995-4998), no report of this practice has been reported in growing HCl-adduct crystals. This method yielded a slow formation of the HCl salt, which gave single crystal x-ray crystallographic quality crystals. HCl adduct single crystals of 4-(4-nitrobenzyl)pyridine may also be grown by this method.

Tert-butyldiphenylsilyl chloride gave the favorable slow formation of crystalline material, while treatment of NBP-yde with trimethylsilyl chloride (TMSCl) resulted in immediate generation of dye and rapid decomposition and precipitation. In addition to producing a slow infusion of HCl, the steric hindrance of TBPSCl thus prevented attack of the silane by the pyridine nitrogen.

Scheme 41: Reaction of NBP-yde with TMSCl

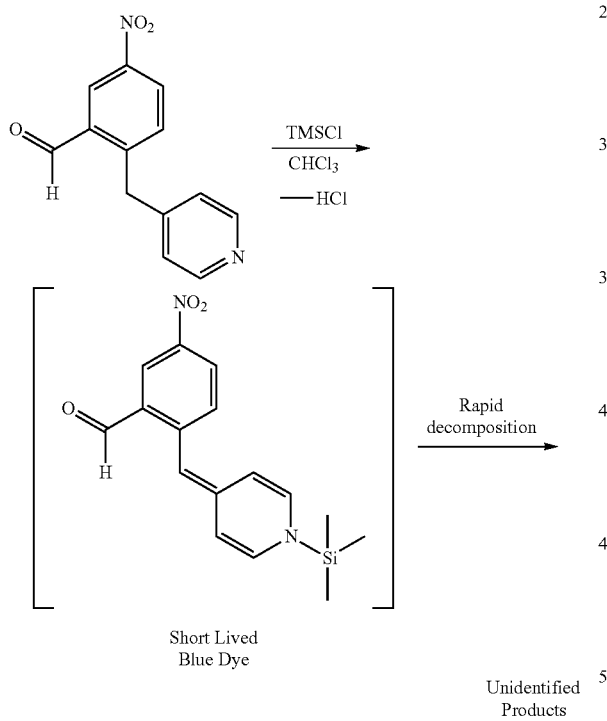

Scheme 42: Over-oxidation of 12

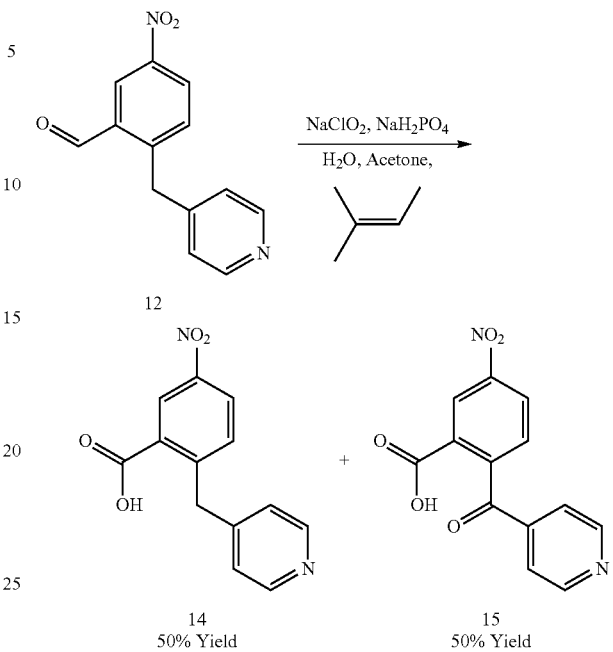

This reaction was optimized to yield the carboxylic acid preferentially by reducing equivalents of sodium chlorite and using less water in the reaction to decrease the solubility of the mono-oxidized product. These efforts led to moderate yields of 76% of the desired carboxylic acid.

Reduction of NBP-yde to NBP-ol proceeded smoothly by treatment with sodium borohydride in ethanol. Fortuitously, the nitro and methylene groups went untouched during the course of this reaction.

Scheme 43: Reduction of an Aldehyde in the Presence of a Nitro Group

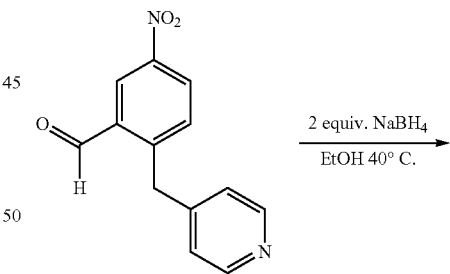

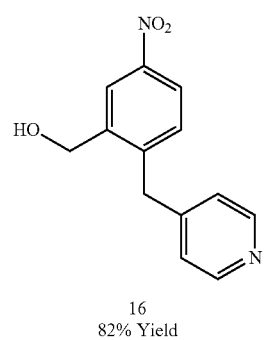

Oxidations/Reductions

To probe the effects of the oxidation state of the carbonyl substituent on NBP-yde, the carboxylic acid and alcohol were prepared by oxidation and reduction of the aldehyde, respectively. The carboxylic acid could not be isolated from oxidation by $KMnO_4$, so a Pinnick oxidation was attempted. Under Pinnick conditions, the carboxylic acid precipitated out cleanly, but one half of the starting material was over-oxidized to the dicarbonyl derivative. Though benzylic oxidations are known to occur with sodium chlorite, generally they also require an additional oxidant like tert-butylhydroperoxide or a transition metal catalyst, so this result was unexpected (Silvestre, S. M. and Salvador, J. A. R. Tetrahedron 2007, 63, 2439-2445).

Additionally, the benzyl imine 17 was generated by condensation of NBP-yde with benzylamine in quantitative yields.
Scheme 44: Imine Formation of 12
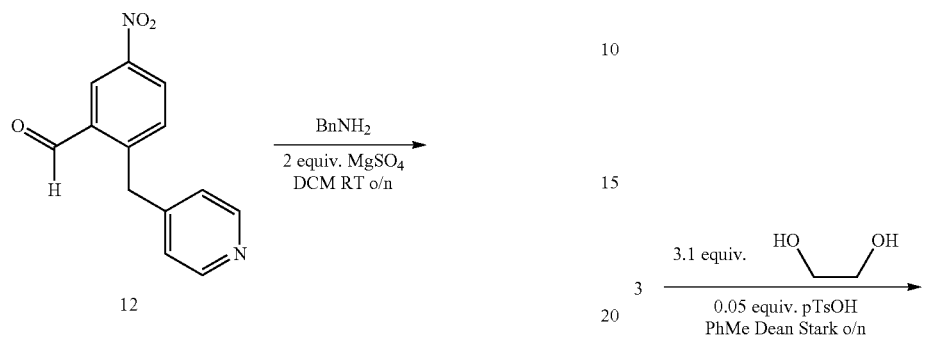
Scheme 45: Summary of synthetic steps to produce a key intermediate and sol-Gel compatible derivative.
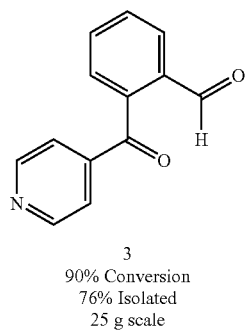
3
90% Conversion
76% Isolated
25 g scale
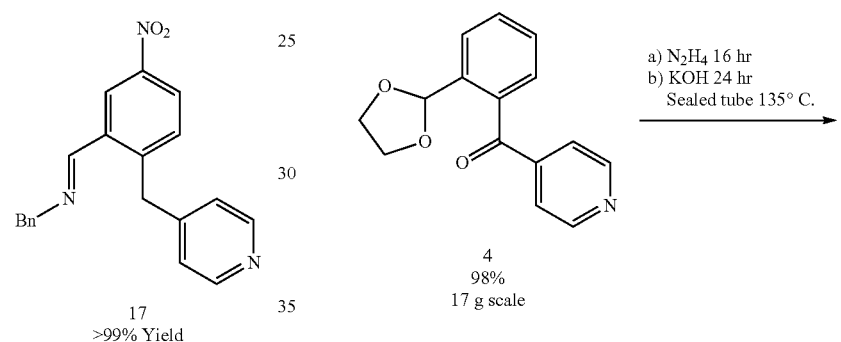
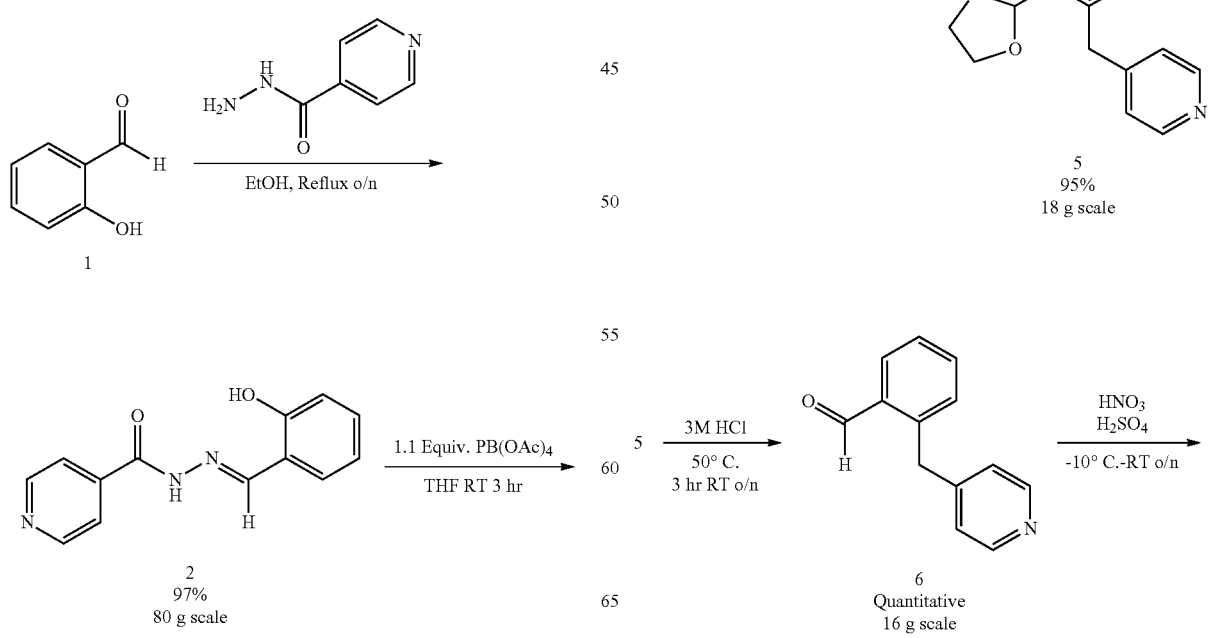

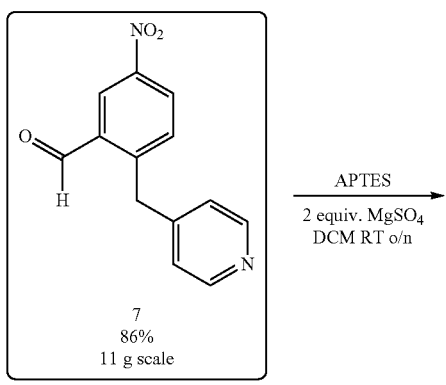
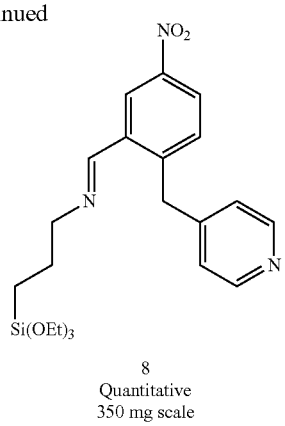
The steps shown above in Scheme 45 are for the specific aldehyde being made. However, as shown below in Scheme 47C that same general synthesis process can serve as the basis for the other compounds. However, the length of time, temperatures and some solvents are likely substituent dependent.
Scheme 46: Summary of further derivatizations.
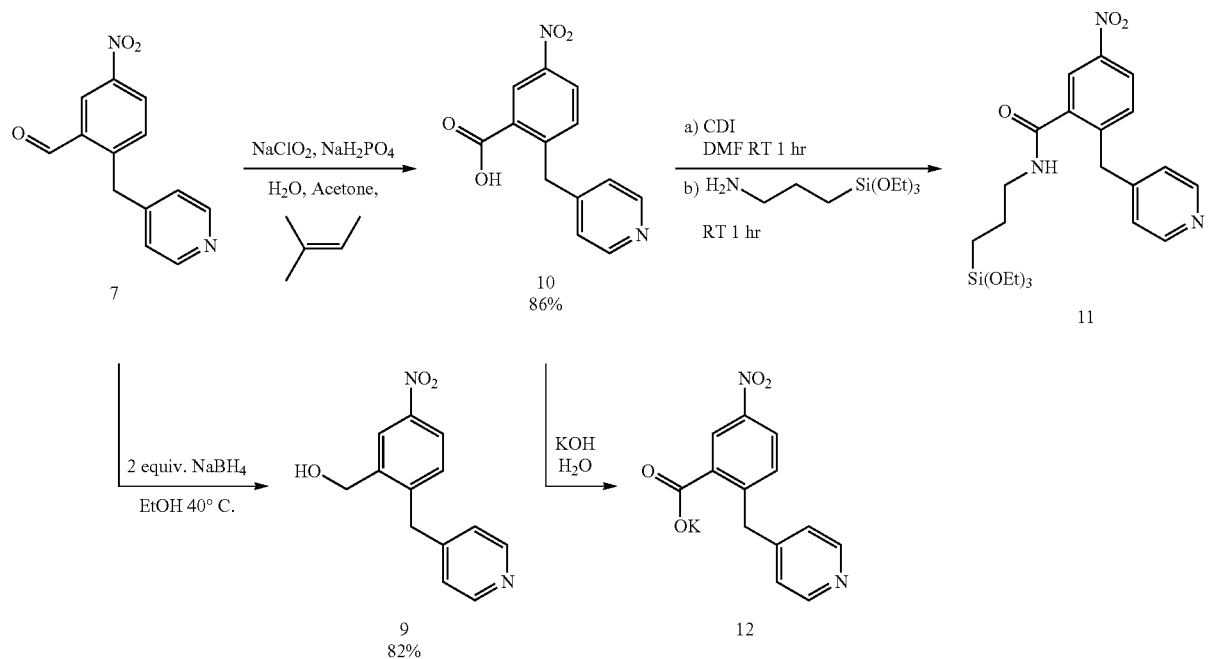

Scheme 47A and B: Two alternative Sol-Gel synthesis A and B.
A
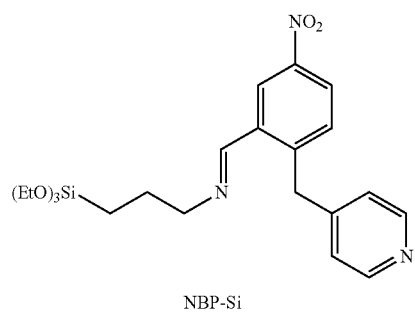
NBP-Si
B
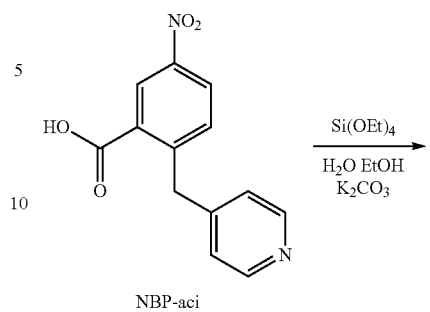
NBP-aci
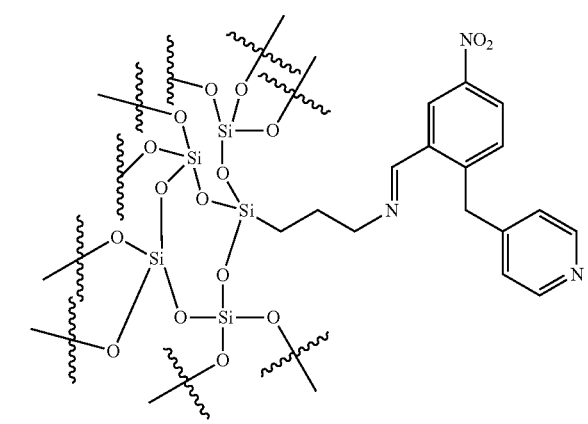
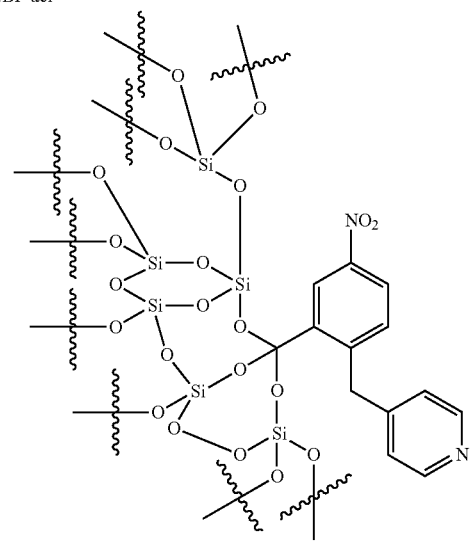
Scheme 47C: Generic Synthesis
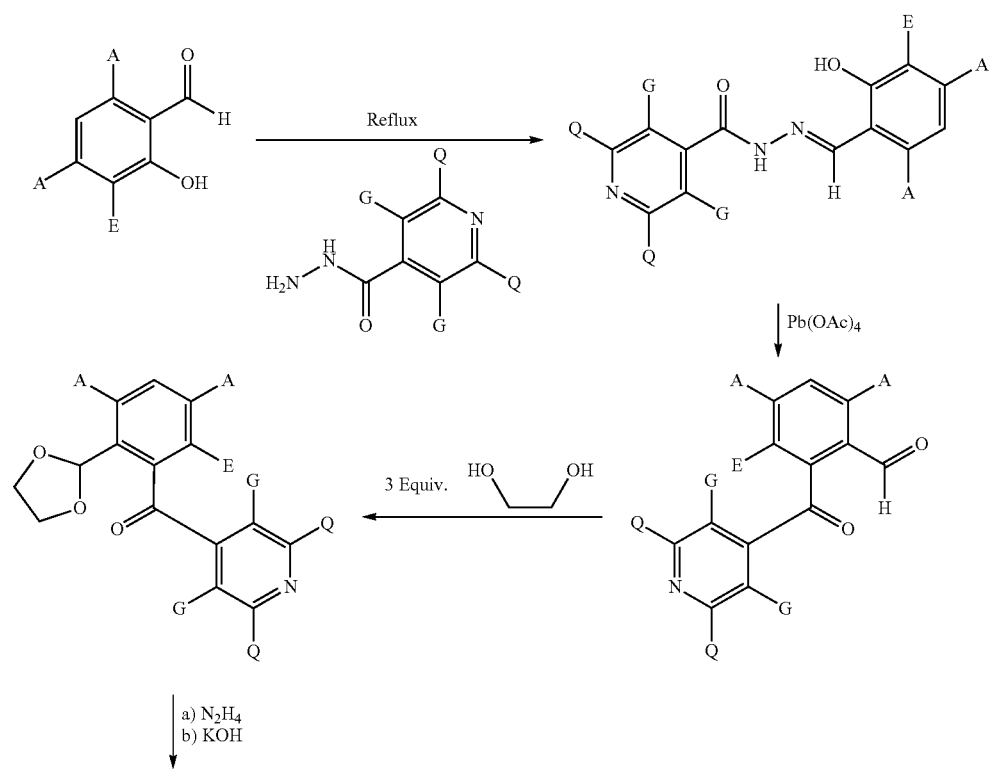

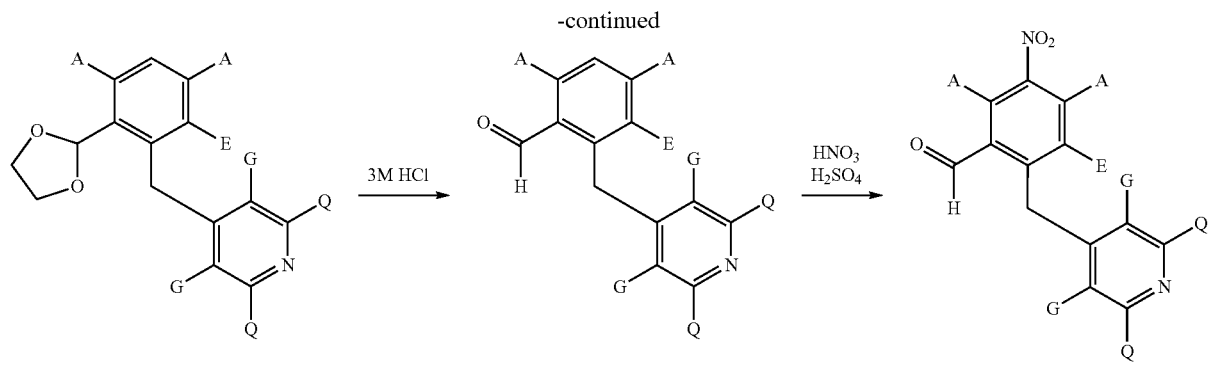

Substitutions at positions A, E, G and Q may be obtained by selecting appropriate substrates having the desired substitutions as set out in Scheme 47C as set out above.

EXAMPLES

Example 1

Assays of NBP and its Derivatives

After the core of the NBP was attained by synthesis, cyclophosphamide was assayed with the varying NBP compounds to compare their molecular sensing capabilities directly with previous results from the parent compound, 4-(4-nitrobenzyl)pyridine. The assay method was modified from a previous report (Christian, R. A. et al. Life Sciences 1980, 27, 2595-2599):

1. Generate a 20-1570 nM (5.22-409.8 ppb) calibration curve of cyclophosphamide in water by serial dilutions and three blanks, with all samples being 1 mL
2. Cool samples to 0° C.
3. Add 1 mL 0.2 M NaOAc buffer pH 4.5
4. Add 0.75 mL 3.3% (w/v) NBP-X in solvent
   a. For NBP, NBP-yde, and NBP-BnIm, solvent was acetone
   b. For NBP-aci, solvent was $H_2O$, with saturated KOH added until the potassium salt dissolved
   c. For NBP-ol, solvent was dimethylformamide
5. The samples were heated to 100° C. for twenty minutes in closed vials
6. After cooling samples to RT, 2.5 mL 1:1 triethylamine:acetone was added
7. Samples were shaken and UV/Vis spectra were taken within an hour Some coloration occurred in the blank samples, so the UV/Vis spectra were taken in scan mode and the blank sample spectra were subtracted from the sample spectra. The method required no avoidance of light or extraction of the dye by organic solvent.

Figure 5:
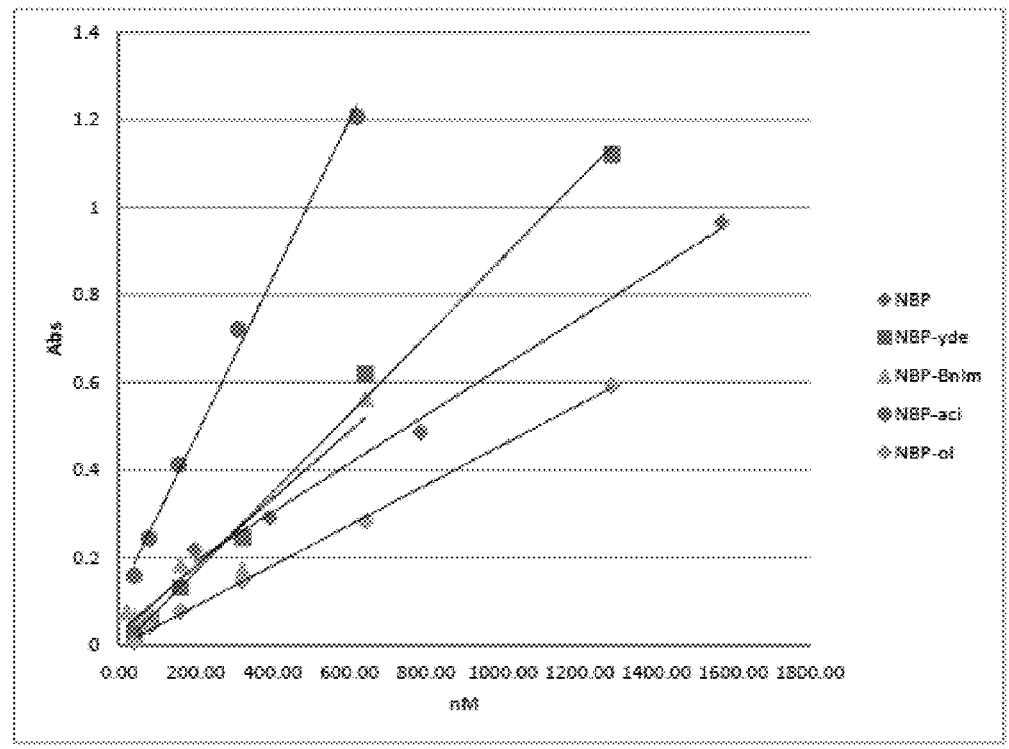
FIG. 5 shows a calibration curves from the assay of cyclophosphamide with NBP and its derivatives.
Figure 6:
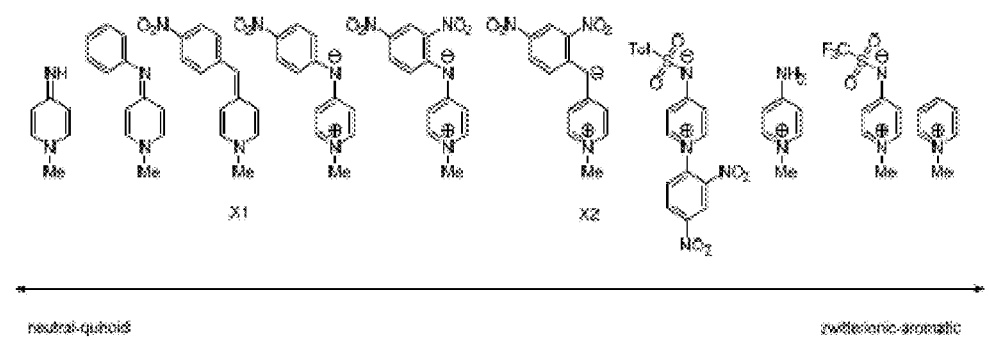
FIG. 6 shows the characterizing of a push-pull chromophore.

As shown in FIG. 5, the NBP compounds differed significantly over the tested series. The molar absorptivities of the dyes resulting from reaction of the NBP series with CP followed the trend NBP-aci>NBP-yde≈NBP-BnIm>NBP≈NBP-ol, as shown below in Error! Reference source not found.

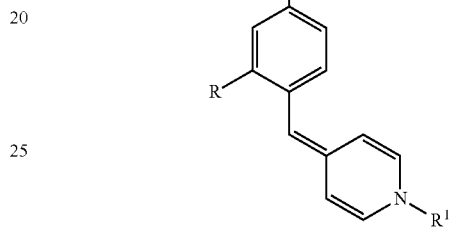

| R = | ε (L $M^{-1}cm^{-1}$) | $\lambda_{anal}$ (nm) |
|---|---|---|
| $CH_2OH$ | 0.46E6 | 570 |
| H | 0.55E6 | 575 |
| CHNBn | 0.77E6 | 581 |
| CHO | 0.89E6 | 587 |
| COOK | 2E6 | 603 |

Error! Reference source not found: Photo-physical Properties of NBP Based Dyes

The analytical wavelength was the wavelength of highest intensity in the 400-700 nm range after all background corrections were made. This wavelength correlated somewhat to the molar absorptivities among the dyes. However, most interesting was the correlation between the identity of the functional group R and the analytical wavelength. Some preliminary calculations predicted that the structures of the dyes should be more twisted at the methine position as the R group became more sterically bulky: this twist would result in a smaller chromophore which would absorb a shorter wavelength, however this rationalization does not fit the experimental trend where the most sterically demanding benzyl imine and carboxylate groups absorbed the longer wavelengths.

In 2001, the Pagani group published a comparison of a wide range of quinoid/zwitterion dyes reproduced in Error! Reference source not found. (Abbotto, A. et al. Org. Chem. 2001, 66, 8883-8892). Utilizing $^{15}N$ and $^{13}C$ NMR spectroscopy they were able to determine the relative neutral-quinoid or zwitterionic-aromatic nature of the dyes across the series. They compared the relative quinoid/aromatic natures of the molecules by determining the anisochrony of the chemical shifts of the heterocycle ring, which arose from greater double bond character of the heterocycle-bridging atom bond. Between X1 and X2, which were most like the compounds studied in this work, the more electron-poor dinitrophenyl ring further stabilized the carbanion, inducing a more zwitterionic/aromatic character. X2 absorbs a longer wavelength than X1, which compares to our results where an electron withdrawing R group lengthened the absorbance wavelength. Stabilization of the carbanion possibly generated a larger chromophore by resonance into the electron-poor benzene ring.

Scheme 48: Relative Wavelength Absorptions of NBP Based Dyes

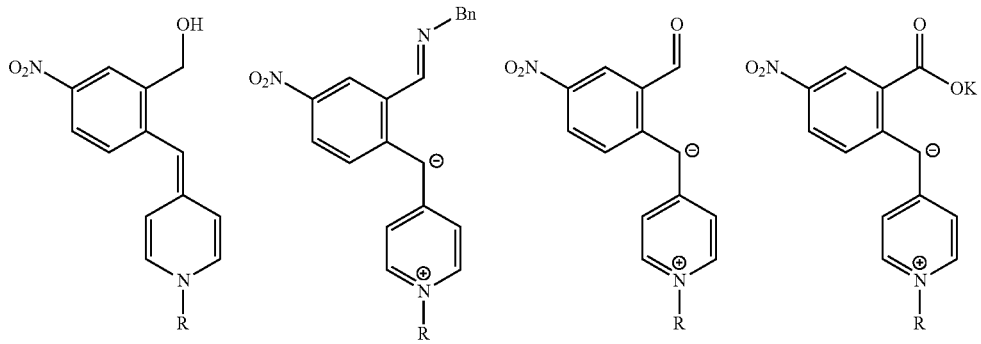

A study of the photophyisics in our system is ongoing. Solvatochromic studies of these compounds suffer from the fact that they are not soluble in the same solvents, and the UV-Vis spectra of the generated dyes give extremely broad absorbances which are difficult to interpret.

TABLE 3

Exemplified Compounds

| Structure | Identifier | Structure | Identifier |
|---|---|---|---|
| 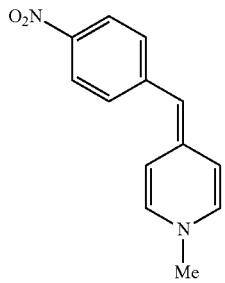 | 4-(4-nitrobenzyl)pyridine (NBP) (prior art compound) | 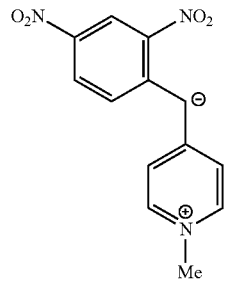 | NBP-aci-K |
| 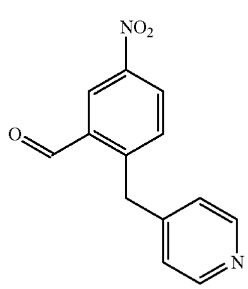 [SMILES: O=Cc1cc([N+](=O)[O-])ccc1Cc1ccncc1] | NBP-yde | 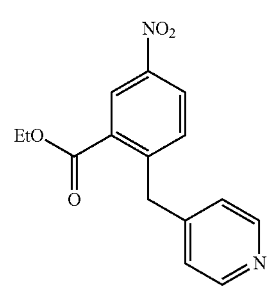 [SMILES: CCOC(=O)c1cc([N+](=O)[O-])ccc1Cc1ccncc1] | ester derivative not yet made, but proposed synthesis provided in Scheme 14 |

TABLE 3-continued

Exemplified Compounds

| Structure | Identifier | Structure | Identifier |
|---|---|---|---|
| (5-nitro-2-(pyridin-4-ylmethyl)benzoic acid) | NBP-aci | (N-benzyl-5-nitro-2-(pyridin-4-ylmethyl)benzamide) | amide proposed in FIG. 1 |
| (5-nitro-2-(pyridin-4-ylmethyl)phenyl)methanol | NBP-ol | (N-benzyl-1-(4-nitro-2-(pyridin-4-ylmethyl)phenyl)methanimine) | NBP-BnIm (imine) (17) |
| (N-(3-(triethoxysilyl)propyl) imine of NBP) | NBP-Si (a) | (N-benzyl-5-nitro-2-(pyridin-4-ylmethyl)benzamide) | |
| (N-(3-(triethoxysilyl)propyl)-5-nitro-2-(pyridin-4-ylmethyl)benzamide) | NBP-Si (b) | | |

Example 2

Installing a Linker and Materials Synthesis

Previously, the 3-aminopropyltriethoxysilane (APTES) linker was installed into 2-iodo-5-nitrobenzoic acid through the acid chloride. Accordingly, it was imagined that the linker could be installed similarly into NBP-aci.

Scheme 49: Silane Linker Installation into 2-iodo-5-nitrobenzoic acid

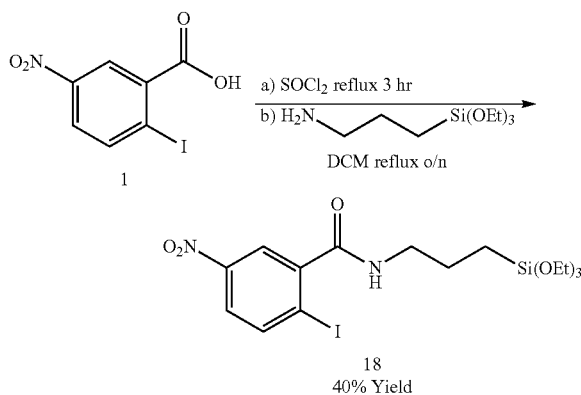

However, upon reflux of NBP-aci in thionyl chloride, apparent oxidation of the benzylic position was observed, which was somewhat surprising, but consistent with our previous results that this benzylic position is sensitive to oxidation. A handful of reports of oxidation by thionyl chloride have been reported (Koenigs, E. and Greiner, H. Ber. dtsch. Chem. Ges. A/B 1931, 64, 1049-1056; Buchi, G. and Lukas, G. J. Am. Chem. Soc. 1964, 86, 5654-5658; Simon, M. S. et al. J. Am. Chem. Soc. 1967, 89, 5838-5844; Cushman, M. and Cheng, L. J. Org. Chem. 1978, 43, 3781-3783; and Valla, A. et al. Synthetic Communications 2006, 36, 3591-3597), but few lead to the direct oxygen installment.

Scheme 50: Apparent Oxidation of 14 in Thionyl Chloride

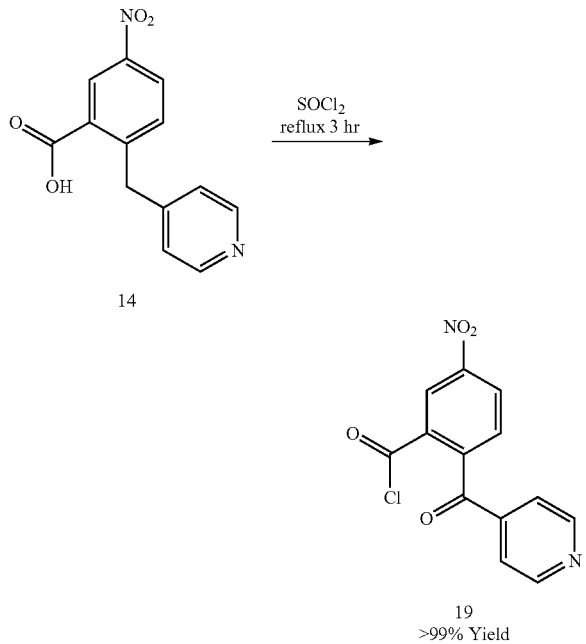

In order to probe this unusual reactivity of the benzylic group on 4-picoline, we tried refluxing other picolines in thionyl chloride after which they were quenched on wet methanol. Similarly, 4-(4-nitrobenzyl)pyridine was oxidized to the diaryl-ketone, however reaction with 4-picoline led to 82% 4-trichloromethylpyridine and 18% methyl isonicotinate as determined by GC/MS. The trichlorination of the 4-picoline methyl group and its subsequent hydrolysis to the carboxylic acid has been reported previously (Davis, M. and Scanlon, D. B. Australian Journal of Chemistry 1977, 30, 433-435; and Kato, T. et al. Tetrahedron 1978, 34, 3445-3449), but the finding that the acid chloride could be trapped into an ester seems novel upon searching the literature. Furthermore, this testing with 4-picoline suggests the mechanism of chlorination/hydrolysis seems to be the likely mechanism of the apparent oxidation of 4-(4-nitrobenzyl) pyridine and NBP-aci.

Scheme 51: Mechanism of Apparent Oxidation of 4-picoline

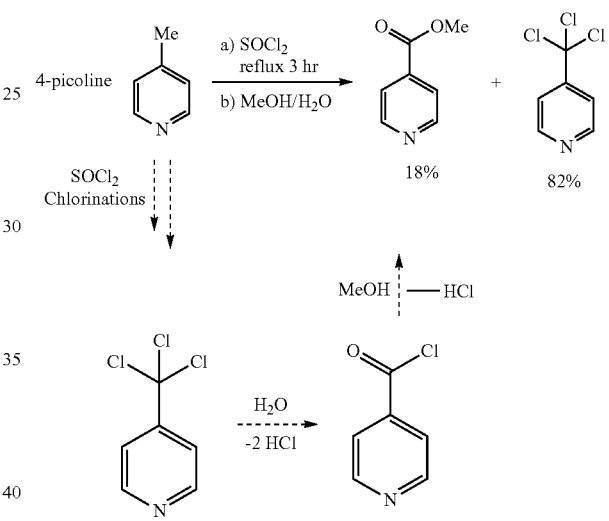

Thus we looked towards gentler amide coupling reactions. Treatment of NBP-aci with carbonyldiimidazole (CDI) at room temperature in dry DMF results in an NBP-aci imidazole complex which underwent amide coupling. The product was observed by mass spectrometry, but decomposed on a silica column.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention.

The invention includes all embodiments and variations substantially as hereinbefore described and with reference to the examples and drawings.

What is claimed is:
1. A compound of Formula 1:

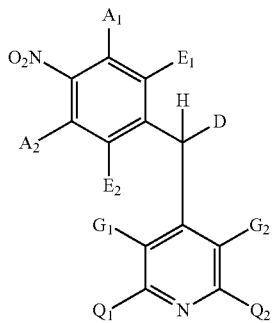

Formula 1 wherein
$A_1$ is selected from H, Me, Et, Pr, Bu, F, Br, I, OH, OJ, OC(O)J, $CF_3$, $CCl_3$, CN, $SO_3H$, C(O)OH, CHO, C(O)OJ, COJ, C(O)OK, C(O)NJ$_2$, C(O)N(J)(H), C(NJ)J, C(S)NH$_2$, C(S)NJ$_2$ and C(S)N(J)(H);
$A_2$ is selected from H, Me, Et, Pr, Bu, F, Br, I, OH, OJ, OC(O)J, $CF_3$, $CCl_3$, CN, $SO_3H$, C(O)OH, CHO, C(O)OJ, COJ, C(O)OK, C(O)NJ$_2$, C(O)N(J)(H), C(NJ)J, C(S)NH$_2$, C(S)NJ$_2$ and C(S)N(J)(H);
$E_1$ is selected from H, Me, Et, Pr, Bu, F, Br, I, OH, OL, OC(O)L, $CF_3$, $CCl_3$, CN, $SO_3H$, C(O)OH, CHO, $CH_2OH$, C(O)OL, COL, C(O)OK, C(O)NL$_2$, C(O)N(L)(H), C=NL, C(NL)L, C(S)NH$_2$, C(S)NL$_2$ and C(S)N(L)(H);
$E_2$ is selected from H, Me, Et, Pr, Bu, F, Br, I, OH, OL, OC(O)L, $CF_3$, $CCl_3$, CN, $SO_3H$, C(O)OH, CHO, $CH_2OH$, C(O)OL, COL, C(O)OK, C(O)NL$_2$, C(O)N(L)(H), C=NL, C(NL)L, C(S)NH$_2$, C(S)NL$_2$ and C(S)N(L)(H);
D is selected from H, Et, n-Pr, c-Pr, Bu, Cl, Br, I, OT$^b$, OC(O)T$^b$, NO$_2$, CF$_3$, CCl$_3$, CN, SO$_3$H, C(O)OH, CHO, C(O)OT$^a$, COT$^b$, C(O)OK, C(O)NT$^b{}_2$, C(O)N(T$^b$)(H), C(NT$^b$)T$^b$, C(S)NH$_2$, C(S)NT$^b{}_2$ and C(S)N(T$^b$)(H);
$G_1$ is selected from H, Et, Pr, Bu, F, Cl, Br, I, OH, OM$^a$, OC(O)M$^a$, NO$_2$, CF$_3$, CCl$_3$, CN, SO$_3$H, C(O)OH, CHO, C(O)OM$^a$, COM$^a$, C(O)OK, C(O)NM$^a{}_2$, C(O)N(M$^a$)(H), C(NM$^a$)M$^a$, C(S)NH$_2$, C(S)NM$^a{}_2$ and C(S)N(M$^a$)(H);
$G_2$ is selected from H, Et, Pr, Bu, F, Cl, Br, I, OH, OM$^a$, OC(O)M$^a$, NO$_2$, CF$_3$, CCl$_3$, CN, SO$_3$H, C(O)OH, CHO, C(O)OM$^a$, COM$^a$, C(O)OK, C(O)NM$^a{}_2$, C(O)N(M$^a$)(H), C(NM$^a$)M$^a$, C(S)NH$_2$, C(S)NM$^a{}_2$ and C(S)N(M$^a$)(H);
$Q_1$ is selected from H, Et, Pr, Bu, Br, I, OH, OM$^b$, OC(O)M$^b$, NO$_2$, CCl$_3$, SO$_3$H, C(O)OH, CHO, C(O)OM$^b$, COM$^b$, C(O)OK, C(O)NM$^c{}_2$, C(O)N(M$^d$)(H), and C(NM$^b$)M$^b$;
$Q_2$ is selected from H, Et, Pr, Bu, Br, I, OH, OM$^b$, OC(O)M$^b$, NO$_2$, CCl$_3$, SO$_3$H, C(O)OH, CHO, C(O)OM$^b$, COM$^b$, C(O)OK, C(O)NM$^c{}_2$, C(O)N(M$^d$)(H), and C(NM$^b$)M$^b$;
provided that at least one of $A_1$, $A_2$, $E_1$, $E_2$, D, $G_1$, $G_2$, $Q_1$ and $Q_2$ is other than H;

J is independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H;
K is potassium;
L is independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H;
$T^a$ is independently selected from a 1, or 3-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, COSH, NO$_2$, or SO$_3$H;
$T^b$ is independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H;
$M^a$ is independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H;
$M^b$ may be independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H;
$M^c$ is independently selected from a 1-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H; and
$M^d$ may be independently selected from a 2-20 carbon alkyl, 1-20 carbon aryl or 1-20 carbon alkenyl group, optionally substituted with one or more of: =O, =S, OH, SH, NH$_2$, I, Br, Cl, F, CN, C(O)OH, CHO, C(O)NH$_2$, C(O)SH, NO$_2$, or SO$_3$H.
2. The compound of claim 1, wherein
$A_1$ is selected from H, Me, Et, Pr, Bu, F, Br, I, OJ, OC(O)J, CF$_3$, CCl$_3$, CN, SO$_3$H, C(O)OH, CHO, C(O)OJ, COJ, C(O)OK, C(O)NJ$_2$, C(O)N(J)(H), C(NJ)J, C(S)NH$_2$, C(S)NJ$_2$ and C(S)N(J)(H);
$A_2$ is selected from H, Me, Et, Pr, Bu, F, Br, I, OJ, OC(O)J, CF$_3$, CCl$_3$, CN, SO$_3$H, C(O)OH, CHO, C(O)OJ, COJ, C(O)OK, C(O)NJ$_2$, C(O)N(J)(H), C(NJ)J, C(S)NH$_2$, C(S)NJ$_2$ and C(S)N(J)(H);
$E_1$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H), C=NL, C(NL)L, C(S)NH$_2$, C(S)NL$_2$ and C(S)N(L)(H);
$E_2$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H), C=NL, C(NL)L, C(S)NH$_2$, C(S)NL$_2$ and C(S)N(L)(H);
D is selected from H, Cl, Br, I, OC(O)T$^b$, NO$_2$, CF$_3$, CCl$_3$, CN, SO$_3$H, C(O)OH, CHO, C(O)OT$^a$, COT$^b$, C(O)OK, C(O)NT$^b{}_2$, C(O)N(T$^b$)(H), C(NT$^b$)T$^b$, C(S)NH$_2$, C(S)NT$^b{}_2$ and C(S)N(T$^b$)(H);
$G_1$ is selected from H, F, Cl, Br, I, NO$_2$, CF$_3$, CCl$_3$, CN, SO$_3$H, C(O)OH, CHO, OC(O)M$^a$, C(O)OM$^a$, COM$^a$, C(O)OK, C(O)NM$^a{}_2$, C(O)N(M$^a$)(H), C(NM$^a$)M$^a$, C(S)NH$_2$, C(S)NM$^a{}_2$ and C(S)N(M$^a$)(H);

$G_2$ is selected from H, Et, Pr, Bu, F, Cl, Br, I, OH, $NO_2$, $CF_3$, $CCl_3$, CN, $SO_3H$, C(O)OH, CHO, $OC(O)M^a$, $C(O)OM^a$, $COM^a$, C(O)OK, $C(O)NM^a_2$, $C(O)N(M^a)$(H), $C(NM^a)M^a$, $C(S)NH_2$, $C(S)NM^a_2$ and $C(S)N(M^a)$(H);

$Q_1$ is selected from H, Et, Pr, Bu, Br, I, OH, $OM^b$ $NO_2$;

$Q_2$ is selected from H, Et, Pr, Bu, Br, I, OH, $OM^b$ and $NO_2$;

J is independently selected from a 1-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, C(O)SH or $SO_3H$;

L is independently selected from a 1-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, C(O)SH or $SO_3H$;

$T^a$ is independently selected from a 1, or 3-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, COSH or $SO_3H$;

$T^b$ is independently selected from a 1-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, C(O)SH or $SO_3H$;

$M^a$ is independently selected from a 1-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, C(O)SH or $SO_3H$;

$M^b$ may be independently selected from a 1-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, C(O)SH or $SO_3H$;

$M^c$ is independently selected from a 1-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, C(O)SH or $SO_3H$; and $M^d$ may be independently selected from a 2-20 carbon alkyl, 1-20 carbon aryl or 1-20 carbon alkenyl group, optionally substituted with one or more of: =O, =S, OH, SH, $NH_2$, CN, C(O)OH, CHO, $C(O)NH_2$, C(O)SH or $SO_3H$.

3. The compound of claim 1, wherein $A_1$ is selected from H, Me, Et, Pr, Bu, F, Br, I, OJ, OC(O)J, $CF_3$, $CCl_3$, CN, $SO_3H$, C(O)OH, CHO, C(O)OJ, COJ, C(O)OK, $C(O)NJ_2$, C(O)N(J)(H) and C(NJ)J;

$A_2$ is selected from H, Me, Et, Pr, Bu, F, Br, I, OJ, OC(O)J, $CF_3$, $CCl_3$, CN, $SO_3H$, C(O)OH, CHO, C(O)OJ, COJ, C(O)OK, $C(O)NJ_2$, C(O)N(J)(H) and C(NJ)J;

$E_1$ is selected from H, Br, I, OC(O)L, $CF_3$, $CCl_3$, CN, $SO_3H$, C(O)OH, CHO, $CH_2OH$, C(O)OL, COL, C(O)OK, $C(O)NL_2$, C(O)N(L)(H), C=NL and C(NL)L;

$E_2$ is selected from H, F, Br, I, OC(O)L, $CF_3$, $CCl_3$, CN, $SO_3H$, C(O)OH, CHO, $CH_2OH$, C(O)OL, COL, C(O)OK, $C(O)NL_2$, C(O)N(L)(H), C=NL and C(NL)L;

D is selected from H, Cl, Br, $OC(O)T^b$, $NO_2$, $CF_3$, $CCl_3$, CN, $SO_3H$, C(O)OH, CHO, $C(O)OT^a$, $COT^b$, C(O)OK, $C(O)NT^b_2$, $C(O)N(T^b)$(H) and $C(NT^b)T^b$;

$G_1$ is selected from H, F, Cl, Br, I, $NO_2$, $CF_3$, $CCl_3$, CN, $SO_3H$, C(O)OH, CHO, $OC(O)M^a$, $C(O)OM^a$, $COM^a$, C(O)OK, $C(O)NM^a_2$, $C(O)N(M^a)$(H) and $C(NM^a)M^a$;

$G_2$ is selected from H, F, Cl, Br, I, $NO_2$, $CF_3$, $CCl_3$, CN, $SO_3H$, C(O)OH, CHO, $OC(O)M^a$, $C(O)OM^a$, $COM^a$, C(O)OK, $C(O)NM^a_2$, $C(O)N(M^a)$(H) and $C(NM^a)M^a$;

$Q_1$ is selected from H, Et, Pr, Bu, OH, $OM^b$ and $NO_2$;

$Q_2$ is selected from H, Et, Pr, Bu, OH, $OM^b$ and $NO_2$;

J is independently selected from a 1-20 carbon alkyl, 1-20 carbon aryl or 1-20 carbon alkenyl group, optionally substituted with one or more of: =O, =OH, SH, $NH_2$, CN, C(O)OH, CHO, $C(O)NH_2$ or $SO_3H$;

L is independently selected from a 1-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$;

$T^a$ is independently selected from a 1, or 3-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$;

$T^b$ is independently selected from a 1-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$;

$M^a$ is independently selected from a 1-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$;

$M^b$ may be independently selected from a 1-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$;

$M^c$ is independently selected from a 1-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$; and $M^d$ may be independently selected from a 2-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$.

4. The compound of claim 1, wherein $A_1$ is selected from H, Me, Et, Pr, Bu, F, Br and I;

$A_2$ is selected from H, Me, Et, Pr, Bu, F, Br and I;

$E_1$ is selected from H, F, Br, I, OC(O)L, $CF_3$, $CCl_3$, CN, $SO_3H$, C(O)OH, CHO, $CH_2OH$, C(O)OL, COL, C(O)OK, $C(O)NL_2$, C(O)N(L)(H) and C=NL;

$E_2$ is selected from H, F, Br, I, OC(O)L, $CF_3$, $CCl_3$, CN, $SO_3H$, C(O)OH, CHO, $CH_2OH$, C(O)OL, COL, C(O)OK, $C(O)NL_2$, C(O)N(L)(H) and C=NL;

D is selected from H, Cl, Br, $OC(O)T^b$, $NO_2$, $CF_3$, $CCl_3$, CN, $SO_3H$, C(O)OH, CHO, $C(O)OT^a$, $COT^b$ and C(O)OK;

$G_1$ is selected from H, F, Cl, Br, I, $NO_2$, $CF_3$, $CCl_3$, CN, $SO_3H$, C(O)OH, CHO, $OC(O)M^a$, $C(O)OM^a$, $COM^a$ and C(O)OK;

$G_2$ is selected from H, F, Cl, Br, I, $NO_2$, $CF_3$, $CCl_3$, CN, $SO_3H$, C(O)OH, CHO, $OC(O)M^a$, $C(O)OM^a$, $COM^a$ and C(O)OK;

$Q_1$ is selected from H, Et, Pr, Bu and OH;

$Q_2$ is selected from H, Et, Pr, Bu and OH;

J is independently selected from a 1-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$;

L is independently selected from a 1-20 carbon alkyl, 1-20 carbon aryl or 1-20 carbon alkenyl group, optionally substituted with one or more of: =O, OH, SH, $NH_2$, CN, C(O)OH, CHO, $C(O)NH_2$ or $SO_3H$;

$T^a$ is independently selected from a 1, or 3-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H;

T$^b$ is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H;

M$^a$ is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H;

M$^b$ is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H;

M$^c$ is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H; and M$^d$ is independently selected from a 2-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

5. The compound of claim 1, wherein

A$_1$ is H;

A$_2$ is H;

E$_1$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

E$_2$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

D is selected from H, Cl, Br, OC(O)T$^b$, NO$_2$, CF$_3$, CCl$_3$, CN, SO$_3$H, C(O)OH, CHO, C(O)OT$^a$, COT$^b$ and C(O)OK;

G$_1$ is selected from H, F, Cl, Br, I, NO$_2$, CF$_3$, CCl$_3$, CN, SO$_3$H, C(O)OH and CHO;

G$_2$ is selected from H, F, Cl, Br, I, NO$_2$, CF$_3$, CCl$_3$, CN, SO$_3$H, C(O)OH and CHO;

Q$_1$ is H;

Q$_2$ is H;

L is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H;

T$^a$ is independently selected from a 1, or 3-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H; and T$^b$ is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

6. The compound of claim 1, wherein

A$_1$ is H;

A$_2$ is H;

E$_1$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

E$_2$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

D is selected from H, Cl, Br, OC(O)T$^b$, NO$_2$, CF$_3$, CCl$_3$, CN, SO$_3$H, C(O)OH, CHO, C(O)OT$^a$, COT$^b$ and C(O)OK;

G$_1$ is selected from H, F, Cl, Br, I, NO$_2$, CF$_3$, CCl$_3$ and CN;

G$_2$ is selected from H, F, Cl, Br, I, NO$_2$, CF$_3$, CCl$_3$ and CN;

Q$_1$ is H;

Q$_2$ is H;

L is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H;

T$^a$ is independently selected from a 1, or 3-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H; and T$^b$ is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

7. The compound of claim 1, wherein

A$_1$ is H;

A$_2$ is H;

E$_1$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

E$_2$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

D is selected from H, Cl, Br, NO$_2$, CF$_3$, CCl$_3$, CN, SO$_3$H, C(O)OH and CHO;

G$_1$ is H;

G$_2$ is H;

Q$_1$ is H;

Q$_2$ is H; and

L is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

8. The compound of claim 1, wherein

A$_1$ is H;

A$_2$ is H;

E$_1$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

E$_2$ is selected from H, F, Br, I, OC(O)L, CF$_3$, CCl$_3$, CN, SO$_3$H, C(O)OH, CHO, CH$_2$OH, C(O)OL, COL, C(O)OK, C(O)NL$_2$, C(O)N(L)(H) and C=NL;

D is H,

G$_1$ is H;

G$_2$ is H;

Q$_1$ is H;

Q$_2$ is H; and

L is independently selected from a 1-20 carbon alkyl, 1-20 carbon aryl or 1-20 carbon alkenyl group, optionally substituted with one or more of: =O, OH, SH, NH$_2$, CN, C(O)OH, CHO, C(O)NH$_2$ or SO$_3$H.

9. The compound of claim 1, wherein

A$_1$ is H;

A$_2$ is H;

E$_1$ is selected from H, CHO, CH$_2$OH, C(O)OL, C(O)OK, C(O)N(L)(H) and C=NL;

E$_2$ is selected from H, CHO, CH$_2$OH, C(O)OL, C(O)OK, C(O)N(L)(H) and C=NL;

D is H;

G₁ is H;

G₂ is H;

Q₁ is H;

Q₂ is H; and

L is independently selected from a 1-20 carbon alkyl, 1-20 carbon aryl or 1-20 carbon alkenyl group, optionally substituted with one or more of: =O, OH, SH, NH₂, CN, C(O)OH, CHO, C(O)NH₂ or SO₃H.

10. The compound of claim 1, wherein the compound is selected from:

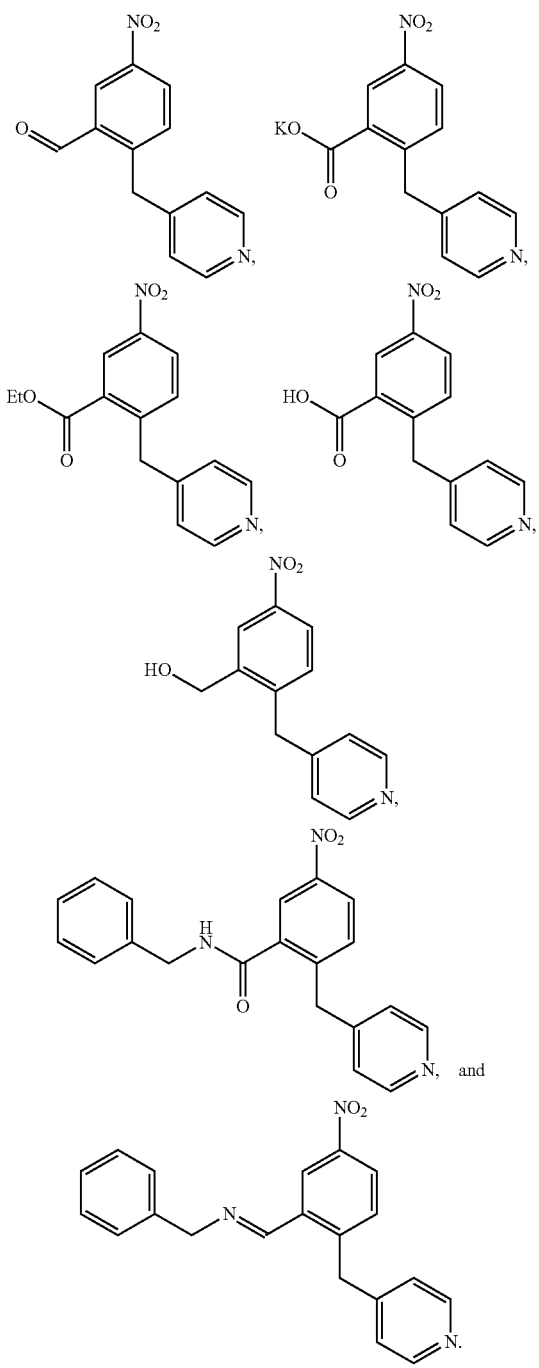

11. A compound of Formula 1:

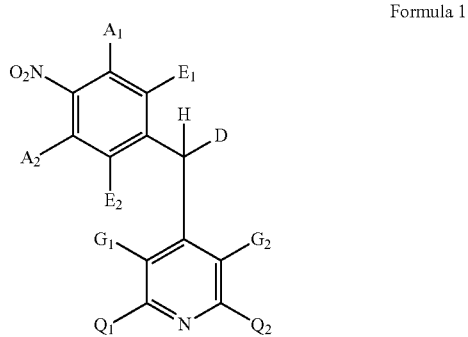

Formula 1 wherein

A₁ is selected from H, Me, Et, Pr, Bu, F, Cl, Br, I, OH, $OR^A$, $OC(O)R^A$, $NO_2$, $CF_3$, $CCl_3$, CN, $SO_3H$, CHO, $CH_2OH$, $C(O)OR^A$, $COR^A$, C(O)OK, $C(O)NR^A_2$, $C(O)N(R^A)(H)$, $C=NR^A$, $C(NR)R^A$, $C(S)NH_2$, $C(S)NR^A_2$, $C(S)N(R^A)(H)$,

[structures with OH, $O-X_1-Z_1$, $X_2-Z_2$, $NH-X_3-Z_3$, and $N-X_4-Z_4$]

A₂ is selected from H, Me, Et, Pr, Bu, F, Cl, Br, I, OH, $OR^A$, $OC(O)R^A$, $NO_2$, $CF_3$, $CCl_3$, CN, $SO_3H$, CHO, $CH_2OH$, $C(O)OR^A$, $COR^A$, C(O)OK, $C(O)NR^A_2$, $C(O)N(R^A)(H)$, $C=NR^A$, $C(NR)R^A$, $C(S)NH_2$, $C(S)NR^A_2$, $C(S)N(R^A)(H)$,

[structures with OH, $O-X_1-Z_1$, $X_2-Z_2$, $NH-X_3-Z_3$, and $N-X_4-Z_4$]

E₁ is selected from H, Me, Et, Pr, Bu, F, Cl, Br, I, OH, $OR^E$, $OC(O)R^E$, $NO_2$, $CF_3$, $CCl_3$, CN, $SO_3H$, CHO, $CH_2OH$, $C(O)OR^E$, $COR^E$, C(O)OK, $C(O)NR^E_2$, $C(O)N(R^E)(H)$, $C=NR^E$, $C(NR^E)R^E$, $C(S)NH_2$, $C(S)NR^E_2$, $C(S)N(R^E)(H)$,

[structures with OH, $O-X_1-Z_1$, $X_2-Z_2$,]

-continued

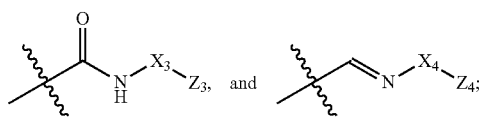

$E_2$ is selected from H, Me, Et, Pr, Bu, F, Cl, Br, I, OH, $OR^E$, $OC(O)R^E$, $NO_2$, $CF_3$, $CCl_3$, CN, $SO_3H$, CHO, $CH_2OH$, $C(O)OR^E$, $COR^E$, C(O)OK, $C(O)NR^E{}_2$, $C(O)N(R^E)(H)$, $C{=}NR^E$, $C(NR^E)R^E$, $C(S)NH_2$, $C(S)NR^E{}_2$, $C(S)N(R^E)(H)$,

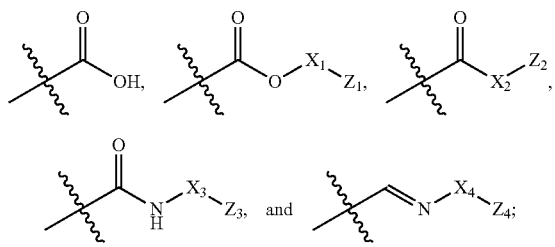

D is selected from H, Me, Et, Pr, Bu, F, Cl, Br, I, OH, $OR^D$, $OC(O)R^D$, $NO_2$, $CF_3$, $CCl_3$, CN, $SO_3H$, CHO, $CH_2OH$, $COOR^D$, $COR^D$, C(O)OK, $C(O)NR^D{}_2$, $C(O)N(R^D)(H)$, $C{=}NR^D$, $C(NR^D)R^D$, $C(S)NH_2$, $C(S)NR^D{}_2$, $C(S)N(R^D)(H)$,

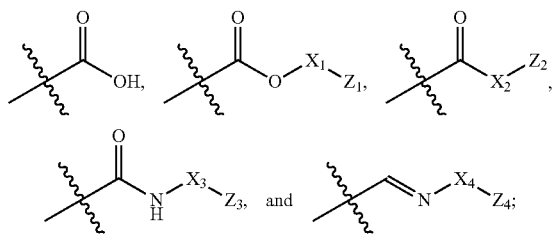

$G_1$ is selected from H, Me, Et, Pr, Bu, F, Cl, Br, I, OH, $OR^G$, $OC(O)R^G$, $NO_2$, $CF_3$, $CCl_3$, CN, $SO_3H$, CHO, $CH_2OH$, $C(O)OR^G$, $COR^G$, C(O)OK, $C(O)NR^G{}_2$, $C(O)N(R^G)(H)$, $C{=}NR^G$, $C(NR^G)R^G$, $C(S)NH_2$, $C(S)NR^G{}_2$, $C(S)N(R^G)(H)$,

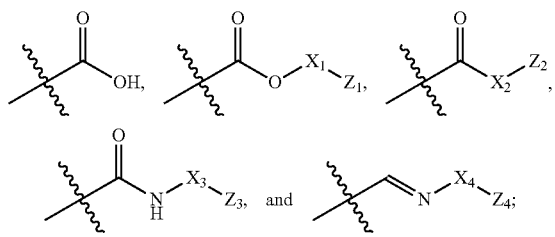

$G_2$ is selected from H, Me, Et, Pr, Bu, F, Cl, Br, I, OH, $OR^G$, $OC(O)R^G$, $NO_2$, $CF_3$, $CCl_3$, CN, $SO_3H$, CHO, $CH_2OH$, $C(O)OR^G$, $COR^G$, C(O)OK, $C(O)NR^G{}_2$, $C(O)N(R^G)(H)$, $C{=}NR^G$, $C(NR^G)R^G$, $C(S)NH_2$, $C(S)N(R^G)(H)$,

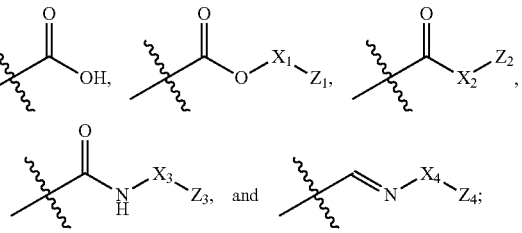

$Q_1$ is selected from H, Me, Et, Pr, Bu, F, Cl, Br, I, OH, $OR^Q$, $OC(O)R^Q$, $NO_2$, $CF_3$, $CCl_3$, CN, $SO_3H$, CHO, $CH_2OH$, $C(O)OR^Q$, $COR^Q$, C(O)OK, $C(O)NR^Q{}_2$, $C(O)N(R^Q)(H)$, $C{=}NR^Q$, $C(NR^Q)R^Q$, $C(S)NH_2$, $C(S)NR^Q{}_2$, $C(S)N(R^Q)(H)$,

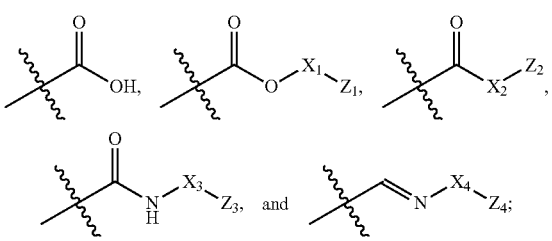

$Q_2$ is selected from H, Me, Et, Pr, Bu, F, Cl, Br, I, OH, $OR^Q$, $OC(O)R^Q$, $NO_2$, $CF_3$, $CCl_3$, CN, $SO_3H$, CHO, $CH_2OH$, $C(O)OR^Q$, $COR^Q$, C(O)OK, $C(O)NR^Q{}_2$, $C(O)N(R^Q)(H)$, $C{=}NR^Q$, $C(NR^Q)R^Q$, $C(S)NH_2$, $C(S)NR^Q{}_2$, $C(S)N(R^Q)(H)$,

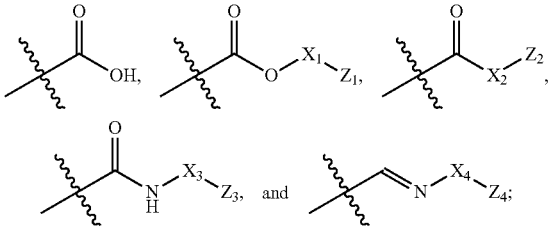

provided that at least one of $A_1$, $A_2$, $E_1$, $E_2$, D, $G_1$, $G_2$, $Q_1$, $Q_2$ is

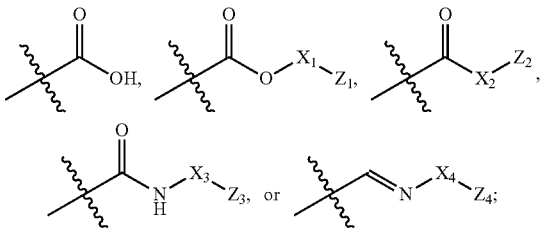

and wherein,
$X_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;
$X_2$ is a 1-20 carbon, saturated or unsaturated hydrocarbyl chain, or an ether group having the structure R—O—

R', wherein the hydrocarbyl chain or the ether group is optionally substituted by OH, F, Cl, Br, I, or $NR_3$;

$X_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$X_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$Z_1$ is selected from $SiR_3$, $Si(OR)_3$, OH, NH, SH, aryl, C(O)OH, C(O)O$^-$, $NR_2$, or NHR;

$Z_2$ is selected from $SiR_3$, $Si(OR)_3$, OH, NH, SH, aryl, C(O)OH, C(O)O$^-$, $NR_2$, or NHR;

$Z_3$ is selected from $SiR_3$, $Si(OR)_3$, OH, NH, SH, aryl, C(O)OH, C(O)O$^-$, $NR_2$, or NHR;

$Z_4$ is selected from $SiR_3$, $Si(OR)_3$, OH, NH, SH, aryl, C(O)OH, C(O)O$^-$, $NR_2$, or NHR;

K is potassium;

$R^A$ is a 1-20 carbon alkyl, 1-20 carbon aryl or 1-20 carbon alkenyl group, optionally substituted with one or more of: =O, =S, —OH, —SH, —$NH_2$, —I, Br, —Cl, —F, —CN, —C(O)OH, —CHO, —$CONH_2$, —COSH, —$NO_2$, or —$SO_3H$;

$R^E$ is a 1-20 carbon alkyl, 1-20 carbon aryl or 1-20 carbon alkenyl group, optionally substituted with one or more of: =O, =S, —OH, —SH, —$NH_2$, —I, Br, —Cl, —F, —CN, —C(O)OH, —CHO, —$CONH_2$, —COSH, —$NO_2$, or —$SO_3H$;

$R^D$ is a 1-20 carbon alkyl, 1-20 carbon aryl or 1-20 carbon alkenyl group, optionally substituted with one or more of: =O, =S, —OH, —SH, —$NH_2$, —I, Br, —Cl, —F, —CN, —C(O)OH, —CHO, —$CONH_2$, —COSH, —$NO_2$, or —$SO_3H$;

$R^G$ is a 1-20 carbon alkyl, 1-20 carbon aryl or 1-20 carbon alkenyl group, optionally substituted with one or more of: =O, =S, —OH, —SH, —$NH_2$, —I, Br, —Cl, —F, —CN, —C(O)OH, —CHO, —$CONH_2$, —COSH, —$NO_2$, or —$SO_3H$;

$R^Q$ is a 1-20 carbon alkyl, 1-20 carbon aryl or 1-20 carbon alkenyl group, optionally substituted with one or more of: =O, =S, —OH, —SH, —$NH_2$, —I, Br, —Cl, —F, —CN, —C(O)OH, —CHO, —$CONH_2$, —COSH, —$NO_2$, or —$SO_3H$; and R and R' are a 1-10 carbon alkyl or 1-10 carbon aryl, optionally substituted with one or more of: =O, =S, —OH, —SH, —I, Br, —Cl, —F, —CN, —C(O)OH, —CHO, —$CONH_2$, —COSH, —$NO_2$, or —$SO_3H$.

12. The compound of claim 11, wherein $A_1$ is selected from H, Me, Et, Pr, Bu, F, Cl, Br, I, OH, $OR^A$, $OC(O)R^A$, $NO_2$, $CF_3$, $CCl_3$, CN, $SO_3H$, CHO, $CH_2OH$, $C(O)OR^A$, $COR^A$, C(O)OK, $C(O)NR^A_2$, $C(O)N(R^A)(H)$, C=$NR^A$, $C(NR)R^A$, $C(S)NH_2$, $C(S)NR^A_2$, $C(S)N(R^A)(H)$,

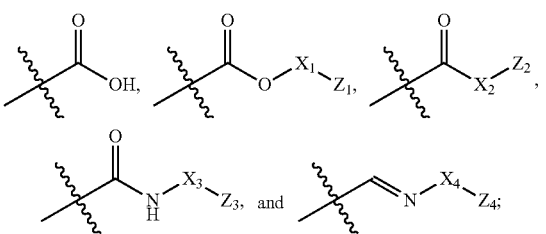

$A_2$ is selected from H, Me, Et, Pr, Bu, F, Cl, Br, I, OH, $OR^A$, $OC(O)R^A$, $NO_2$, $CF_3$, $CCl_3$, CN, $SO_3H$, CHO, $CH_2OH$, $C(O)OR^A$, $COR^A$, C(O)OK, $C(O)NR^A_2$, $C(O)N(R^A)(H)$, C=$NR^A$, $C(NR)R^A$, $C(S)NH_2$, $C(S)NR^A_2$, $C(S)N(R^A)(H)$,

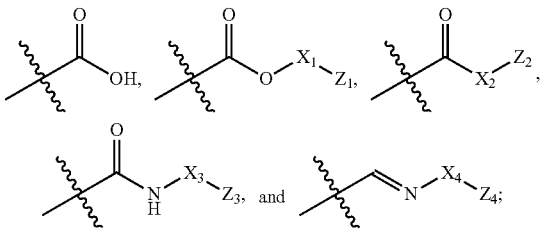

$E_1$ is selected from H, F, Cl, Br, I, $OC(O)R^E$, $NO_2$, $CF_3$, $CCl_3$, CN, $SO_3H$, CHO, $CH_2OH$, $C(O)OR^E$, $COR^E$, C(O)OK, $C(O)NR^E_2$, $C(O)N(R^E)(H)$, C=$NR^E$, $C(NR^E)R^E$, $C(S)NH_2$, $C(S)NR^E_2$, $C(S)N(R^E)(H)$,

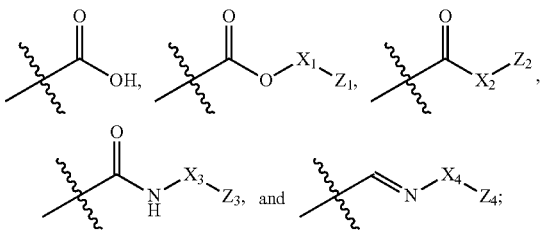

$E_2$ is selected from H, F, Cl, Br, I, $OC(O)R^E$, $NO_2$, $CF_3$, $CCl_3$, CN, $SO_3H$, CHO, $CH_2OH$, $C(O)OR^E$, $COR^E$, C(O)OK, $C(O)NR^E_2$, $C(O)N(R^E)(H)$, C=$NR^E$, $C(NR^E)R^E$, $C(S)NH_2$, $C(S)NR^E_2$, $C(S)N(R^E)(H)$,

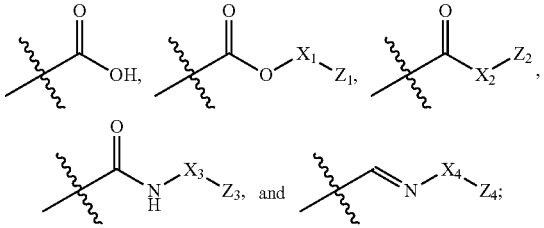

D is selected from H, F, Cl, Br, I, $OC(O)R^D$, $NO_2$, $CF_3$, $CCl_3$, CN, $SO_3H$, CHO, $CH_2OH$, $COOR^D$, $COR^D$, C(O)OK, $C(O)NR^D_2$, $C(O)N(R^D)(H)$, C=$NR^D$, $C(NR^D)R^D$, $C(S)NH_2$, $C(S)NR^D_2$, $C(S)N(R^D)(H)$,

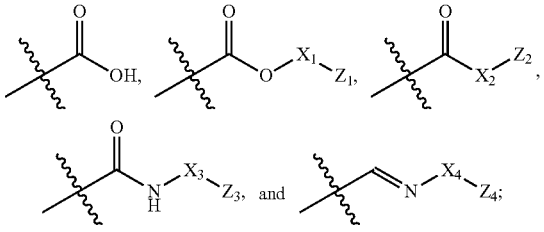

$G_1$ is selected from H, F, Cl, Br, I, $OC(O)R^G$, $NO_2$, $CF_3$, $CCl_3$, CN, $SO_3H$, CHO, $CH_2OH$, $C(O)OR^G$, $COR^G$, C(O)OK, C(O)NR$^G_2$, C(O)N(R$^G$)(H), C=NR$^G$, C(NR$^G$)R$^G$, C(S)NH$_2$, C(S)NR$^G_2$, C(S)N(R$^G$)(H),

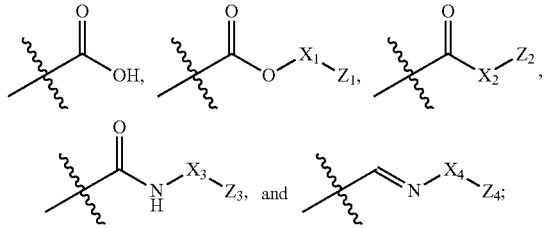

G$_2$ is selected from H, F, Cl, Br, I, OC(O)R$^G$, NO$_2$, CF$_3$, CCl$_3$, CN, SO$_3$H, CHO, CH$_2$OH, C(O)OR$^G$, COR$^G$, C(O)OK, C(O)NR$^G_2$, C(O)N(R$^G$)(H), C=NR$^G$, C(NR$^G$)R$^G$, C(S)NH$_2$, C(S)NR$^G_2$, C(S)N(R$^G$)(H),

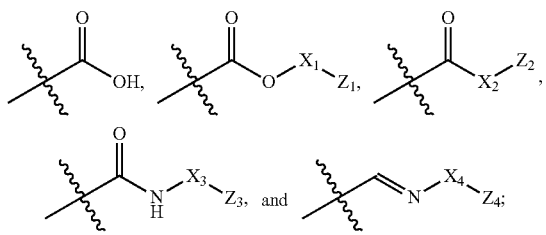

Q$_1$ is selected from H, Me, Et, Pr, Bu, F, Cl, Br, I, OH, OR$^Q$,

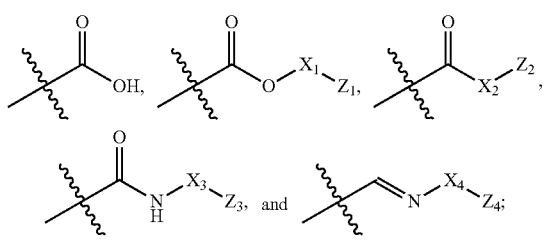

Q$_2$ is selected from H, Me, Et, Pr, Bu, F, Cl, Br, I, OH, OR$^Q$,

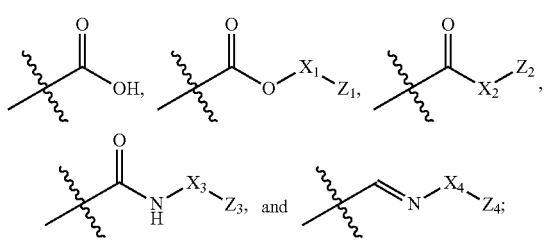

provided that at least one of A$_1$, A$_2$, E$_1$, E$_2$, D, G$_1$, G$_2$, Q$_1$, Q$_2$ is

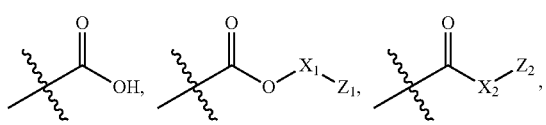

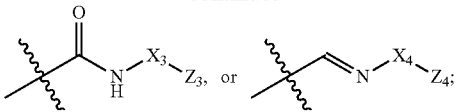

and wherein,

X$_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

X$_2$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

X$_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

X$_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

Z$_1$ is selected from SiR$_3$, Si(OR)$_3$, OH, NH, SH, aryl, C(O)OH, C(O)O$^-$, NR$_2$, or NHR;

Z$_2$ is selected from SiR$_3$, Si(OR)$_3$, OH, NH, SH, aryl, C(O)OH, C(O)O$^-$, NR$_2$, or NHR;

Z$_3$ is selected from SiR$_3$, Si(OR)$_3$, OH, NH, SH, aryl, C(O)OH, C(O)O$^-$, NR$_2$, or NHR;

Z$_4$ is selected from SiR$_3$, Si(OR)$_3$, OH, NH, SH, aryl, C(O)OH, C(O)O$^-$, NR$_2$, or NHR;

R$^A$ is a 1-20 carbon alkyl, 1-20 carbon aryl or 1-20 carbon alkenyl group, optionally substituted with one or more of: =O, =S, —OH, —SH, —CN, —C(O)OH, —CHO, —CONH$_2$, —COSH or —SO$_3$H;

R$^E$ is a 1-20 carbon alkyl, 1-20 carbon aryl or 1-20 carbon alkenyl group, optionally substituted with one or more of: =O, =S, —OH, —SH, —NH$_2$, —CN, —C(O)OH, —CHO, —CONH$_2$, —COSH or —SO$_3$H;

R$^D$ is a 1-20 carbon alkyl, 1-20 carbon aryl or 1-20 carbon alkenyl group, optionally substituted with one or more of: =O, =S, —OH, —SH, —CN, —C(O)OH, —CHO, —CONH$_2$, —COSH or —SO$_3$H;

R$^G$ is a 1-20 carbon alkyl, 1-20 carbon aryl or 1-20 carbon alkenyl group, optionally substituted with one or more of: =O, =S, —OH, —SH, —CN, —C(O)OH, —CHO, —CONH$_2$, —COSH or —SO$_3$H;

R$^Q$ is a 1-20 carbon alkyl, 1-20 carbon aryl or 1-20 carbon alkenyl group, optionally substituted with one or more of: =O, =S, —OH, —SH, —NH$_2$, —CN, —C(O)OH, —CHO, —CONH$_2$, —COSH or —SO$_3$H; and R and R' are a 1-10 carbon alkyl or 1-10 carbon aryl, optionally substituted with one or more of: =O, =S, —OH, —SH, —NH$_2$, —CN, —C(O)OH, —CHO, —CONH$_2$, —COSH or —SO$_3$H.

13. The compound of claim 11, wherein

A$_1$ is H;

A$_2$ is H;

E$_1$ is selected from H, F, Cl, Br, I, OC(O)R$^E$, NO$_2$, CF$_3$, CCl$_3$, CN, SO$_3$H, C(O)OH, CHO, CH$_2$OH, C(O)OR$^E$, COR$^E$, C(O)OK, C(O)NR$^E_2$, C(O)N(R$^E$)(H), C=NR$^E$, C(NR$^E$)R$^E$, C(S)NH$_2$, C(S)NR$^E_2$, C(S)N(R$^E$)(H),

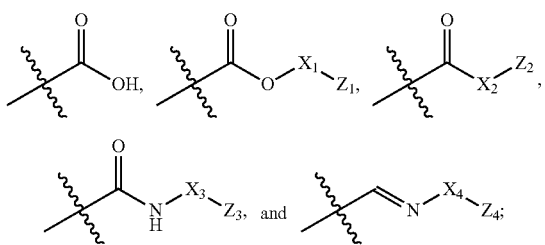

E₂ is selected from H, F, Cl, Br, I, OC(O)R^E, NO₂, CF₃, CCl₃, CN, SO₃H, C(O)OH, CHO, CH₂OH, C(O)OR^E, COR^E, C(O)OK, C(O)NR^E₂, C(O)N(R^E)(H), C=NR^E, C(NR^E)R^E, C(S)NH₂, C(S)NR^E₂, C(S)N(R^E)(H),

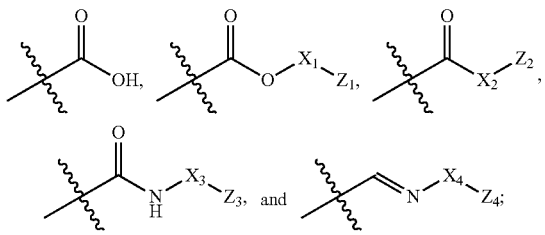

D is selected from H, F, Cl, Br, I, OC(O)R^D, NO₂, CF₃, CCl₃, CN, SO₃H, C(O)OH, CHO, CH₂OH, COOR^D, COR^D, C(O)OK, C(O)NR^D₂, C(O)N(R^D)(H), C=NR^D, C(NR^D)R^D, C(S)NH₂, C(S)NR^D₂, C(S)N(R^D)(H),

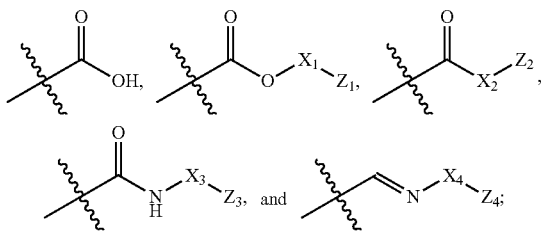

G₁ is selected from H, F, Cl, Br, OC(O)R^G, NO₂, CF₃, CCl₃, CN, SO₃H, C(O)OH, CHO, CH₂OH, C(O)OR^G, COR^G, C(O)OK, C(O)NR^G₂, C(O)N(R^G)(H), C=NR^G, C(NR^G)R^G,

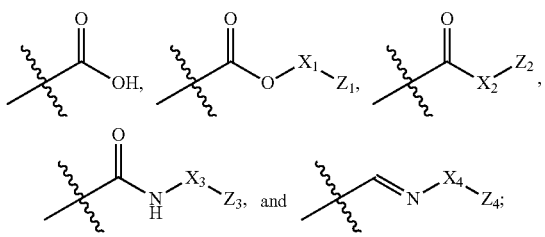

G₂ is selected from H, F, Cl, Br, OC(O)R^G, NO₂, CF₃, CCl₃, CN, SO₃H, CHO, CH₂OH, C(O)OR^G, COR^G, C(O)OK, C(O)NR^G₂, C(O)N(R^G)(H), C=NR^G, C(NR^G)R^G,

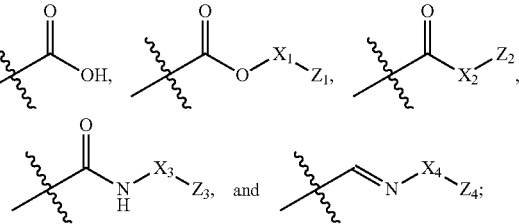

Q₁ is H;
Q₂ is H;
provided that at least one of E₁, E₂, D, G₁, or G₂ is

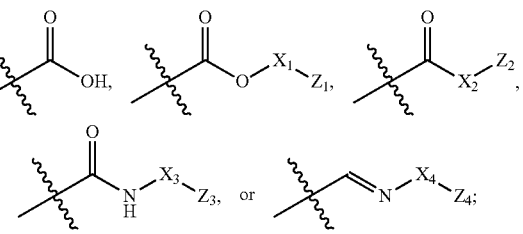

and wherein,

X₁ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;

X₂ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;

X₃ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;

X₄ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;

Z₁ is selected from SiR₃, Si(OR)₃, OH, NH, SH, aryl, C(O)OH, C(O)O⁻, NR₂, or NHR;

Z₂ is selected from SiR₃, Si(OR)₃, OH, NH, SH, aryl, C(O)OH, C(O)O⁻, NR₂, or NHR;

Z₃ is selected from SiR₃, Si(OR)₃, OH, NH, SH, aryl, C(O)OH, C(O)O⁻, NR₂, or NHR;

Z₄ is selected from SiR₃, Si(OR)₃, OH, NH, SH, aryl, C(O)OH, C(O)O⁻, NR₂, or NHR;

R^E is a 1-20 carbon alkyl, 1-20 carbon aryl or 1-20 carbon alkenyl group, optionally substituted with one or more of: =O, —OH, —SH, —NH₂, —CN, —C(O)OH, —CHO, —CONH₂ or —SO₃H;

R^D is a 1-20 carbon alkyl, 1-20 carbon aryl or 1-20 carbon alkenyl group, optionally substituted with one or more of: =O, —OH, —SH, —NH₂, —CN, —C(O)OH, —CHO, —CONH₂ or —SO₃H;

R^G is a 1-20 carbon alkyl, 1-20 carbon aryl or 1-20 carbon alkenyl group, optionally substituted with one or more of: =O, =S, —OH, —SH, —NH₂, —CN, —C(O)OH, —CHO, —CONH₂, —COSH or —SO₃H; and R and R' are a 1-10 carbon alkyl or 1-10 carbon aryl, optionally substituted with one or more of: =O, —OH, —SH, —NH₂, —CN, —C(O)OH, —CHO, —CONH₂ or —SO₃H.

14. The compound of claim 11, wherein
$A_1$ is H;
$A_2$ is H;
$E_1$ is selected from H, F, Cl, Br, OC(O)$R^E$, NO$_2$, CF$_3$, CCl$_3$, CN, SO$_3$H, CHO, CH$_2$OH, C(O)O$R^E$, CO$R^E$, C(O)OK, C(O)N$R^E{}_2$, C(O)N($R^E$)(H), C=N$R^E$, C(N$R^E$)$R^E$,

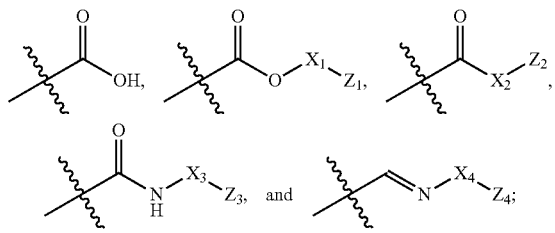

$E_2$ is selected from H, F, Cl, Br, OC(O)$R^E$, NO$_2$, CF$_3$, CCl$_3$, CN, SO$_3$H, CHO, CH$_2$OH, C(O)O$R^E$, CO$R^E$, C(O)OK, C(O)N$R^E{}_2$, C(O)N($R^E$)(H), C=N$R^E$, C(N$R^E$)$R^E$,

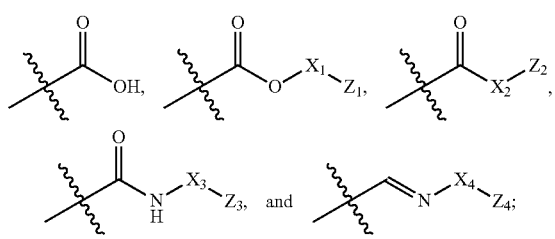

D is selected from H, F, Cl, Br, OC(O)$R^D$, NO$_2$, CF$_3$, CCl$_3$, CN, SO$_3$H, CHO, CH$_2$OH, COO$R^D$, CO$R^D$, C(O)OK, C(O)N$R^D{}_2$, C(O)N($R^D$)(H), C=N$R^D$, C(N$R^D$)$R^D$,

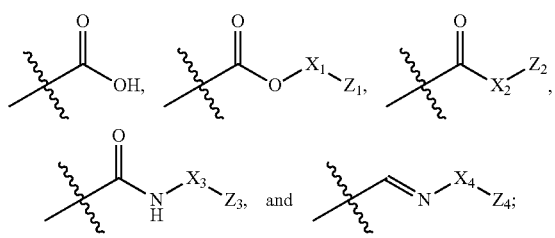

$G_1$ is selected from H, F, Cl, Br, OC(O)$R^G$, NO$_2$, CF$_3$, CCl$_3$, CN, SO$_3$H, CHO, CH$_2$OH, C(O)O$R^G$, CO$R^G$, C(O)OK, C(O)N$R^G{}_2$, C(O)N($R^G$)(H), C=N$R^G$, C(N$R^G$)$R^G$,

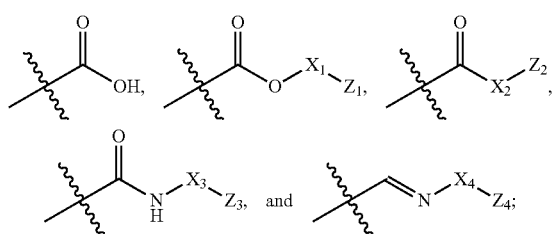

$G_2$ is selected from H, F, Cl, Br, OC(O)$R^G$, NO$_2$, CF$_3$, CCl$_3$, CN, SO$_3$H, CHO, CH$_2$OH, C(O)O$R^G$, CO$R^G$, C(O)OK, C(O)N$R^G{}_2$, C(O)N($R^G$)(H), C=N$R^G$, C(N$R^G$)$R^G$,

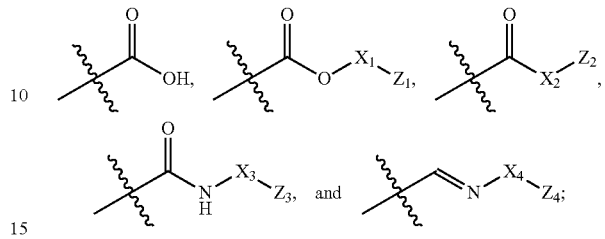

$Q_1$ is H;
$Q_2$ is H;
provided that at least one of $E_1$, $E_2$, D, $G_1$, or $G_2$ is

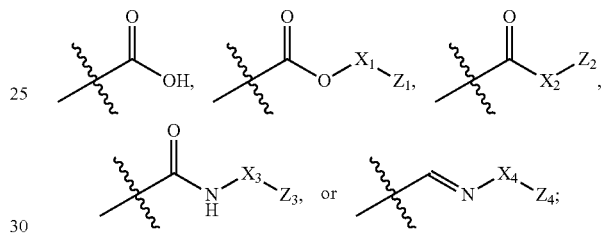

and wherein,
$X_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
$X_2$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
$X_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
$X_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
$Z_1$ is selected from SiR$_3$, Si(OR)$_3$, OH, NH, SH, aryl, C(O)OH, C(O)O$^-$, NR$_2$, or NHR;
$Z_2$ is selected from SiR$_3$, Si(OR)$_3$, OH, NH, SH, aryl, C(O)OH, C(O)O$^-$, NR$_2$, or NHR;
$Z_3$ is selected from SiR$_3$, Si(OR)$_3$, OH, NH, SH, aryl, C(O)OH, C(O)O$^-$, NR$_2$, or NHR;
$Z_4$ is selected from SiR$_3$, Si(OR)$_3$, OH, NH, SH, aryl, C(O)OH, C(O)O$^-$, NR$_2$, or NHR;
$R^E$ is a 1-20 carbon alkyl, 1-20 carbon aryl or 1-20 carbon alkenyl group, optionally substituted with one or more of: =O, —OH, —SH, —NH$_2$, —CN, —C(O)OH, —CHO, —CONH$_2$ or —SO$_3$H;
$R^D$ is a 1-20 carbon alkyl, 1-20 carbon aryl or 1-20 carbon alkenyl group, optionally substituted with one or more of: =O, —OH, —SH, —NH$_2$, —CN, —C(O)OH, —CHO, —CONH$_2$ or —SO$_3$H;
$R^G$ is a 1-20 carbon alkyl, 1-20 carbon aryl or 1-20 carbon alkenyl group, optionally substituted with one or more of: =O, =S, —OH, —SH, —NH$_2$, —CN, —C(O)OH, —CHO, —CONH$_2$, —COSH or —SO$_3$H; and R and R' are a 1-10 carbon alkyl or 1-10 carbon aryl, optionally substituted with one or more of: =O, —OH, —SH, —NH$_2$, —CN, —C(O)OH, —CHO, —CONH$_2$ or —SO$_3$H.

15. The compound of claim 11, wherein

A$_1$ is H;

A$_2$ is H;

E$_1$ is selected from H, F, Cl, Br, OC(O)R$^E$, NO$_2$, CF$_3$, CCl$_3$, CN, SO$_3$H, CHO, CH$_2$OH, C(O)OR$^E$, COR$^E$, C(O)OK, C(O)NR$^E$$_2$, C(O)N(R$^E$)(H), C=NR$^E$, C(NR$^E$)R$^E$,

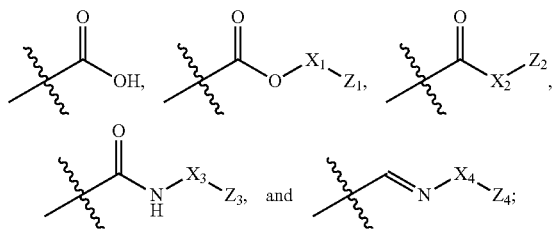

E$_2$ is selected from H, F, Cl, Br, OC(O)R$^E$, NO$_2$, CF$_3$, CCl$_3$, CN, SO$_3$H, CHO, CH$_2$OH, C(O)OR$^E$, COR$^E$, C(O)OK, C(O)NR$^E$$_2$, C(O)N(R$^E$)(H), C=NR$^E$, C(NR$^E$)R$^E$,

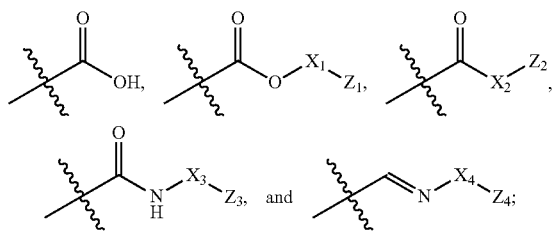

D is selected from H, F, Cl, Br, OC(O)R$^D$, NO$_2$, CF$_3$, CCl$_3$, CN, SO$_3$H, CHO, CH$_2$OH, COOR$^D$, COR$^D$, C(O)OK, C(O)NR$^D$$_2$, C(O)N(R$^D$)(H), C=NR$^D$, C(NR$^D$)R$^D$,

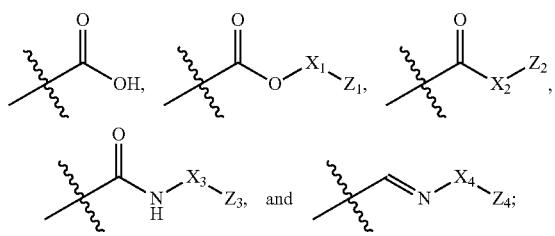

G$_1$ is selected from H, F, Cl, Br, NO$_2$, CF$_3$, CCl$_3$, CN, CHO, CH$_2$OH,

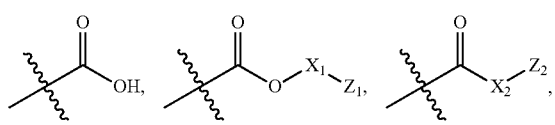

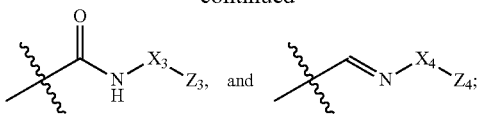

G$_2$ is selected from H, F, Cl, Br, NO$_2$, CF$_3$, CCl$_3$, CN, CHO, CH$_2$OH,

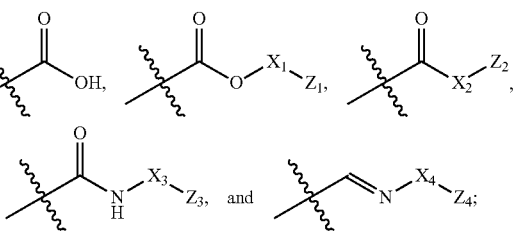

Q$_1$ is H;

Q$_2$ is H;

provided that at least one of E$_1$, E$_2$ or D is

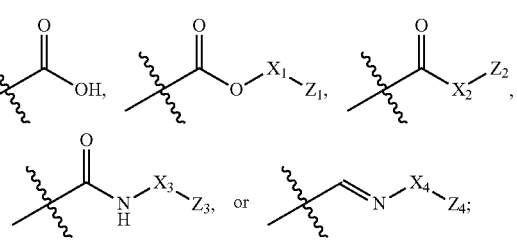

and wherein,

X$_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

X$_2$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

X$_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

X$_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

Z$_1$ is selected from SiR$_3$, Si(OR)$_3$, OH, NH, SH, aryl, C(O)OH, C(O)O$^-$, NR$_2$, or NHR;

Z$_2$ is selected from SiR$_3$, Si(OR)$_3$, OH, NH, SH, aryl, C(O)OH, C(O)O$^-$, NR$_2$, or NHR;

Z$_3$ is selected from SiR$_3$, Si(OR)$_3$, OH, NH, SH, aryl, C(O)OH, C(O)O$^-$, NR$_2$, or NHR;

Z$_4$ is selected from SiR$_3$, Si(OR)$_3$, OH, NH, SH, aryl, C(O)OH, C(O)O$^-$, NR$_2$, or NHR;

R$^E$ is a 1-20 carbon alkyl, 1-20 carbon aryl or 1-20 carbon alkenyl group, optionally substituted with one or more of: =O, —OH, —SH, —NH$_2$, —CN, —C(O)OH, —CHO, —CONH$_2$ or —SO$_3$H;

R$^D$ is a 1-20 carbon alkyl, 1-20 carbon aryl or 1-20 carbon alkenyl group, optionally substituted with one or more of: =O, —OH, —SH, —NH₂, —CN, —C(O)OH, —CHO, —CONH₂ or —SO₃H; and
R and R' are a 1-10 carbon alkyl or 1-10 carbon aryl, optionally substituted with one or more of: =O, —OH, —SH, —NH₂, —CN, —C(O)OH, —CHO, —CONH₂ or —SO₃H.

16. The compound of claim 11, wherein
$A_1$ is H;
$A_2$ is H;
$E_1$ is selected from H, F, Cl, Br, OC(O)$R^E$, NO₂, CF₃, CCl₃, CN, SO₃H, CHO, CH₂OH, C(O)O$R^E$, COR$^E$, C(O)OK, C(O)N$R^E{}_2$, C(O)N($R^E$)(H), C=N$R^E$, C(N$R^E$)$R^E$,

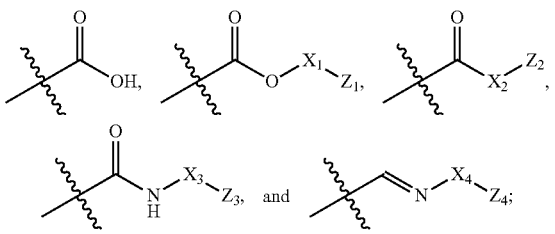

$E_2$ is selected from H, F, Cl, Br, OC(O)$R^E$, NO₂, CF₃, CCl₃, CN, SO₃H, CHO, CH₂OH, C(O)O$R^E$, COR$^E$, C(O)OK, C(O)N$R^E{}_2$, C(O)N($R^E$)(H), C=N$R^E$, C(N$R^E$)$R^E$,

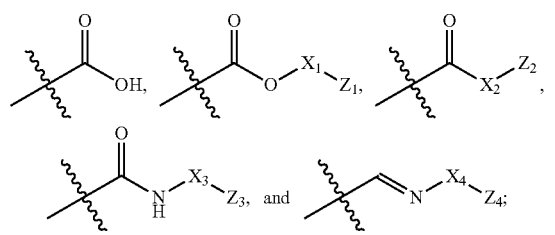

D is selected from H, F, Cl, Br, OC(O)$R^D$, NO₂, CF₃, CCl₃, CN, SO₃H, CHO, CH₂OH, COOR$^D$, COR$^D$, C(O)OK, C(O)N$R^D{}_2$, C(O)N($R^D$)(H), C=N$R^D$, C(N$R^D$)$R^D$,

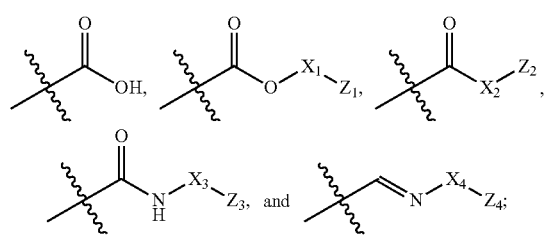

$G_1$ is H;
$G_2$ is H;
$Q_1$ is H;
$Q_2$ is H;
provided that at least one of $E_1$, $E_2$ or D is

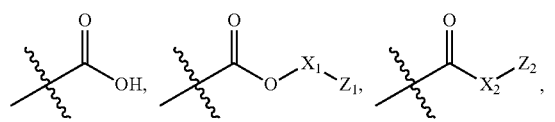

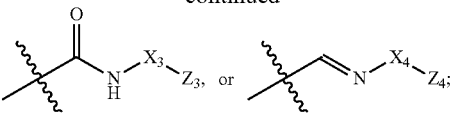

and wherein,
$X_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;
$X_2$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;
$X_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;
$X_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR₃;
$Z_1$ is selected from Si$R_3$, Si(OR)₃, OH, NH, SH, aryl, C(O)OH, C(O)O⁻, NR₂, or NHR;
$Z_2$ is selected from Si$R_3$, Si(OR)₃, OH, NH, SH, aryl, C(O)OH, C(O)O⁻, NR₂, or NHR;
$Z_3$ is selected from Si$R_3$, Si(OR)₃, OH, NH, SH, aryl, C(O)OH, C(O)O⁻, NR₂, or NHR;
$Z_4$ is selected from Si$R_3$, Si(OR)₃, OH, NH, SH, aryl, C(O)OH, C(O)O⁻, NR₂, or NHR;
$R^E$ is a 1-20 carbon alkyl, 1-20 carbon aryl or 1-20 carbon alkenyl group, optionally substituted with one or more of: =O, —OH, —SH, —NH₂, —CN, —C(O)OH, —CHO, —CONH₂ or —SO₃H;
$R^D$ is a 1-20 carbon alkyl, 1-20 carbon aryl or 1-20 carbon alkenyl group, optionally substituted with one or more of: =O, —OH, —SH, —NH₂, —CN, —C(O)OH, —CHO, —CONH₂ or —SO₃H; and
R and R' are a 1-10 carbon alkyl or 1-10 carbon aryl, optionally substituted with one or more of: =O, —OH, —SH, —NH₂, —CN, —C(O)OH, —CHO, —CONH₂ or —SO₃H.

17. The compound of claim 11, wherein
$A_1$ is H;
$A_2$ is H;
$E_1$ is selected from H, F, Cl, Br, OC(O)$R^E$, NO₂, CF₃, CCl₃, CN, SO₃H, CH₂OH, CHO, C(O)O$R^E$, COR$^E$, C(O)OK, C(O)N$R^E{}_2$, C(O)N($R^E$)(H), C=N$R^E$, C(N$R^E$)$R^E$,

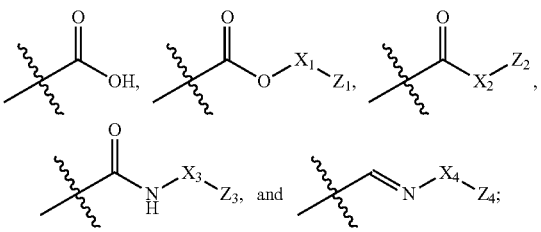

$E_2$ is selected from H, F, Cl, Br, OC(O)$R^E$, NO₂, CF₃, CCl₃, CN, SO₃H, CH₂OH, CHO, C(O)O$R^E$, COR$^E$, C(O)OK, C(O)N$R^E{}_2$, C(O)N($R^E$)(H), C=N$R^E$, C(N$R^E$)$R^E$,

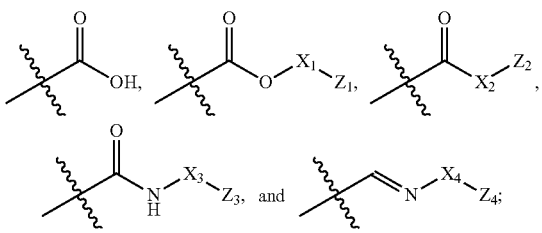

D is selected from H, F, Cl, Br், NO$_2$, CF$_3$, CCl$_3$, CN, SO$_3$H, CH$_2$OH, C(O)OH, CHO, CH$_2$OH,

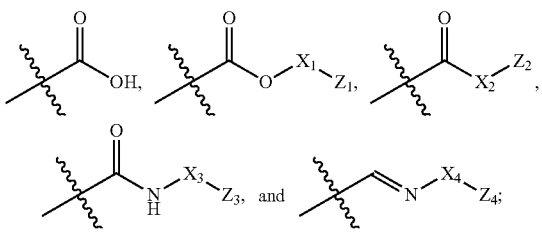

G$_1$ is H;
G$_2$ is H;
Q$_1$ is H;
Q$_2$ is H;
provided that at least one of E$_1$, E$_2$ or D is

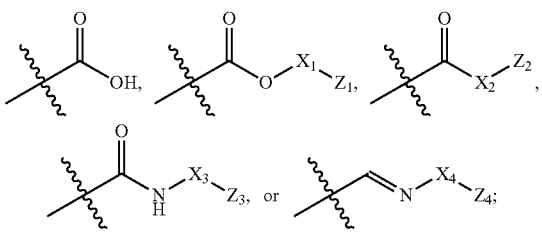

and wherein,
X$_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
X$_2$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
X$_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
X$_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;
Z$_1$ is selected from SiR$_3$, Si(OR)$_3$, OH, NH, SH, aryl, C(O)OH, C(O)O$^-$, NR$_2$, or NHR;
Z$_2$ is selected from SiR$_3$, Si(OR)$_3$, OH, NH, SH, aryl, C(O)OH, C(O)O$^-$, NR$_2$, or NHR;
Z$_3$ is selected from SiR$_3$, Si(OR)$_3$, OH, NH, SH, aryl, C(O)OH, C(O)O$^-$, NR$_2$, or NHR;
Z$_4$ is selected from SiR$_3$, Si(OR)$_3$, OH, NH, SH, aryl, C(O)OH, C(O)O$^-$, NR$_2$, or NHR;

R$^E$ is a 1-20 carbon alkyl, 1-20 carbon aryl or 1-20 carbon alkenyl group, optionally substituted with one or more of: =O, —OH, —SH, —NH$_2$, —CN, —C(O)OH, —CHO, —CONH$_2$ or —SO$_3$H; and
R and R' are a 1-10 carbon alkyl or 1-10 carbon aryl, optionally substituted with one or more of: =O, —OH, —SH, —NH$_2$, —CN, —C(O)OH, —CHO, —CONH$_2$ or —SO$_3$H.

18. The compound of claim 11, wherein
A$_1$ is H;
A$_2$ is H;
E$_1$ is selected from H, F, Cl, Br, OC(O)R$^E$, NO$_2$, CF$_3$, CCl$_3$, CN, SO$_3$H, CH$_2$OH, CHO, C(O)OR$^E$, COR$^E$, C(O)OK, C(O)NR$^E{}_2$, C(O)N(R$^E$)(H), C=NR$^E$, C(NR$^E$)R$^E$,

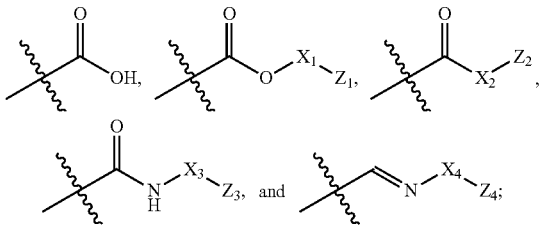

E$_2$ is selected from H, F, Cl, Br, OC(O)R$^E$, NO$_2$, CF$_3$, CCl$_3$, CN, SO$_3$H, CH$_2$OH, CHO, C(O)OR$^E$, COR$^E$, C(O)OK, C(O)NR$^E{}_2$, C(O)N(R$^E$)(H), C=NR$^E$, C(NR$^E$)R$^E$,

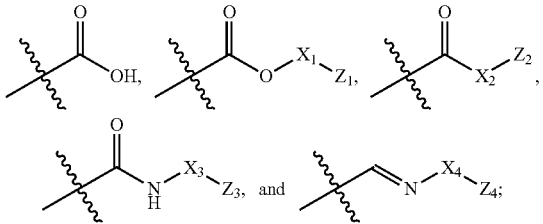

D is H;
G$_1$ is H;
G$_2$ is H;
Q$_1$ is H;
Q$_2$ is H;
provided that at least one of E$_1$ or E$_2$ is

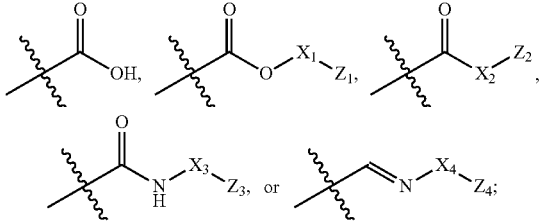

and wherein,
X$_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or NR$_3$;

$X_2$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$X_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$X_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$Z_1$ is selected from $SiR_3$, $Si(OR)_3$, OH, NH, SH, aryl, C(O)OH, C(O)O⁻, $NR_2$, or NHR;

$Z_2$ is selected from $SiR_3$, $Si(OR)_3$, OH, NH, SH, aryl, C(O)OH, C(O)O⁻, $NR_2$, or NHR;

$Z_3$ is selected from $SiR_3$, $Si(OR)_3$, OH, NH, SH, aryl, C(O)OH, C(O)O⁻, $NR_2$, or NHR;

$Z_4$ is selected from $SiR_3$, $Si(OR)_3$, OH, NH, SH, aryl, C(O)OH, C(O)O⁻, $NR_2$, or NHR;

$R^E$ is a 1-20 carbon alkyl, 1-20 carbon aryl or 1-20 carbon alkenyl group, optionally substituted with one or more of: =O, —OH, —SH, —$NH_2$, —CN, —C(O)OH, —CHO, —$CONH_2$ or —$SO_3H$; and R and R' are a 1-10 carbon alkyl or 1-10 carbon aryl, optionally substituted with one or more of: =O, —OH, —SH, —$NH_2$, —CN, —C(O)OH, —CHO, —$CONH_2$ or —$SO_3H$.

19. The compound of claim 11, wherein
$A_1$ is H;
$A_2$ is H;
$E_1$ is selected from H, $CH_2OH$, CHO, $C(O)OR^E$, C(O)OK, $C(O)N(R^E)(H)$, C=$NR^E$,

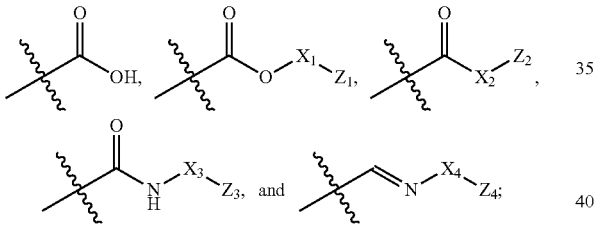

$E_2$ is selected from H, $CH_2OH$, CHO, $C(O)OR^E$, C(O)OK, $C(O)N(R^E)(H)$, C=$NR^E$,

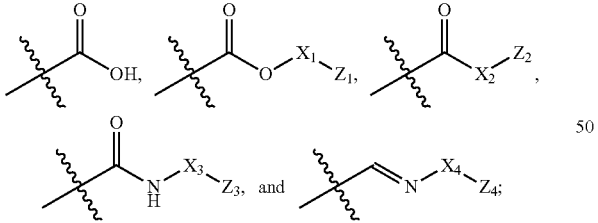

D is H;
$G_1$ is H;
$G_2$ is H;
$Q_1$ is H;
$Q_2$ is H;
provided that at least one of $E_1$ or $E_2$ is

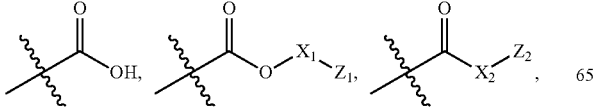

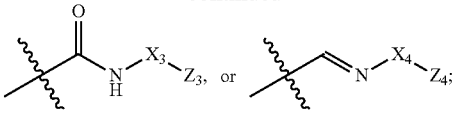

and wherein, $X_1$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$X_2$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$X_3$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$X_4$ is a 1-20 carbon, saturated or unsaturated hydrocarbyl chain, or an ether group having the structure R—O—R', wherein the hydrocarbyl chain or the ether group is optionally substituted by OH, F, Cl, Br, I, or $NR_3$;

$Z_1$ is selected from $SiR_3$, $Si(OR)_3$, OH, NH, SH, aryl, C(O)OH, C(O)O⁻, $NR_2$, or NHR;

$Z_2$ is selected from $SiR_3$, $Si(OR)_3$, OH, NH, SH, aryl, C(O)OH, C(O)O⁻, $NR_2$, or NHR;

$Z_3$ is selected from $SiR_3$, $Si(OR)_3$, OH, NH, SH, aryl, C(O)OH, C(O)O⁻, $NR_2$, or NHR;

$Z_4$ is selected from $SiR_3$, $Si(OR)_3$, OH, NH, SH, aryl, C(O)OH, C(O)O⁻, $NR_2$, or NHR;

$R^E$ is a 1-20 carbon alkyl, 1-20 carbon aryl or 1-20 carbon alkenyl group, optionally substituted with one or more of: =O, —OH, —SH, —$NH_2$, —CN, —C(O)OH, —CHO, —$CONH_2$ or —$SO_3H$; and R and R' are a 1-10 carbon alkyl or 1-10 carbon aryl, optionally substituted with one or more of: =O, —OH, —SH, —$NH_2$, —CN, —C(O)OH, —CHO, —$CONH_2$ or —$SO_3H$.

20. The compound of claim 11, wherein the compound is selected from one or more of the following:

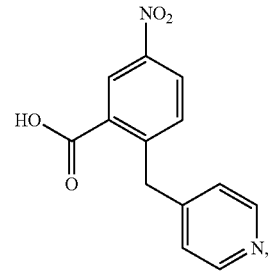

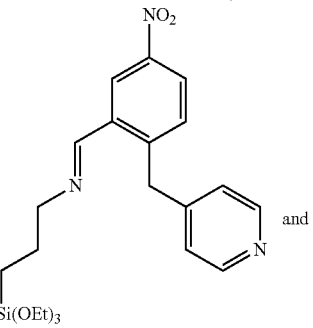

and

-continued

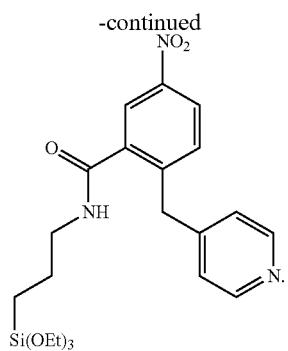

21. A method for detecting alkylating agents, the method comprising the use of a compound of claim 1 as a colorimetric indicator.

22. A composition, the composition comprising (a) compound of claim 1 and (b) a linker substrate.

23. A composition, the composition comprising (a) compound of claim 11 and (b) a linker substrate, wherein the compound is bound to the linker substrate by

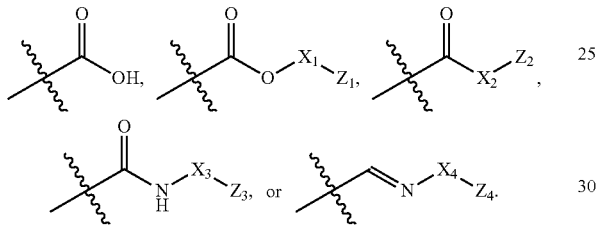

24. A commercial package comprising the composition of claim 22, with instructions for use in detecting any alkylating agent.

25. A commercial package comprising the composition of claim 23, with instructions for use in detecting any alkylating agent.

26. A method for detecting alkylating agents, the method comprising the use of a compound of claim 11 as a colorimetric indicator.

27. A compound selected from the group consisting of:

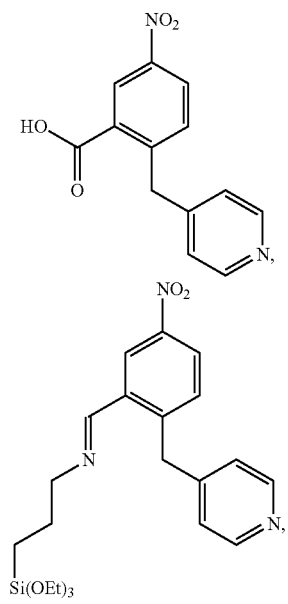

-continued

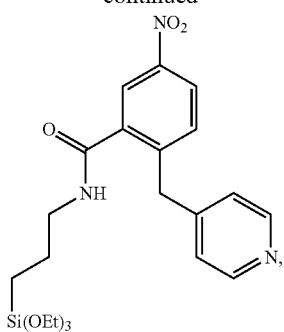

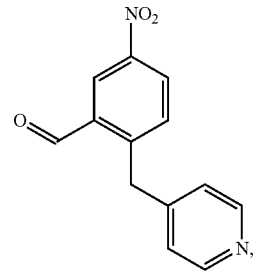

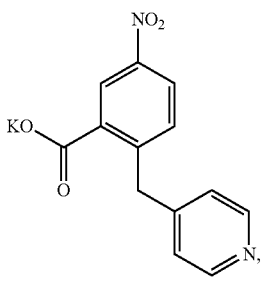

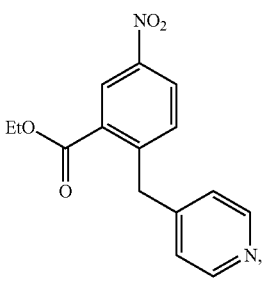

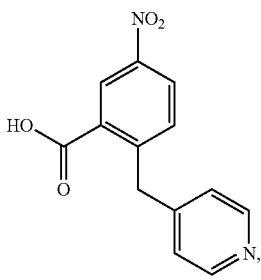

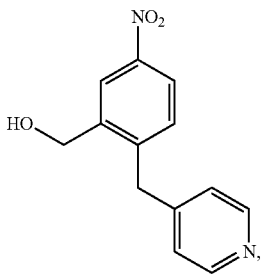

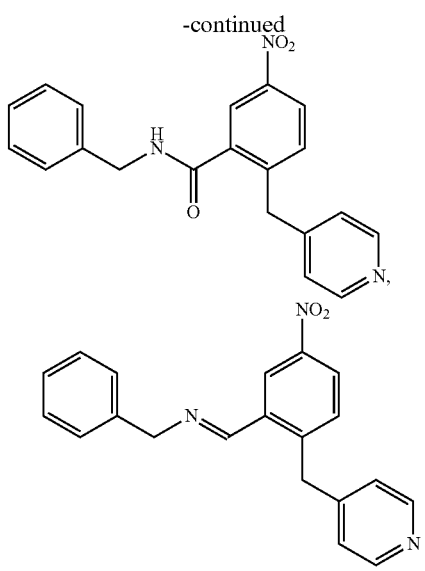
and
wherein K is potassium.

UNITED STATES PATENT AND TRADEMARK OFFICE
CERTIFICATE OF CORRECTION

PATENT NO. : 9,638,690 B2
APPLICATION NO. : 14/927836
DATED : May 2, 2017
INVENTOR(S) : Jennifer Ann Love and Philip Andrew Provencher Page 1 of 3

It is certified that error appears in the above-identified patent and that said Letters Patent is hereby corrected as shown below:

In the Specification

Columns 19-20,

Lines 45-51, " 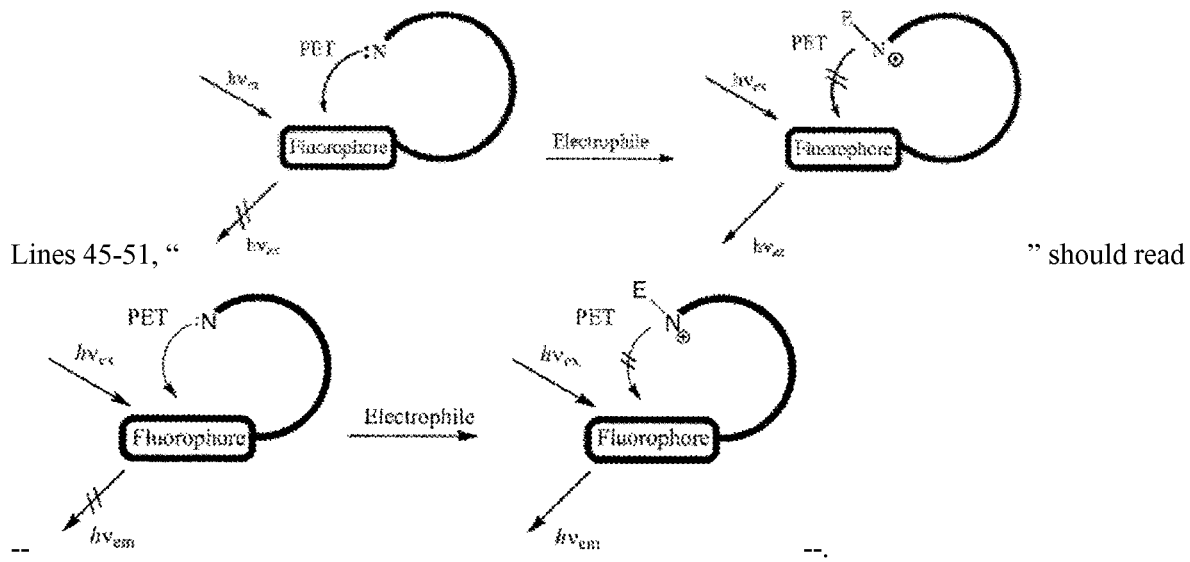 " should read

-- --.

Column 30,

Lines 60-64, " 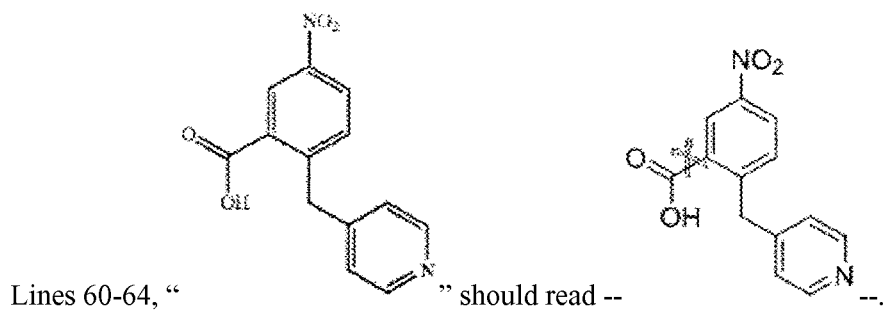 " should read -- --.

Signed and Sealed this
Twelfth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,638,690 B2

Column 32,

Lines 7-10, " " should read -- --.

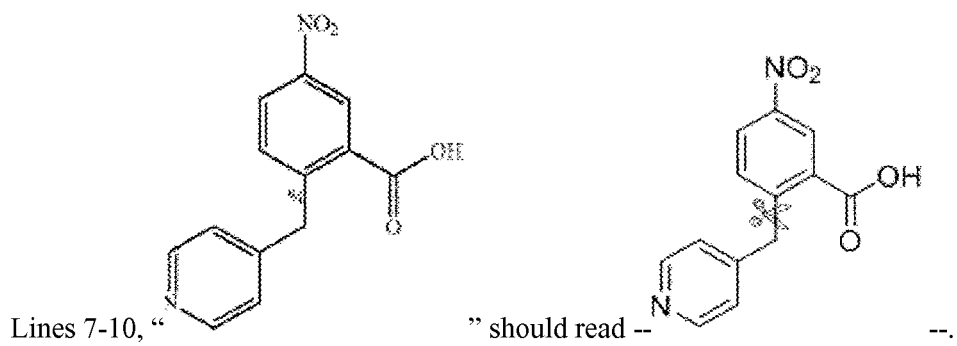

Column 44,

Lines 38-45, " " should read -- --.

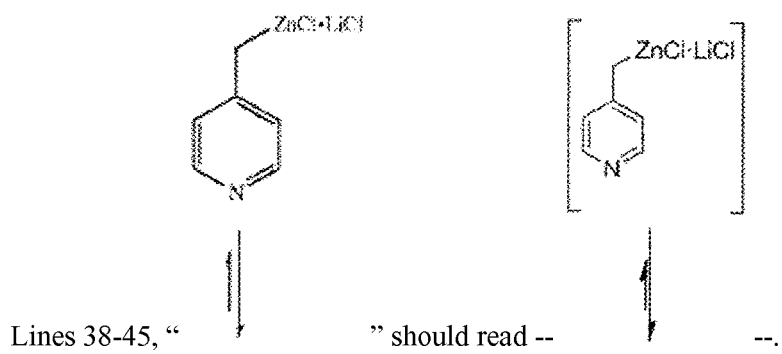

Column 47,

Lines 5-55, " " should read

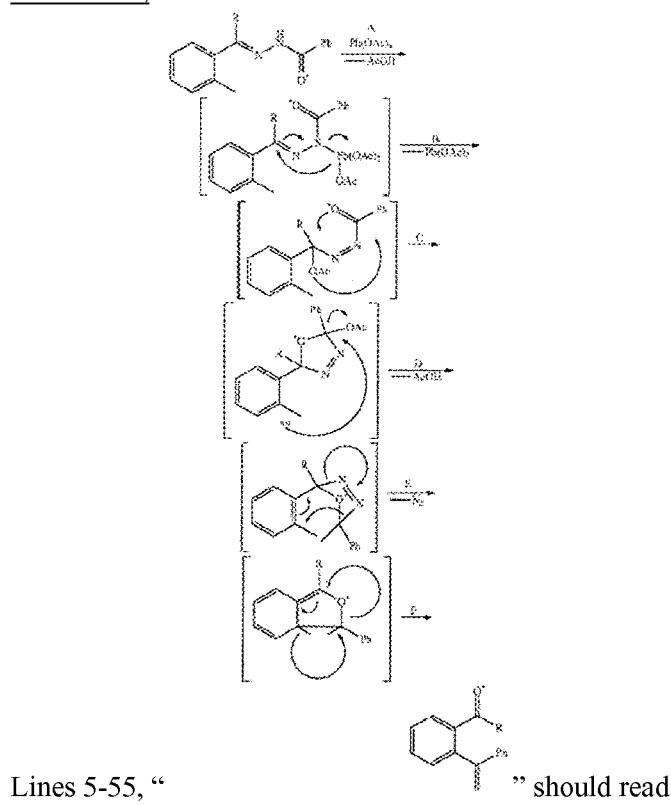

CERTIFICATE OF CORRECTION (continued)
U.S. Pat. No. 9,638,690 B2

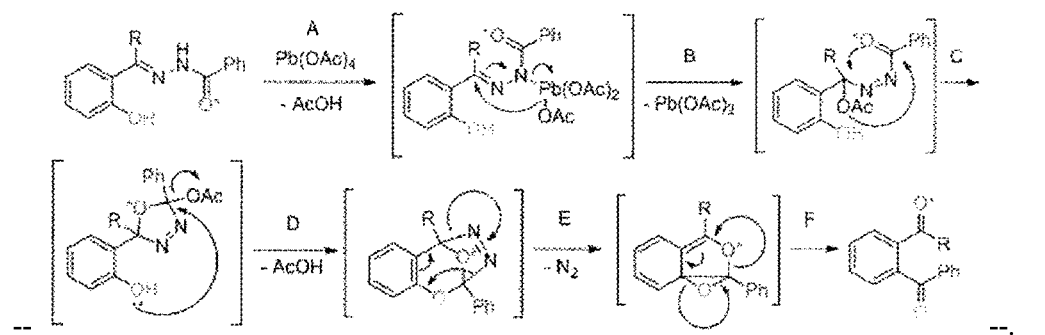

Column 58,

Lines 17-18, "[reaction arrow with 3.1 equiv. HO-CH2-CH2-OH]" should read --[reaction arrow with 3 equiv. HO-CH2-CH2-OH]--.

Column 84,
Line 37, "-SH, -CN," should read --SH, -NH2, -CN,--.

In the Claims

Column 84,
Line 45, "-SH, -CN," should read --SH, -NH2, -CN,--.

Column 84,
Line 49, "-SH, -CN," should read --SH, -NH2, -CN,--.